United States Patent [19]

Iwaki et al.

[11] Patent Number: 5,220,042

[45] Date of Patent: Jun. 15, 1993

[54] 1,4-BENZOQUINONE DERIVATIVES AND BENZENE DERIVATIVES, AND PROCESS FOR PREPARING THE SAME

[75] Inventors: Hideyuki Iwaki; Yoshiyasu Fukuyama, both of Tokushima; Kuniaki Matsui, Naruto, all of Japan

[73] Assignee: Otsuka Pharmaceutical Co., Ltd., Tokyo, Japan

[21] Appl. No.: 439,002

[22] Filed: Nov. 21, 1989

Related U.S. Application Data

[63] Continuation of Ser. No. 694,800, Jan. 25, 1985, abandoned.

[30] Foreign Application Priority Data

| | | |
|---|---|---|
| Jan. 26, 1984 [JP] | Japan | 59-13037 |
| Jul. 10, 1984 [JP] | Japan | 59-143858 |
| Jul. 11, 1984 [JP] | Japan | 59-144876 |
| Oct. 31, 1984 [JP] | Japan | 59-230683 |

[51] Int. Cl.$^5$ ............................................. C07C 50/00
[52] U.S. Cl. ................................. 552/307; 552/293; 552/306; 549/551; 549/554; 549/560
[58] Field of Search ................. 552/307, 283, 306; 549/551, 554, 560

[56] References Cited

U.S. PATENT DOCUMENTS

| | | | |
|---|---|---|---|
| 3,644,435 | 2/1972 | Folkers et al. | 568/652 |
| 4,139,545 | 2/1979 | Morimoto et al. | 260/396 R |

FOREIGN PATENT DOCUMENTS

| | | |
|---|---|---|
| 0038160 | 10/1981 | European Pat. Off. |
| 0038674 | 10/1981 | European Pat. Off. |
| 57-50935 | 3/1982 | Japan |

OTHER PUBLICATIONS

Chemical Abstracts 90(7):51176c.
CA 60:4049g 1963.
CA 72(9):42534u 1969.
CA 104(13):101940c 1983.

*Primary Examiner*—Paul J. Killos
*Attorney, Agent, or Firm*—Finnegan, Henderson, Farabow, Garrett & Dunner

[57] ABSTRACT

1,4-Benzoquinone derivatives and benzene derivatives having cerebral- and cardiac-blood flow improving activities and preventive activities of cerebral ischema with low toxicities, and thus are useful as activators for cardiac and cebral metabolisms, curing agents for heart failure, cardiac and cerebral blood flow improving agents, as well as anti-allergic agents for slow reacting allergy (IV-type allergy).

11 Claims, No Drawings

1,4-BENZOQUINONE DERIVATIVES AND BENZENE DERIVATIVES, AND PROCESS FOR PREPARING THE SAME

This application is a continuation of application Ser. No. 06/694,800, filed Jan. 25, 1985 now abandoned.

FIELD OF THE INVENTION

The present invention relates to novel 1,4-benzoquinone derivatives and benzene derivatives, and process for preparing the same, as well as to arachidonic acid 5-lipoxygenase inhibitor containing said derivative as the active ingredient.

The 1,4-benzoquinone derivatives and benzene derivatives of the present invention are represented by (1) the general formula (1),

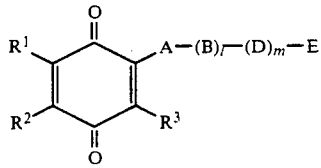

[wherein $R^1$ is a lower alkyl group, a lower alkoxy group, an amino group, a hydroxyl group or a lower alkanoyloxy group $R^2$ is a hydrogen atom, a halogen atom, a lower alkyl group, a lower alkoxy group, a lower alkoxycarbonyl group, a lower alkylthio group or a hydroxy-lower alkyl group; $R^3$ is a hydroxyl group, a lower alkyl group, a lower alkoxy group, an amino group or a lower alkanoyloxy group; A and D are each an alkylene group having 1 to 10 carbon atoms; B is a group of the formula —CH=CH—,

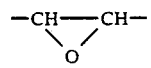

—C≡C— or —CH(OH)—CH(OH)—; l and m are each zero or 1; and E is a group of the formula,

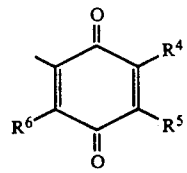

((wherein $R^4$ is a lower alkyl group, a lower alkoxy group, an amino group, a hydroxyl group or a lower alkanoyloxy group; $R^5$ is a hydrogen atom, a halogen atom, a lower alkyl group, a lower alkoxy group, a lower alkoxycarbonyl group, a lower alkylthio group, a hydroxy-lower alkyl group, a group of the formula —G—C≡C—$R^7$ (wherein G is a lower alkylene group; and $R^7$ is a lower alkyl group); or a group of the formula,

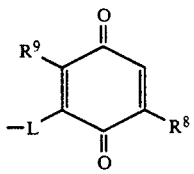

(wherein L is a lower alkylene group; and $R^8$ and $R^9$ are each a lower alkoxy group); $R^6$ is a lower alkyl group, a hydroxyl group, a lower alkoxy group, an amino group or a lower alkanoyloxy group)) or a group of the formula,

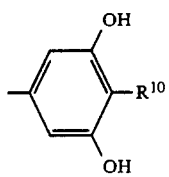

(wherein $R^{10}$ is a hydrogen atom or a methyl group), and when l is zero, then either one or both of the alkylene group having 1 to 10 carbon atoms represented by the symbols A and D may have an oxygen atom, sulfur atom or a group of the formula —S—S— as hetero atoms in the alkylene chain; provided that when E is a group of the formula,

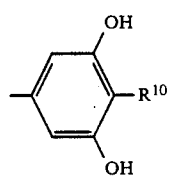

then A and D are each a heptamethylene group; l and m are each 1; B is a group of the formula —CH=CH—; $R^1$ is a methoxy group; $R^2$ is a hydrogen atom; and $R^3$ is a hydroxyl group; furthermore, when m is 1, then l is zero or 1; and when m is zero then l is zero], provided that, (i) when l is zero, then the sum of number of the carbon atoms in the alkylene groups of A and D is 1 to 12;

(ii) when B is a group of the formula —C≡C—, then
 (a) $R^1$ and $R^4$ should not be lower alkoxy groups,
 (b) $R^2$, $R^3$, $R^5$ and $R^6$ should not be hydrogen atoms, further,
 (c) A and D should not be heptamethylene groups, respectively;

(iii) when B is a group of the formula —CH=CH—, then
 (a) in the case of any one of $R^1$ and $R^4$ is a lower alkoxy group, then the other one should not be a lower alkoxy group, a hydroxyl group or a lower alkanoyloxy group,
 (b) in the case of any one of $R^2$ and $R^5$ is a hydrogen atom or a lower alkyl group, then the other one should not be a hydrogen atom,
 (c) in the case of any one of $R^3$ and $R^6$ is a hydroxyl group, a lower alkoxy group or a lower alkanoyloxy group, then the other one should not be a hydroxyl group or a lower alkanoyloxy group, further, (d) A and D should not be heptamethylene groups, respectively, or (2) the general formula (2),

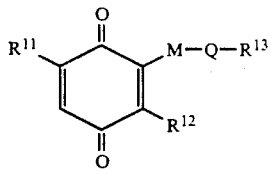 (2)

[wherein $R^{11}$ is a hydroxyl group or a lower alkoxy group; $R^{12}$ is a hydrogen atom, a hydroxyl group or a lower alkoxy group; $R^{13}$ is a hydrogen atom or an alkyl group having 1 to 8 carbon atoms; M is an alkylene group having 1 to 10 carbon atoms; Q is a group of the formula —CH=CH—, —C≡C—,

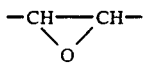

or —CH —CH$_2$—], provided that,
(i) when $R^{11}$ alkoxy group or a hydroxyl group, and $R^{12}$ is a hydroxyl group or a hydrogen atom, then a group of the formula —M—Q—$R^{13}$ should not be a n-pentyl group or a tridecanyl group, and
(ii) when $R^{11}$ is a lower alkoxy group and $R^{12}$ is a hydroxyl group, then a group of the formula —M—Q—$R^{13}$ should not be a 8-heptadecanyl group, or (3) the general formula (3)

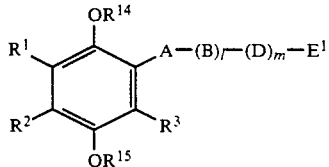 (3)

wherein $R^1$, $R^2$, $R^3$, A, B, D, l and m are the same as defined above; $R^{14}$ and $R^{15}$ are each a hydrogen atom, a methoxymethyl group or a lower alkanoyl group; $E^1$ is a group of the formula,

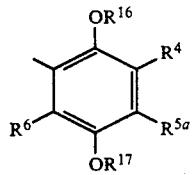

((wherein $R^4$ and $R^6$ are the same as defined above; $R^{16}$ and $R^{17}$ are each a hydrogen atom, a methoxymethyl group or a lower alkanoyl group; $R^{5a}$ is a hydrogen atom, a halogen atom, a lower alkoxycarbonyl group, a lower alkoxy group, a lower alkyl group, a lower alkylthio group, a hydroxy-lower alkyl group, a group of the formula —G—C≡C—$R^7$ (wherein G is a lower alkylene group; $R^7$ is a lower alkyl group), or a group of the formula,

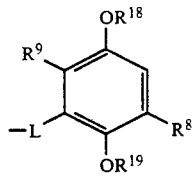

(wherein L, $R^8$ and $R^9$ are the same as defined above; $R^{18}$ and $R^{19}$ are each a hydrogen atom, a methoxymethyl group or a lower alkanoyl group))), or a group of the formula,

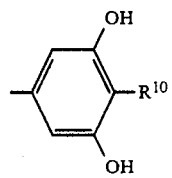

(wherein $R^{10}$ is the same as defined above)], provided that
(i) when l is zero, then alkylene groups having 1 to 10 carbon atoms represented by the symbols A and D may have an oxygen atom, sulfur atom or a group of the formula —S—S— as hetero atoms in the alkylene chain;
(ii) when the symbol E is a group of the formula

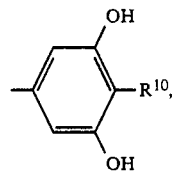

then A and D are heptamethylene groups, respectively, l is 1, m is 1, $R^1$ is a methoxy group, $R^2$ is a hydrogen atom, and $R^3$ is a hydroxyl group;
(iii) when m is 1, then l is zero or 1, and when m is zero, then l is zero; and
(iv) when l is zero, then the sum of number of the carbon atoms in the alkylene groups of A and D is 1 to 12;
(v) when B is a group of the formula —C≡C—, then
(a) $R^1$ and $R^4$ should not be lower alkoxy groups,
(b) $R^2$, $R^3$, $R^{5a}$ and $R^6$ should not be hydrogen atoms, further,
(c) A and D should not be heptamethylene groups, respectively;
(vi) when B is a group of the formula —CH=CH—, then
(a) in the case of any one of $R^1$ and $R^4$ is a lower alkoxy group, then the other one should not be a lower alkoxy group, a hydroxyl group or a lower alkanyloxy group,
(b) in the case of any one of $R^2$ and $R^{5a}$ is a hydrogen atom or a lower alkyl group, then the other one should not be a hydrogen atom,
(c) in the case of any one of $R^3$ and $R^6$ is a hydroxyl group, a lower alkoxy group or a lower alkanoyloxy group, then the other one should not be a hydroxyl group or a lower alkanoyloxy group, further, (d) A and D should not be heptamethylene groups, respectively, or (4) the general formula (4),

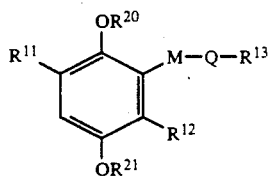 (4)

[wherein $R^{11}$, $R^{12}$, $R^{13}$, M and Q are the same as defined above; and $R^{20}$ and $R^{21}$ are each a hydrogen atom or a methoxymethyl group], provided that, (i) when $R^{11}$ is a lower alkoxy group or a hydroxyl group, and $R^{12}$ is a hydroxyl group or a hydrogen atom, then a group of the formula —M—Q—$R^{13}$ should not be a n-pentyl group or a tridecanyl group, and (ii) when $R^{11}$ is a lower alkoxy group and $R^{12}$ is a hydroxyl group, then a group of the formula —M—Q—$R^{13}$ should not be a 8-heptadecanyl group, or pharmaceutically acceptable salts thereof.

DESCRIPTION OF THE PRIOR ART

Asthma is a disease of a patient having hypersensitivity of bronchial airways, and is characterized by attacks of dyspnea due to increase in vascular permeability and mucous secretion, contraction of the bronchial smooth muscles due to reaction of the bronchial airways to inhaled or ingested allergens or non-specific stimulations (e.g., algor, ersiccation, exsication and the like).

At the present stage, certain types of therapies such as pharmacotherapy, therapy of change of air for health, desensitization therapy, psychotherapy and the like are singly or multiply conducted for treating and curing of asthma, but any effective curing method has not been established yet.

Among various kinds of antiasthmatic agents, beta-receptor stimulants, xanthine preparations, steroidal preparations, antihistaminic agents, chemical mediators releasing inhibitors and others are frequently used. However, working mechanisms of these antiasthmatic agents have not been studied well, and some of them are believed as follows. Thus, the beta-receptor stimulants may increase the enzymatic activity of adenylcyclase and change ATP (adenosine triphospate) to c-AMP (cyclic adenosine monophosphate) which possesses bronchodilation activity. The xanthine preparations may inhibit the enzymatic activity of phosphodiesterase which changes c-AMP to 5'-AMP having less bronchodilation activity, so as to perform bronchodilation. The antihistaminic agents antagonize the activity of histamine in the $H_1$-receptor, so that relieve the edema of the bronchial mucous membrane due to histamine-induced extravasation of blood plasma. The chemical mediators releasing inhibitors inhibit the asthmatic attack by controlling the releasing of chemical transmitter substances released from the mast cells. Various kinds of the above-mentioned antiasthmatic agents have their merits and demerits, and each one of them may not perform sufficient curing effects.

In the course of progress in the research and developments on antiasthmatic agents, there has been indentified slow reacting substance of anaphylaxis (hereinafter referred to as "SRS-A") which is believed as the major pathogenic substance of asthma, and is one of derivatives of arachidonic acid. [Cf. "KAGAKU-TOSEIBUTSU" (Chemistry & Biology) Vol. 20, No. 11, pp. 696-698 (1982); "TAISHA" (Metabolism), Vol. 18, No. 4, pp. 307-317 (1981); B. Samuelsson et al., Prostagrandins, Vol. 17, No. 6, pp. 785-787 (June 1979); R. C. Murphy et al., Proc. Natl. Acad. Sci. USA, Vol. 76, pp. 4275 (1979)].

"SRS-A" results edema and inflammation of bronchial mucous membrane and contraction of the bronchial smooth muscles which are the major symptoms of the asthma. [Cf. A. C. Peatfield et al., Brit. J. Pharmac. Vol. 77, pp. 391-393 (1982); M. C. Holroyde et al., Agents & Actions, Vol. 11, pp. 573-574 (1981); and Z. Marom et al., Amer. Rev. Respiratory Diseases, Vol. 126, pp. 449 (1982)].

As the results of extensive studies on antiasthmatic agents for curing and treating asthma, in consideration of the above-mentioned prior art situation, the present inventors have established an idea that "SRS-A" is bio-synthesized from arachidonic acid, and said biosynthesis reaction is related with an enzymatic activity of 5-lipoxygenase, in other words the formation of "SRS-A" can be controlled by inhibiting the enzymatic activity of said 5-lipoxygenase which will result the curing and treating of the asthma. As the results of studies for finding the substances which will inhibit the enzymatic activity of 5-lipoxygenase, the present inventors have found novel 1,4-benzoquinone derivatives and benzene derivative as well as their pharmaceutically acceptable salts represented by the general formulas (1) through (4) as mentioned above, which are quite useful as the inhibitor of enzymatic activity of 5-lipoxygenase, and by use of these newly found derivatives, the formation of "SRS-A" from arachidonic acid is controlled, so that various diseases such as asthma, inflammations, allergies and others caused by the formation of "SRS-A" can effectively be prevented and cured.

The 1,4-benzoquinone derivatives and benzene derivatives according to the present invention have only quite low toxicity, and possess cerebral- and cardiac-blood flow improving activity and preventive activity of cerebral ischema, and thus they are useful as activators for cardiac and cerebral metabolisms, curing agents for heart failure, cardiac and cerebral blood flow improving agents as well as for anti-allergic agents for slow reacting allergy (IV-type allergy).

SUMMARY OF THE INVENTION

An object of the present invention is to provide novel 1,4-benzoquinone derivatives and benzene derivatives represented by the general formulas (1)-(4) having useful pharmacological activities.

Another object of the present invention is to provide processes for preparing the above-mentioned 1,4-benzoquinone derivatives and benzene derivatives.

Further object of the present invention is to provide pharmaceutical compositions containing said 1,4-benzoquinone derivatives and/or benzene derivatives as the active ingredient.

DETAILED DESCRIPTION OF PREFERRED EMBODIMENTS 1,4-Benzoquinone derivatives and benzene derivatives represented by the general formulas (1) to (4) according to the present invention, examples of various substituents in the formulas are as follows.

As to the halogen atoms, chlorine atom, bromine atom, fluorine atom and iodine atom can be exemplified.

As to the lower alkylene group, an alkylene group having 1 to 6 carbon atoms, such as methylene, ethylene, trimethylene, tetramethylene, pentamethylene, hexamethylene, 2-methyltrimethylene, 1-methylethylene, 2,2-dimethyltrimethylene groups and others can be exemplified.

As to the lower alkyl group, an alkyl group having 1 to 6 carbon atoms, such as methyl, ethyl, n-propyl, isopropyl, n-butyl, tert-butyl, isobutyl, n-pentyl, neopentyl, isopentyl, 1,1-dimethylpropyl, 1,2-dimethylpropyl, n-hexyl, 1,2-dimethylbutyl, 4-methylpentyl groups and others can be exemplified.

As to the lower alkoxy group, an alkoxy group having 1 to 6 carbon atoms, such as methoxy, ethoxy, n-propoxy, isopropoxy, n-butoxy, tert-butoxy, isobutoxy, n-pentyloxy, neopentyloxy, isopentyloxy, 1,1-dimethylpropoxy, 1,2-dimethylpropoxy, n-hexyloxy, 1,2-dimethylbutoxy, 4-methylpentyloxy groups and others can be exemplified.

As to the lower alkanoyloxy group, an alkanoyloxy group having 1 to 6 carbon atoms, such as formyloxy, acetoxy, propionyloxy, n-butyryloxy, isobutyryloxy, valeryloxy, isovaleryloxy, pivaloyloxy, n-pentanoyloxy, n-hexanoyloxy groups and others can be exemplified.

As to the lower alkylthio group, an alkylthio group having 1 to 6 carbon atoms, such as methylthio, ethylthio, n-propylthio, isopropylthio, n-butylthio, isobutylthio, tert-butylthio, isopentylthio, n-hexylthio groups and others can be exemplified.

As to the hydroxy-lower alkyl group, a hydroxy-lower alkyl group having 1 to 6 carbon atoms, such as hydroxymethyl, 2-hydroxyethyl, 1-hydroxyethyl, 3-hydroxypropyl, 2-hydroxypropyl, 1-hydroxypropyl, 4-hydroxybutyl, 5-hydroxypentyl, 6-hydroxyhexyl groups and others can be exemplified.

As to the lower alkylene group, an alkylene having 1 to 10 carbon atoms, such as methylene, ethylene, trimethylene, tetramethylene, petamethylene, hexamethylene, heptamethylene, octamethylene, nonamethylene, decamethylene, 20methyltetramethylene, 3-ethylpetamethylene, 2,2-dimethyltrimethylene groups and others can be exemplified.

As to the lower alkoxycarbonyl group, an alkoxycarbonyl group having 1 to 6 carbon atoms in the alkoxy moiety, such as methoxy carbonyl, ethoxycarbonyl, propoxycarbonyl, isopropoxycarbonyl, butoxycarbonyl, tert-butoxycarbonyl, pentyloxycarbonyl, hexyloxycarbonyl groups and others can be exemplified.

The 1,4-benzoquinone derivatives and benzene derivatives according to the present invention can be prepared by chemical synthetic methods, and some of them can also be obtained by extracting from natural resources. There are various methods for preparing by chemical synthesis, and examples are shown as follows:

Reaction process formula-1 and reaction process formula-2 are reactions relating to oxidations of 1,4-hydroquinone for obtaining 1,4-benzoquinone derivatives. At the first, the methoxymethyl group which is the protecting group of monomer (7) and dimer (5) is removed by a method of common demethoxymethylation to obtaining hydroquinone derivative, and specifically, the reaction is carried out by an acid with monomer (7) and dimer (5) in a suitable organic solvent. As to the solvent used in this reaction, alcohols such as methanol, ethanol, isopropanol and others; ethers such as tetrahydrofuran, diethyl ether and others; saturated hydrocarbons such as cyclohexane, n-hexane and others; dichloromethane, acetonitrile and the like; and mixed solvents thereof can be exemplified. As to the acid used in this reaction, these known in the art can be selected from a wide range thereof, for example, mineral acids such as hydrochloric acid, hydrobromic acid, sulfuric acid; organic acids such as acetic acid, fluoroacetic acid, oxalic acid and others; Lewis acids such as boron trifluoride, aluminium chloride can be exemplified. The ratio of the amount of these acids to compound (5) or compound (7) may be at least an equimolar quantity to any one of compound (5) and (7).

The reaction may preferably be carried out in an inert gas, such as in argon gas or nitrogen gas. The reaction is generally carried out at a room temperature, and the reaction may be completed within 1 to 4 hours. Thus, 1,4-hydroquinone derivative of the general formula (6) and of the general formula (8) can be prepared.

Next, the oxidations of compound (6) or compound (8) as shown in reaction process formula-1 and -2 can be carried out in a suitable solvent. As to the organic solvent used in these reactions, those used in the above-mentioned demethoxymethylation can also be used. As to the oxidizing agents any known mild oxidizing agent can be selected from a wide range and used, for example, air, oxygen gas, manganese dioxide and others can be exemplified. The oxidation is carried out at a room temperature to about 60° C., preferably at a room temperature, and the reaction is carried out for 1 to 10 hours. Thus, the monomer of the general formula (2) and the dimer of the general formula (1) can be obtained.

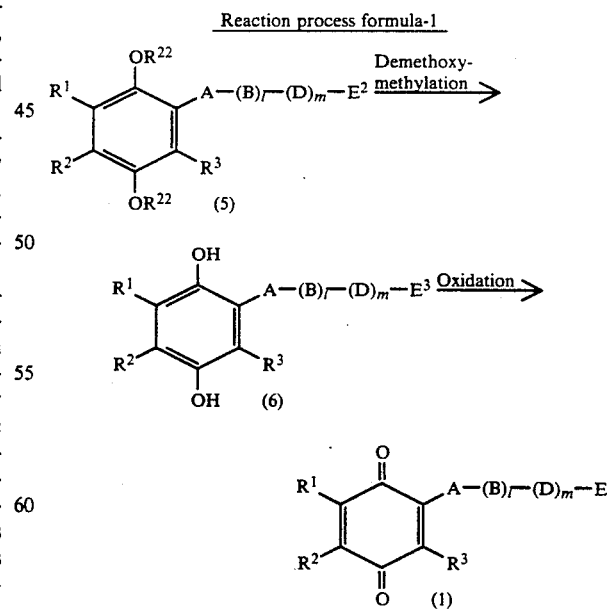

[wherein $R^1$, $R^2$, $R^3$, A, B, D, E, l and m are the same as defined above; $R^{22}$ is a methoxymethyl group; $E^2$ is a group of the formula,

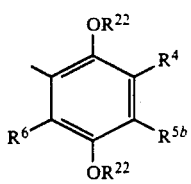

((wherein R⁴, R⁶ and R²² are the same as defined above; R⁵ᵇ is a hydrogen atom, a halogen atom, a lower alkyl group, a lower alkoxycarbonyl group, a lower alkoxy group, a lower alkylthio group, a hydroxy-lower alkyl group, a group of the formula —G—C≡C—R⁷ (wherein G and R⁷ are the same as defined above), or a group of the formula,

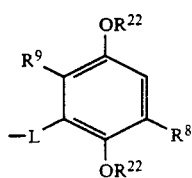

(wherein L, R⁸, R⁹ and R²² are the same as defined above))), or a group of the formula,

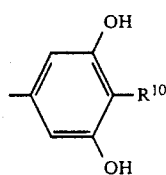

(wherein R¹⁰ is the same as defined above); E³ is a group of the formula,

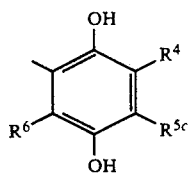

(wherein R⁴ and R⁶ are the same as defined above; R⁵ᶜ is a hydrogen atom, a halogen atom, a lower alkyl group, a lower alkoxy group, a lower alkoxycarbonyl group, a lower alkylthio group, a hydroxy-lower alkyl group, or a group of the formula —G—C≡C—R⁷ (wherein G and R⁷ are the same as defined above), or a group of the formula

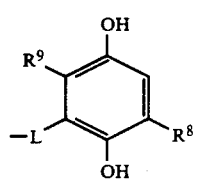

(wherein L, R⁸ and R⁹ are the same as defined above))); or a group of the formula,

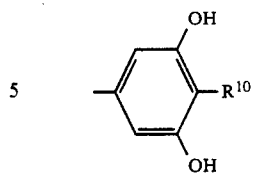

(wherein R¹⁰ is the same as defined above)].

Reaction process formula-2

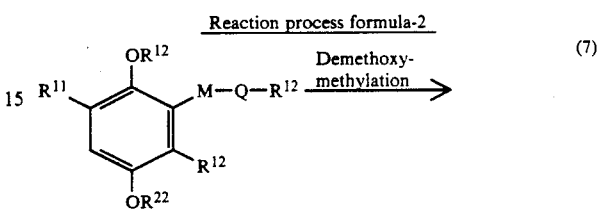  (7)

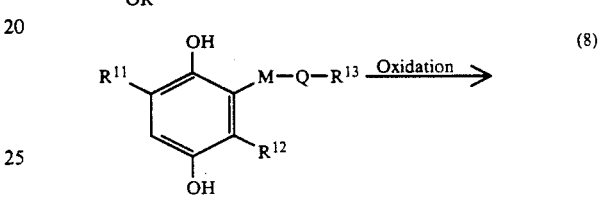  (8)

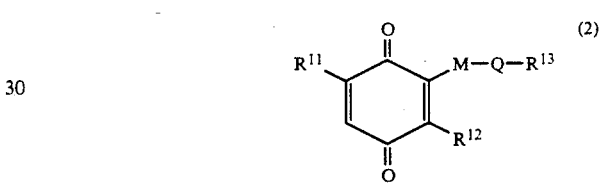  (2)

[wherein R¹¹, R¹², R¹³, R²², M and Q are the same as defined above.].

Compound (5) and compound (7) as the starting materials in the reaction process formula-1 and -2 are novel compounds, and they can be prepared easily by the following reaction process formulas.

Reaction process formula-3A

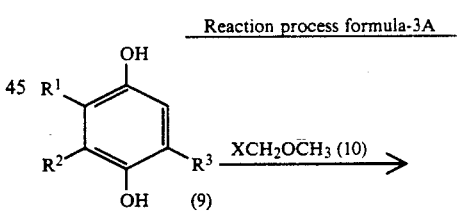

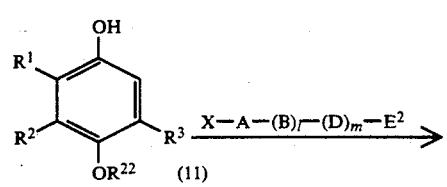

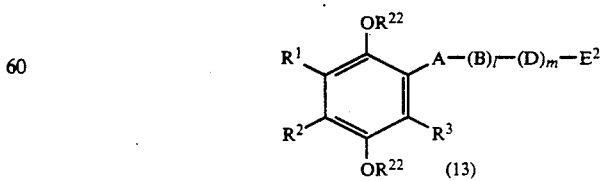

[wherein R¹, R², R³, A, B, D, l and m are the same as defined above; R²² is a methoxymethyl group; X is a halogen atom; E² is a group of the formula

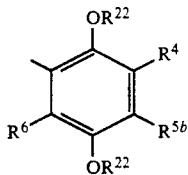

or a group of the formula,

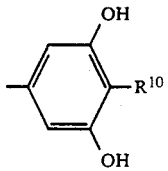

(wherein $R^{22}$, $R^4$, $R^{5b}$, $R^6$ and $R^{10}$ are the same as defined above)].

Reaction process formula-3B

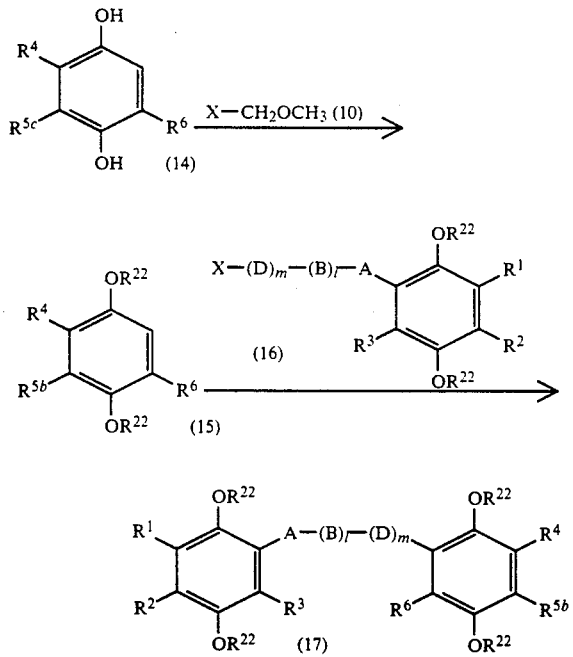

[wherein $R^1$, $R^2$, $R^3$, $R^4$, $R^6$, $R^{22}$, A, B, X, D, l, m, $R^{5b}$ and $R^{5c}$ are the same as defined above].

In the reaction process formula-3A, the reaction of compound (9) with compound (10) is carried out in a suitable inert solvent, in the presence of a basic compound at a room temperature to 100° C. for 30 minutes to 6 hours. As to the solvent used in this reaction, any common solvent can be used, for example, ethers such as tetrahydrofuran, dioxane, diethyl ether and others; saturated hydrocarbons such as cyclohexane, n-hexane and others; halogenated hydrocarbons such as methylene chloride and others; ketones such as acetone and others; aromatic hydrocarbons such as benzene and others; polar solvents such as hexamethylphosphoryl triamide and others can be exemplified. As to the basic compounds used in the reaction, hydroxide such as sodium hydroxide, potassium hydroxide and others; carbonates such as sodium carbonate, potassium carbonate, sodium hydrogen carbonate and others; alkali metal hydrides such as sodium hydride, potassium hydride and others; alkali metals such as metallic sodium, metallic potassium and others; alcoholates such as sodium methylate, potassium ethylate and others; amines such as pyridine, triethylamine and others can be exemplified. The ratio of the amount of compound (10) and the basic compound are at least an equimolar quantity, preferably 1 to 1.5 times the molar quantity per one hydroxyl group of compound (9) may be used.

The reaction of compound (11) with compound (12) is carried out in the presence of a strong basic compound, in a suitable inert solvent. As to the solvents used in the reaction, ethers such as tetrahydrofuran, diethyl ether and others; saturated hydrocarbons such as cyclohexane, n-hexane and others; polar solvents such as ammonia, hexamethylphosphoryl triamide and others can be examplified. The reaction is carried out, preferably by dissolving compound (11) in an organic solvent, then the solution is cooled to −30° to −100° C., next a strong basic compound is added dropwise to this solution by taking a time for about 10 minutes to 3 hours to obtain an organic metal compound of compound (11). As to the strong basic compound used in this reaction, alkyl metal basic compounds such as sec-butyllithium, tert-butyllithium, n-butyllithium-N,N,N',N'-tetramethylethylenediamine and others; metal hydride such as sodium hydride; alkali metals such as metallic sodium, metallic lithium and others can be exemplified. The ratio of the amount of these strong basic compound to the amount of compound (11) is at least an equimolar quantity, preferably an equimolar quantity to 2 times the molar quantity to the latter may be used. The ratio of the amount of compound (12) to the amount of compound (11) is at least an equimolar quantity, preferably 1.5 to 2 times the molar quantity of the former is used to the latter, and the reaction is carried out at −78° C. to 60° C., preferably at −78° C. to a room temperature for 2 to 20 hours with stirring condition. This reaction can advantageously be carried out in the presence of an alkali metal iodide such as sodium iodide, potassium iodide and others and/or hexamethylphosphoryl triamide. In the reaction process formula-3B, the reaction of compound (14) with compound (10), and the reaction of compound (15) with compound (16) are carried out under reaction conditions similar to those employed in the reaction of compound (9) with compound (10), and the reaction of compound (11) with compound (12) in the reaction process formula-3A. By the reaction process formula-3A and -3B, compound (13) and compound (17) can be obtained.

Reaction process formula-4

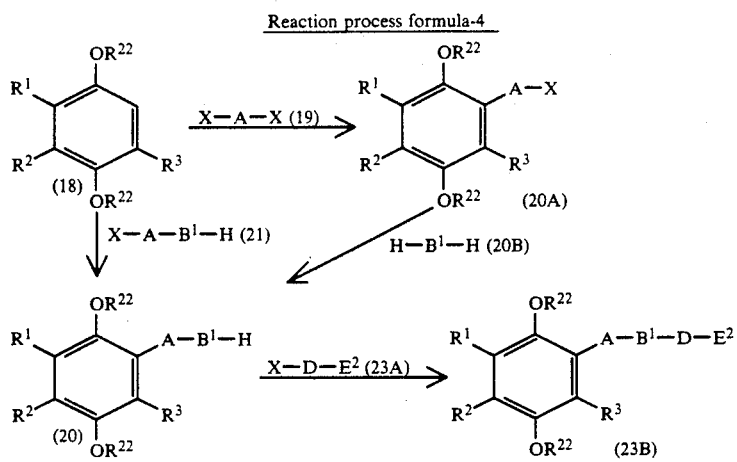

[wherein $R^1$, $R^2$, $R^3$, $R^{22}$, A, D, $E^2$ and X are the same as defined above; and $B^1$ is a group of the formula —C≡C—].

In the reaction process formula-4, the reaction of compound (18) with compound (19), and the reaction of compound (18) with compound (21) can be carried out under reaction conditions similar to those employed in the reaction of compound (11) with compound (12) in the reaction process formula-3A. The reaction of compound (20A) with compound (20B) is carried out in a suitable inert solvent, for example ethers such as tetrahydrofuran, diethyl ether and others; saturated hydrocarbons such as cyclohexane, n-hexane and others; polar solvents such as ammonia, hexamethylphosphoric triamide and others. Preferably, the reaction is conducted by dissolving compound (20B) in an anhydrous organic solvent, preferably in the stream of an inert gas such as argon gas, and the solvent is cooled below 0° C., then a strong basic compound is added dropwise to the solution in about 10 minutes to 3 hours with stirring to obtain an alkali metal compound of compound (20B). As to the strong basic compound used in this reaction, any strong basic compound employed in the reaction for obtaining compound (20A) from compound (18), and the amount of said strong basic compound is also similar to that employed in the reaction for obtaining compound (20A). Next, to the thus obtained reaction mixture was added dropwise a solution of compound (20A) dissolved in the same organic solvent used in the reaction mixture of compound (20B), and the whole mixture was stirred at a room temperature to 60° C., preferably at a room temperature for 1 to 6 hours. In this case, the reaction is advantageously be carried out in the presence of hexamethylphosphoric triamide in the reaction system. Compound (22) can thus be obtained.

The reaction for obtaining compound (23B) by reacting compound (22) with compound (23A) can be carried out under conditions similar to those employed in the reaction of compound (20A) with compound (20B to prepare compound (22).

Reaction-process formula-5

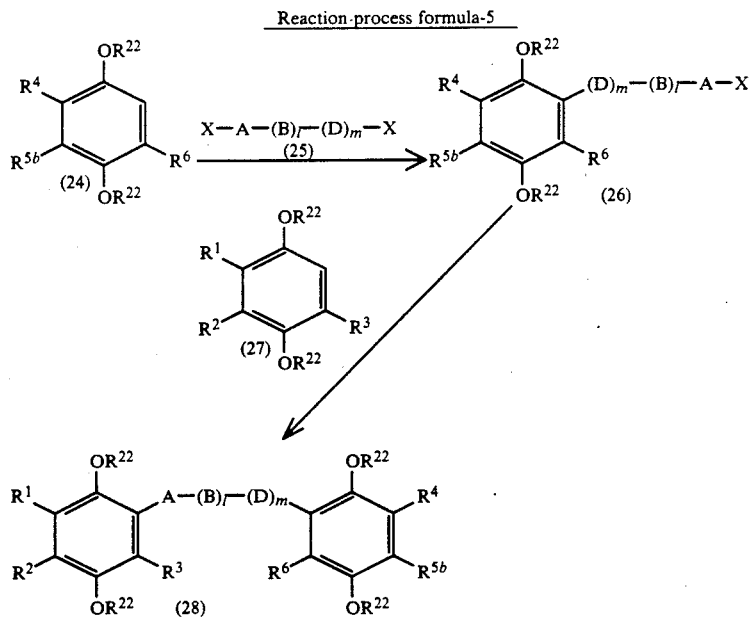

[wherein $R^1$, $R^2$, $R^3$, $R^4$, $R^{5b}$, $R^6$, A, B, D, l, m, $R^{22}$ and X are the same as defined above].

In the reaction process formula-5, the reaction of compound (24) with compound (25), and the reaction of compound (26) with compound (27) can be carried out under conditions similar to those employed in the reaction of compound (11) with compound (12) in the reaction process formula-3A.

Reaction process formula-6

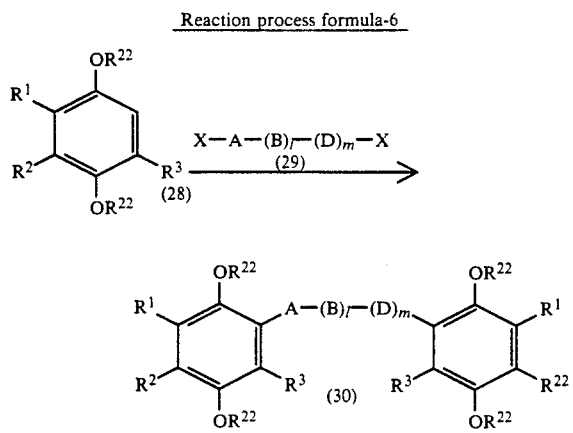

[wherein $R^1$, $R^2$, $R^3$, A, B, D, l, m and X are the same as defined above].

In the reaction process formula-6, the reaction of compound (28) with compound (29) can be carried out under reaction conditions similar to those employed in the reaction of compound (11) with compound (12) in the reaction process formula-3A, except that the ratio of the amount of the compound (28) and the amount of the strong basic compound to the amount of compound (29) is at least 2 times the molar quantity, preferably 2 to 4 times the molar quantity of compound (29).

Reaction process formula-7

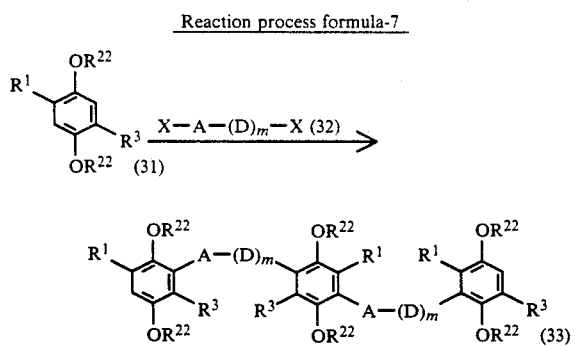

[wherein $R^1$, $R^3$, $R^{22}$, A, D, m and X are the same as defined above].

In the reaction process formula-7, the reaction of compound (31) with compound (32) can be carried out under reaction conditions similar to those employed in the reaction of compound (11) with compound (12) in the reaction process formula-3A, except that the ratio of the amount of the compound (31) and the amount of the strong basic compound to the amount of compound (32) is at least 3 times the molar quantity, preferably 3 to 6 times the molar quantity of compound (32).

Reaction process formula-8

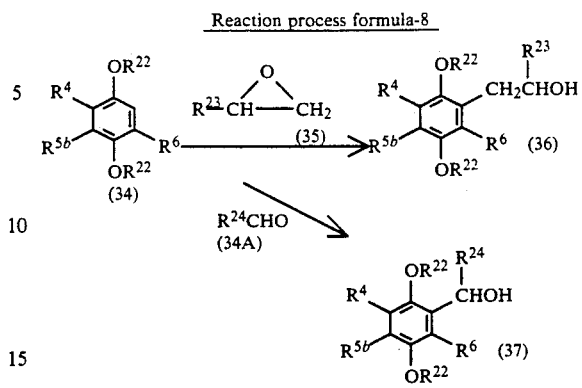

[wherein $R^4$, $R^{5b}$, $R^6$ and $R^{22}$ are the same as defined above, and $R^{23}$, $R^{24}$ are each a hydrogen atom or a lower alkyl group].

In the reaction process formula-8, the reaction of known compound (34) with ethylene oxide (35) for obtaining alcohol (36) is carried out by first dissolving compound (34) in an organic solvent for example ethers such as tetrahydrofuran, diethyl ether or the like; saturated hydrocarbon such as cyclohexane, n-hexane or the like; polar solvent such as ammonia, hexamethylphosphoric triamide or the like, preferably in an anhydrous organic solvent, and preferably the solution is cooled to $-30°$ to $-100°$ C., then a strong base is added dropwise to this solution in about 10 minutes to 3 hours to obtain an organometallic compound of compound (34). As to the strong base used in this reaction, alkyl metals such as sec-butyllithium, tert-butyllithium and others; alkyl metal salts such as n-butyllithium-N,N,N',N'-tetramethylenediamine; alkali metal or alkali metal compounds such as sodium hydride, metallic sodium, metallic lithium and others can be exemplified. The strong base is used at least an equimolar quantity, preferably an equimolar quantity to 2 times the molar quantity to compound (34). Next, at least an equimolar quantity, preferably 1.5 to 2.0 times the molar quantity of ethylene oxide (35) is added to the organometallic compound of compound (34) to obtain compound (36). This reaction is carried out at a room temperature to 60° C., preferably at a room temperature with stirring for 2 to 20 hours.

In the above-mentioned reaction, the reaction can advantageously be carried out by adding 0.1 molar quantity of boron trifluoride-ether to compound (34) with acceleration of the reaction velocity. Further, the reaction can also be carried out by adding hexamethylphosphoric triamide in the reaction system.

In the reaction for obtaining compound (37) from compound (34), alcohol (37) can be prepared by using aldehyde (34A) in place of epoxy compound (35) used in the reaction for obtaining compound (36) from compound (34).

Reaction process formula-9

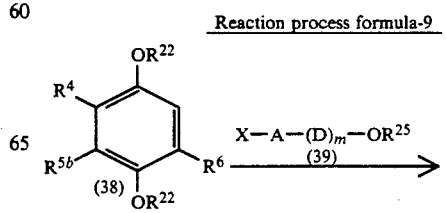

-continued
Reaction process formula-9

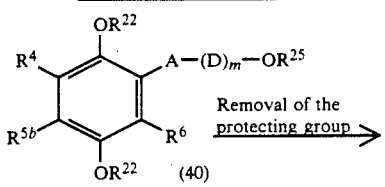

Removal of the protecting group →

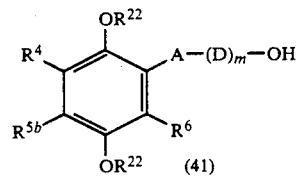

[wherein $R^4$, $R^{5b}$, $R^6$, $R^{22}$, m, A, D and X are the same as defined above; and $R^{25}$ is a benzyl group or a tri (lower alkyl)silyl group].

In the reaction process formula-9, the reaction of compound (38) with a halogenated ether compound (39) to obtain compound (40) can be carried out by using compound (39) in place of ethylene oxide used in the reaction of compound (34) for obtaining compound (36) in the reaction process formula-8, except that boron trifluoridediethyl ether is not employed.

Among the compounds represented by the general formula (40), those having tri (lower alkyl)silyl group is react with tetra-n-butylammonium fluoride in an inert solvent, preferably in the stream of inert gas, such as argon gas or nitrogen gas, generally at a room temperature for 30 minutes to 2 hours to obtain an alcohol (41).

The ratio of the amount of tetra-n-butylammonium fluoride to the amount of tri (lower alkyl)silyl derivative of compound (40) is 1.0 to 1.5 molar quantity to the latter.

Among compounds (40), those having benzyl group as to the symbol $R^{25}$ can be catalytically reduced in an inert solvent such as alcohols, ethers, esters, in the presence of a catalyst such as palladium-charcol or the like, under 1 atmospheric pressure of hydrogen gas to obtain compound (41) as in the form of alcohol compound.

Reaction process formula-10

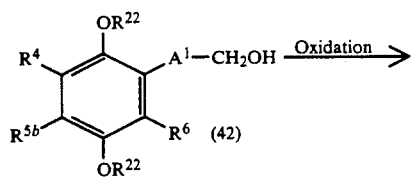

Oxidation →

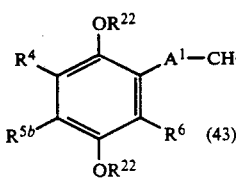

[wherein $R^4$, $R^{5b}$, $R^6$ and $R^{22}$ are the same as defined above; and $A^1$ is an alkylene group having 1 to 12 carbon atoms].

Reaction process formula-11

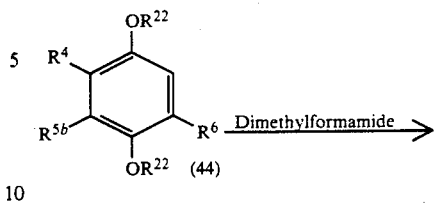

Dimethylformamide →

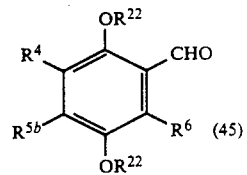

[wherein $R^4$, $R^{5b}$, $R^6$ and $R^{22}$ are the same as defined above].

By oxidation of alcohols (36), (37), (41) and (42) respectively prepared in reaction process formula-8, -9 and -10, the corresponding carbonyl derivatives can be obtained.

In the reaction process formula-10, the oxidation is carried out by reaction of compound (42) with an oxidizing agent in an inert solvent mentioned above at 0° C. to a room temperature for about 30 minutes to 2 hours. As to the oxidizing agent used in this reaction, pyridinium chlorochromate and others can be exemplified. The ratio of the amount of the oxidizing agent to 1 mole of compound (42) may be 2 to 10 times the molar quantity. The corresponding aldehyde (43) can be thus prepared.

Reaction process formula-11 is a reaction for obtaining the corresponding benzaldehyde (45) directly from compound (44). Thus, the benzaldehyde (45) can be prepared by reaction of compound (44) with a strong base in an inert solvent under an inert gas stream to obtain the organometallic compound of compound (44), next N,N-dimethylformamide (DMF) is reacted therewith at −30° to −100° C. for 2 to 6 hours to obtain the benzaldehyde (45). This reaction can be carried out under conditions similar to those employed in the reaction for obtaining compound (36) from compound (34) in the reaction process formula-8, except that DMF is used in place of ethylene oxide used therein. The ratio of the amount of DMF used to 1 mole of compound (34) may be at least an equimolar quantity, preferably 1.2 to 1.5 times the molar quantity.

Reaction process formula-12

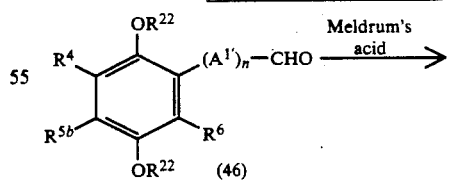

Meldrum's acid →

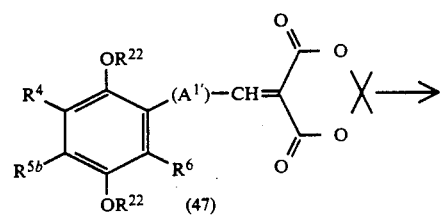

-continued
Reaction process formula-12

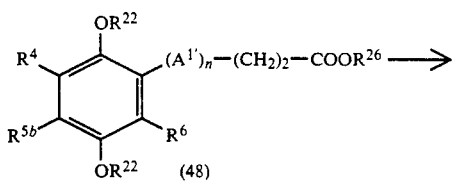
(48)

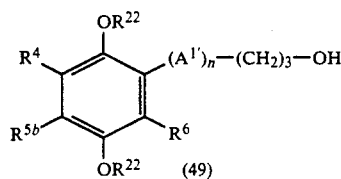
(49)

wherein $R^4$, $R^{5b}$, $R^6$ and $R^{22}$ are the same as defined above; n is zero or 1; $R^{26}$ is a lower alkyl group; and $A^{1'}$ is an alkylene group having 1 to 9 carbon atoms].

The carbonyl compounds prepared in the reaction process formula-10 and -11 can be treated by a method in reaction process formula-12 for the purpose of increasing the number of carbon atoms in the side chain. This reaction is an example of the reactions for increasing the number of carbon atoms in the carbon chain, and any reaction used for this purpose can be applied. For example, there is known a method for reaction of an aldehyde body (46) with an ester of malonic acid, or a method for reaction of an aldehyde (46) with a Witting reagent. Reaction process formula-12 shows the former method. Thus, compound (47) can be prepared by reaction of compound (46) with Meldrum's acid (2,2-dimethyl-1,3-dioxane-4,6-dione) in an inert solvent, such as a halogenated hydrocarbon, in the presence of a base, such as pyridine, triethylamine or the like, at a reaction temperature condition about a room temperature to 100° C. for 0.5 to 2 hours. The ratio of the amount of Meldrum's acid to 1 mole of compound (46) is at least an equimolar quantity, preferably 1.2 to 1.5 times the molar quantity.

The compound (47) thus prepared reacts with a reducing agent, such as sodium borohydride in an alcohol solvent, such as methanol to give a compound in which the carbon-carbon double bond is reduced. Decarboxylation of said reduced compound in the presence of a metallic catalyst, such as copper powder in a mixed solvent of an alcohol, such as ethanol with a basic solvent such as pyridine at a temperature condition about 80° to 150° C., for 5 to 15 hours by heating give a compound (48).

Then compound (48) reacts with a reducing agent, such as lithium aluminium hydride in an inert solvent as mentioned above, such as tetrahydrofuran, to give an alcohol (49).

The alcohol (49) is then oxidized by a method similar to that described in the above-mentioned reaction process formula-10 to convert into an aldehyde, then similar procedure is again conducted to obtain an alcohol body compound having longer side chain in which the number of carbon atoms is increased.

A method for obtaining a halide (51) from an alcohol (50) is shown in reaction process formula-13 as follows.

Reaction process formula-13

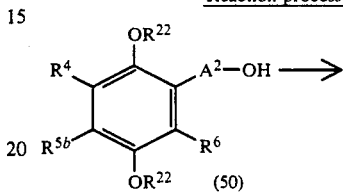
(50)

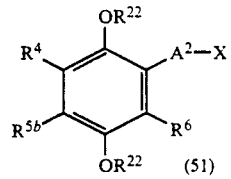
(51)

[wherein $R^4$, $R^{5b}$, $R^6$, $R^{22}$ and X are the same as defined above; and $A^2$ is an alkylene group having 1 to 12 carbon atoms].

In reaction process formula-13, an alcohol (50) is reacts with a halogenated alkylsulfonyl compound in the above-mentioned inert solvent, especially in a halogenated hydrocarbon such as dichloromethane or the like; an ether or a saturated hydrocarbon solvent, in the presence of a basic compound, at 0° C. to about a room temperature for 5 to 10 hours to give an intermediate in which the hydroxyl group is substituted with an alkylsulfonyl group. Then said alkylsulfonylated compound reacts with an alkali metal halogenide to obtain a halogenated compound (51). As to the halogenated alkylsulfonyl compound used in this reaction, a lower alkanesulfonyl halide, such as methanesulfonyl chloride, ethanesulfonyl chloride and others, an aromatic sulfonyl halide such as benzenesulfonyl chloride, p-toluenesulfonyl chloride or the like may be exemplified. As to the base used in this reaction, a tri-lower alkylamine such as triethylamine or the like; or an aromatic amine such as pyridine or the like may be exemplified. As to the alkali metal halide, sodium iodide, potassium iodide, lithium bromide, lithium chloride or the like may be exemplified. The ratio of the amount of the halogenated alkylsulfonyl compound to 1 mole of compound (50) may be 1.2 to 1.5 times the molar quantity, and the ratio of the amount of the alkali metal halogenide to 1 mole of compound (50) may be 1.2 to 2.0 times the molar quantity.

Reaction process formula-14

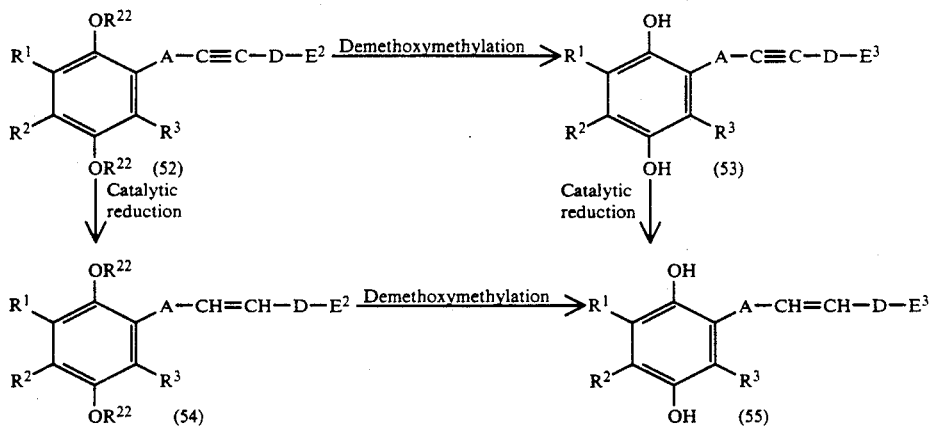

[wherein $R^1$, $R^2$, $R^3$, $R^{22}$, A, D, $E^2$ and $E^3$ are the same as defined above].

Reaction process formula-15

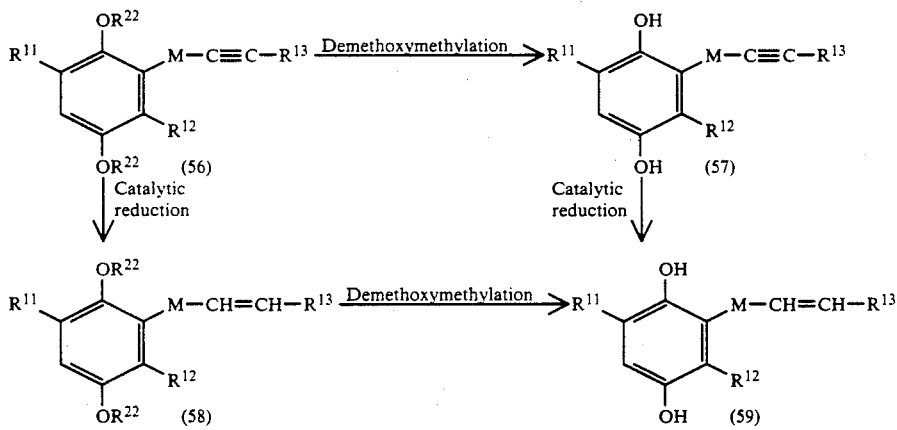

[wherein $R^{11}$, $R^{12}$, $R^{13}$, $R^{22}$ and M are the same as defined above ].

As shown in reaction process formula-14 and -15, the reactions for obtaining compounds (54), (55), (58) and (59) by reducing catalycally each of compounds (52), (53), (56) or (57) can be carried out in the presence of a suitable catalyst in an organic solvent. As to the catalyst used in this reaction, any known catalyst which can be able to reduce the triple carbon-carbon bond in the starting material to the corresponding double bond can be selected from a wide range and can be used. Specifically, Lindlar catalyst, palladium-barium sulfatequinoline catalyst and others can be exemplified. As to the solvent used in this reaction, alcohols such as methanol, ethanol and others; esters of acetic acid such as ethyl acetate and others; and ethers such as tetrahydrofuran, diethyl ether and others can be exemplified.

The reaction can preferably be carried out in hydrogen gas stream under an atmospheric pressure, at 0° C. to about a room temperature, and the reaction is completed in about 1 to 6 hours.

The demethoxymethylation of compounds (52), (54), (56) or (58) can be carried out under conditions similar to those employed in the demethoxymethalation of compound (5) in reaction process formula-1.

Reaction process formula-16

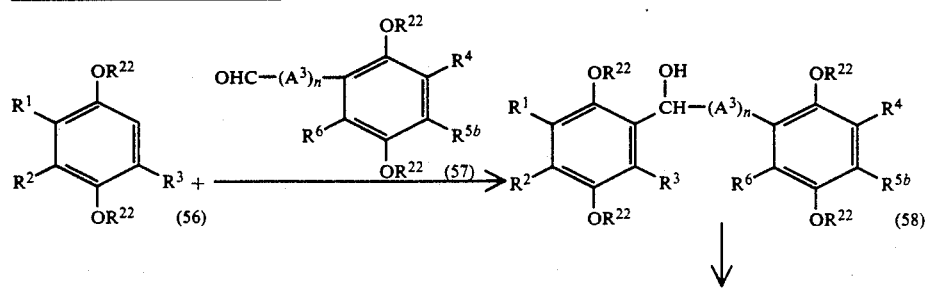

Reaction process formula-16

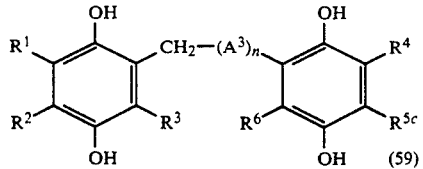

[wherein $R^1$, $R^2$, $R^3$, $R^4$, $R^{5b}$, $R^{5c}$, $R^6$ and $R^{22}$ are the same as defined above; $A^3$ is an alkylene group having 1 to 11 carbon atoms; and n is zero or 1].

Reaction process formula-16 is a reaction for preparing compound (58) by using compound (56) and (57) as the starting materials. Thus, compound (58) can be prepared by reaction of compound (56) with compound (57) under conditions similar to those employed in the reaction of compound (34) with compound (34A) in reaction process formula-8.

Next, the thus obtained compound (58) reacts in an inert solvent as mentioned above, such as methylene chloride, or without the solvent, in the presence of an acid with a reducing agent at 0° C. to a room temperature for 1 to 5 hours to give parahydroquinone (59) in which the hydroxyl groups are removed reductively, and at the same time the protective groups of $R^{22}$ are removed. As to the reducing agent used in this reaction, triethylsilane and others can be exemplified.

Reaction process formula-17

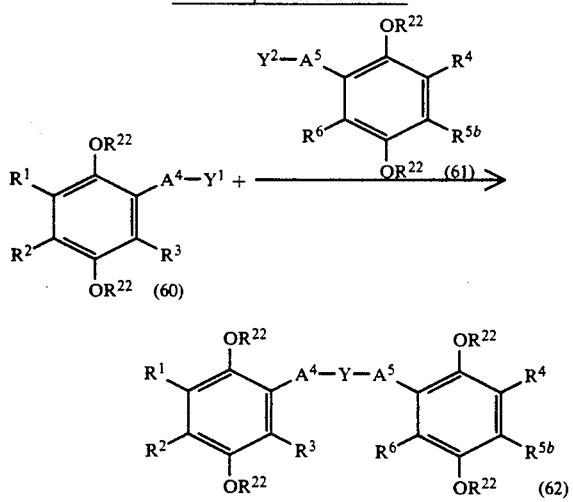

[wherein $R^1$, $R^2$, $R^3$, $R^4$, $R^{5b}$, $R^6$ and $R^{22}$ are the same as defined above; either one of $Y^1$ and $Y^2$ is a hydroxyl group or a group of the formula —SH, or another one is a halogen atom; and $A^4$ and $A^5$ are each an alkylene group having 1 to 10 carbon atoms].

Reaction process formula-17 is a reaction for obtaining compound (62) from compound (60) and compound (61) as the starting materials. Thus, compound (62) can be prepared by reaction of compound (60) with compound (61) in the presence of a base at a room temperature to 120° C., for about 0.5 to 6 hours. As to the base used in this reaction, sodium hydride, potassium hydride, metallic sodium, metallic potassium and others can be exemplified. The ratio of the amount of compound (61) to 1 mole of compound (60) may be 1.0 to 1.2 times the molar quantity of the latter, and the ratio of the amount of the base may be 1.0 to 1.2 times the molar quantity of the latter.

Reaction process formula-18

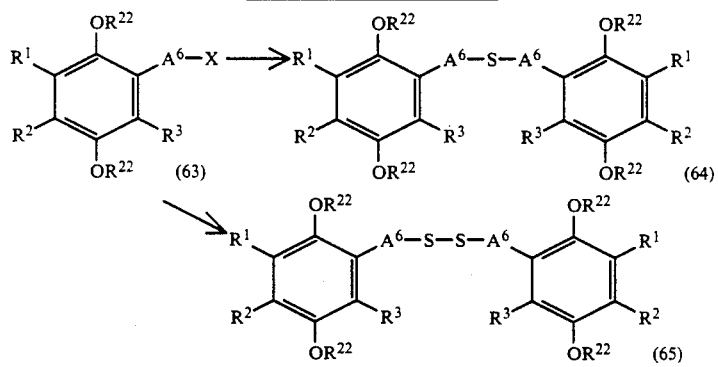

[wherein $R^1$, $R^2$, $R^3$ and $R^{22}$ are the same as defined above; and $A^6$ is an alkylene group having 1 to 6 carbon atoms].

Reaction process formula-18 is a reaction for obtaining compound (64) or (65) from compound (63) as the starting material.

Thus, compound (63) and sulfide dissolved in an inert solvent as mentioned above, such as ethanol or DMF, then said solution reacts at about a room temperature to 120° C. for 0.5 to 6 hours to give compound (64) and (65). As to the sulfide used in this reaction, sodium sulfide, potassium sulfide and others can be exemplified. When 1 mole of the sulfide is used to 1 mole of compound (63), then monosulfide compound (64) can be obtained as the major product, on the other hand, when 2 moles of the sulfide is used to 1 mole of compound (63), then disulfide compound (65) can be obtained as the major product.

Further, when about equimolar quantity each of compound (63) and compound (63A) represented by the following formula, $$E^2—D—X \quad (63A)$$

[wherein $E^2$, D and X are the same as defined above ], together with the sulfide react under conditions similar to those employed in the above-mentioned reaction, then the reaction products are separated, there are obtained symmetry and non-symmetry forms of compound (65) respectively.

Reaction process formula-19

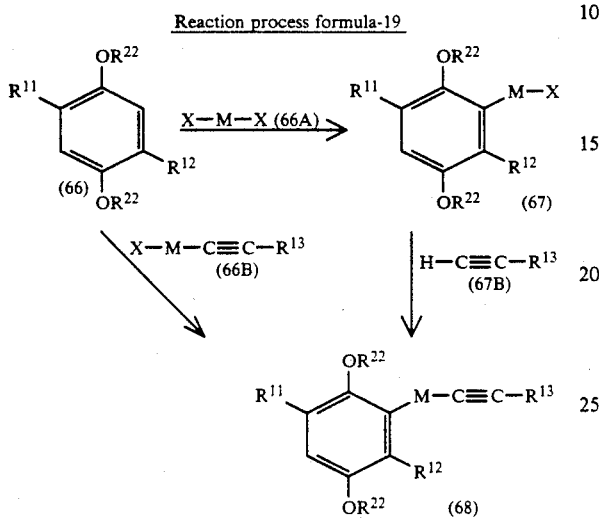

[wherein $R^{11}$, $R^{12}$, $R^{22}$, M, $R^{13}$ and X are the same as defined above].

In reaction process formula-19, the reaction for preparing compound (67) by reaction of compound (66) with compound (66A), the reaction for preparing compound (68) by reaction of compound (67) with an acetylene compound (67B), and the reaction for preparing compound (68) by reaction of compound (66) with an acetylene compound (66B) can be carried out under reaction conditions similar to those employed in reaction process formula-4.

Reaction process formula-20

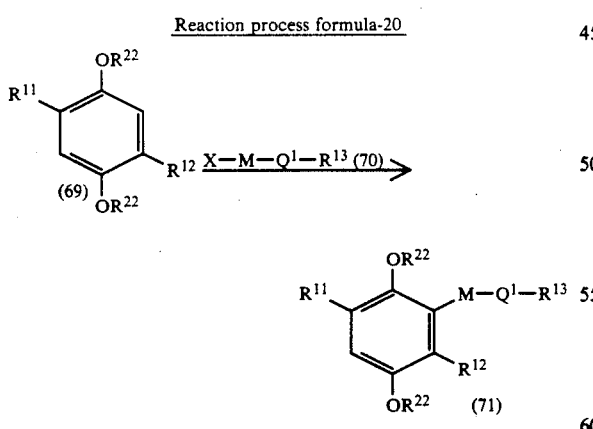

[wherein $R^{11}$, $R^{12}$, $R^{13}$, $R^{22}$, X and M are the same as defined above; and $Q^1$ is an ethylene group].

In reaction process formula-20, the reaction of compound (69) with compound (70) can be carried out under reaction conditions similar to those employed in the reaction of compound (11) with compound (12) in reaction process formula-3A.

Reaction process formula-21

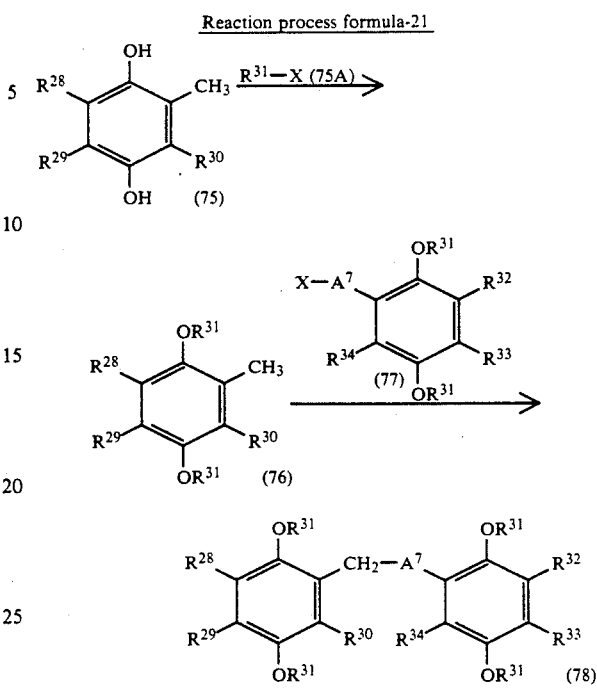

[wherein X is a halogen atom; $R^{28}$, $R^{29}$, $R^{30}$, $R^{32}$, $R^{33}$ and $R^{34}$ are each a lower alkyl group; $R^{31}$ is a methyl group or methoxymethyl group; and $A^7$ is an alkylene group having 1 to 11 carbon atoms].

In reaction process formula-21, the reaction of hydroquinone derivative (75) with compound (75A) can be carried out under conditions similar to those employed in the reaction for preparing compound (11) from compound (9) in reaction process formula-3A. Furthermore, the reaction of compound (76) with compound (77) can be carried out under conditions similar to those employed in the reaction of compound (11) with compound (12) in reaction process formula-3A.

Reaction process formula-22

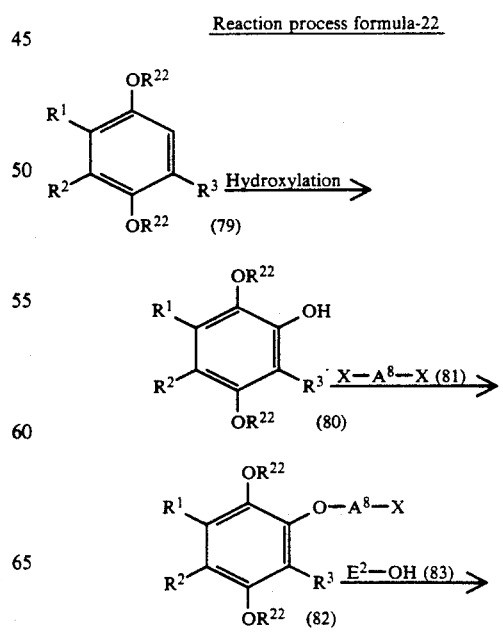

-continued

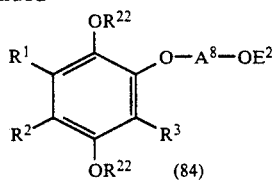

Reaction process formula-23

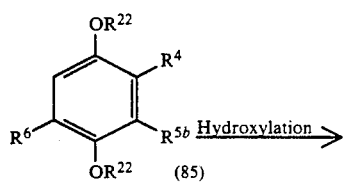

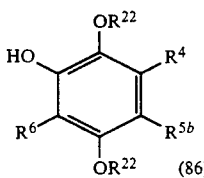

[wherein $R^1$, $R^2$, $R^3$, $R^4$, $R^{5b}$, $R^6$, $R^{22}$, X and $E^2$ are the same as defined above; and $A^8$ is an alkylene group having 1 to 12 carbon atoms].

In reaction process formula-22 and -23, the hydroxylation of compound (79) or compound (85) can be carried out under conditions similar to those employed in the reaction for obtaining the alkali metal compound of compound (11) in reaction process formula-3A, thus compound (79) or compound (85) is converted into the corresponding alkali metal compound, then oxidized with an organic peracid or oxygen gas to give the corresponding peroxide, next said peroxide is reduced with a reducing agent such as sodium bisulfite to give hydroxide (80) or (86) respectively.

The reaction of compound (8) with compound (81), and the reaction of compound (82) with compound (83) can be carried out under conditions similar to those employed in the reaction of compound (9) with compound (10) in reaction process formula-3A.

Reaction process formula-24

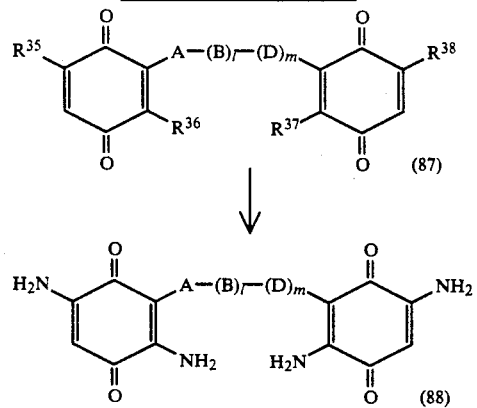

[wherein $R^{35}$, $R^{36}$, $R^{37}$, $R^{38}$ are each a lower alkoxy group; and A, B, D, l and m are the same as defined above].

In reaction process formula-24, compound (88) can be obtained by reaction of compound (87) with ammonia solution in an inert solvent, for example a lower alcohol such as methanol, ethanol or the like; an ether such as dioxane, tetrahydrofuran or the like; or other solvent, at a temperature of about 0° to 50° C., for 3 to 12 hours. The ratio of the amount of ammonia solution to compound (87) may be over 4 times the molar quantity.

Reaction process formula-25

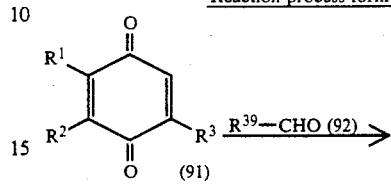

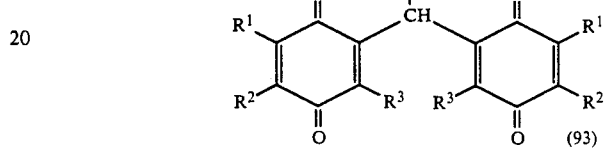

[wherein $R^1$, $R^2$, $R^3$ are the same as defined above; and $R^{39}$ is a hydrogen atom or an alkyl group having 1 to 11 carbon atoms].

In the reaction process formula-25, a known compound (91) reacts with an aldehyde (92) in an inert solvent mentioned-above, in the presence of acid catalyst at a temperature condition of about 0° to 100° C., for 5 minutes to 12 hours, to give compound (93) in which 2 molecules of compound (91) are combined through a group of the formula $$-\underset{R^{39}}{\overset{|}{CH}}-$$

is obtained.

As to the acid catalyst used in this reaction, organic acid such as acetic acid, formic acid, oxalic acid and others; inorganic acid such as hydrochloric acid, nitric acid, sulfuric acid and others can be exemplified.

The ratio of the amount of aldehyde (92) to 1 mole of compound (91) may be 0.2 to 1 molar quantity, preferably 0.3 to 0.5 molar quantity, and the ratio of the amount of the acid catalyst to 1 mole of compound (91) may be 0.1 to 1 molar quantity.

Among the desired products of the present invention and the starting materials, those having lower alkoxy group can be prepared by partially or completely alkylation of the hydroxyl group. As to the alkylating agent used in this reaction, lower alkyl halides, dilower alkyl sulfates, diazomethane and others can be exemplified.

In case of carrying out methylation by using diazomethane, a compound having hydroxyl group can be reacted with diazomethane in an inert solvent for example an ether such as dioxane, tetrahydrofuran, diethyl ether or the like, at a temperature condition of 0° C. to about a room temperature for 30 minutes to 2 hours. The ratio of amount of diazomethane may be an equimolar quantity, preferably 1 to 2 times the molar quantity to one hydroxyl group.

In case of carrying out alkylation by using a lower alkyl halide, the reaction can be carried out under conditions similar to those employed in usual dehydrohalogenating reaction. The above-mentioned reaction can be carried out under reaction conditions used in the reaction of compound (9) with compound (10) in reaction process formula-3A.

In case of carrying out alkylation by using a di-lower alkyl sulfate, the reaction can be carried out in an inert solvent at a temperature condition of 0° C. to about 60° C. for about 30 minutes to 6 hours with a di-lower alkyl sulfate. As to the di-lower alkyl sulfate used in this reaction, dimethyl sulfate, diethyl sulfate, di-n-propyl sulfate, di-n-butyl sulfate and others can be exemplified. The ratio of amount of the di-lower alkyl sulfate may be an equimolar quantity, preferably 1 to 2 times the molar quantity to one hydroxyl group.

By the above-mentioned alkylation, the reaction product in which the hydroxyl group is partially or completely alkylated can be obtained.

Among the desired products of the present invention and the starting materials, those having the hydroxyl groups on the 1,4-benzoquinone ring or/and on the phenyl ring can be prepared by partial or complete dealkylation of the lower alkoxy groups. The dealkylation reaction can be carried out in an inert solvent for example an alcohol such as methanol, ethanol or the like; an ether such as dioxane, tetrahydrofuran or the like, a halogenated hydrocarbon such as chloroform, methylene chloride or the like, in the presence of an acid catalyst, at room temperature to 100° C., for 30 minutes to 6 hours. As to the acid used in this reaction, mineral acids such as hydrochloric acid, hydrobromic acid, sulfuric acid or the like; Lewis acids such as boron tribromide, boron trichloride and others can be exemplified.

In case of partial dealkylation, the reaction can preferably be conducted in the presence of a Lewis acid. In case of using a mineral acid, the reaction time may preferably be shortened.

In case of using a Lewis acid, the ratio of amount of the Lewis acid to one alkoxy group in the starting material may be 0.2 to 0.5 times the molar quantity.

By the above-mentioned dealkylation, the reaction product in which the lower alkoxy groups are partially or completely dealkylated can be obtained.

The above-mentioned alkylation and dealkylation can be carried out repeatedly alone or in combination thereof.

Furthermore, among the desired products and the starting materials of the present invention, those having a group of the formula —CH=CH— or —C≡C— as for the symbol B or Q can be converted to compounds having a group of the formula —CH$_2$CH$_2$— by reduction. The reduction can be carried out under conditions similar to those employed in known reduction, preferably under reaction conditions similar to those employed in a catalytic reduction. As to the catalysts for reduction, those known in the art can be selected from a wide range and can be used, for example palladium-carbon, palladium, platinum, Raney-nickel and others can be exemplified. The ratio of amount of the catalyst is not specifically restricted, and is used in a catalytic amount. The reduction is carried out in a suitable solvent or without the solvent. As to the solvent, lower alcohols such as methanol, ethanol and others; esters such as ethyl acetate and others; lower fatty acids such as acetic acid and others can be exemplified. The reduction is carried out usually under a normal pressure to 10 atmospheric pressure of hydrogen gas (preferably under a normal pressure), at room temperature to 100° C. (preferably at room temperature), and the reaction is completed generally within 0.5 to 5–6 hours.

Among the desired products and the starting materials, those having a group of the formula

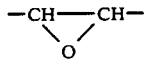

as for the symbols of B and Q can be prepared by an epoxidation of a corresponding compound having a group of the formula —CH=CH— as for the symbols of B and Q. The epoxidation is carried out by using a peracid. As to the peracid used in the epoxidation, those known in the art can be selected from a wide range, for example perbenzoic acid derivatives such as perbenzoic acid, m-chloroperbenzoic acid and others; peracetic acid derivatives such as peracetic acid-trifluoroperacetic acid and others; and an aqueous solution of hydrogen peroxide and others can be exemplified. The organic peracid is used at least in an equimolar quantity, preferably in an equimolar quantity to about 1.5 times the molar quantity to 1 mole of the starting materials. As to the solvent used in the epoxidation, halogenated hydrocarbons such as methylene chloride, chloroform, and others; ketones such as acetone and others; aromatic hydrocarbons such as benzene, toluene and others can be exemplified. The above-mentioned epoxidation is carried out generally at −20° to 50° C., preferably at 0° C. to room temperature, and the reaction is completed in about 1 to 20 hours. Thus obtained epoxy compound can be converted into a glycol derivative by hydrolysis so that the desired products and starting materials having group of the formula

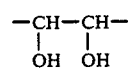

in the molecule are prepared.

Reaction conditions employed in hydrolysis of epoxide to obtain glycol may be applied to the abovementioned reaction, for example, the hydrolysis may be carried out in a suitable solvent in the presence of an acid. As to the acid used in the reaction, any acid which can be used in this type of hydrolysis can be exemplified, specifically, inorganic acids such as perchloric acid, hydrochloric acid, sulfuric acid and others can be exemplified. The amount of the acid used to the reaction is not specifically restricted and usual catalytic amount may be used.

Among the desired products and the starting materials according to the present invention, those having halogen atoms on the phenyl ring can also be prepared by halogenating substitution reaction in which the hydrogen atoms on the phenyl ring are converted into halogen atoms. Said halogen substitution is carried out in a suitable inert solvent with a strong base to prepare the corresponding organometallic compound, then a halogenating agent reacts therewith at a temperature range from −100° to 0° C. for 3 to 14 hours. As to the solvent, ethers such as dioxane, tetrahydrofuran and others; saturated hydrocarbons such as cyclohexane, n-hexane and others; polar solvents such as hexamethylphosphoric triamide and others can be exemplified. As to the strong base, alkyl metal base such as sec-butyllithium, tert-butyllithium, n-butyllithium-N,N,N',N'-tetramethylethylenediamine and others; alkali metals and alkali metal hydride such as sodium hydride, sodium metal, lithium metal and others can be exemplified. As to the halogenating agents, N-halogenosuccinimides such as N-bromosuccinimide, N-chlorosuccinimide, N-iodosuccinimide and others can be exemplified.

The amount of the halogenating agent and of the strong base are respectively 1 to 2 times the molar quantity to the starting materials in case of introducing one halogen atom. In case of introducing 2 or more number of halogen atoms, 2 times the molar quantity or more amount of the halogenating agent and of the strong base may be used as compared with the case of introducing one halogen atom.

Among the desired products and the starting materials according to the present invention, those having lower alkylthio groups on the phenyl rings can also be prepared by substituting lower alkylthio groups for the hydrogen atoms on the phenyl ring. Said substitution can be carried out under conditions similar to those employed in the above-mentioned halogenating substitution reaction, except that a compound represented by the general formula (94), $$R^{40}-S-S-R^{40} \quad (94)$$

[wherein $R^{40}$ is a lower alkyl group], is used in place of the halogenating agent.

Among the desired products and the starting material according to the present invention, those having lower alkoxycarbonyl groups on the phenyl ring can also be prepared by converting the hydrogen atoms on the phenyl ring into lower alkoxycarbonyl groups. Said reaction can be carried out under conditions similar to those employed in the above-mentioned halogen substitution, except that a compound represented by the general formula (95),

(95)

[wherein $R^{41}$ is a lower alkyl group; and X is the same as defined above], is used in place of the halogenating agent.

Among the desired products and the starting materials according to the present invention, those having lower alkanoyloxy groups can also be prepared by converting the hydroxyl groups into lower alkanoyloxy groups. The reaction can be carried out in a suitable inert solvent, for example a halogenated hydrocarbon such as dichloroethane, chloroform or the like; an ether such as dioxane, tetrahydrofuran or the like; a polar solvent such as pyridine or the like, by reacting with a lower alkanoylating agent, in the presence of a base room temperature to about 50° C. for about 1 to 10 hours. As to the base used in this reaction, those used as deacidifying agents for example tertiary amines such as diisopropylethylamine, triethylamine, pyridine and others; base such as sodium hydrogen carbonate, sodium acetate, potassium acetate and others can be exemplified. As to the lower alkanoylating agents used in this reaction, lower alkanoyl halides, lower alkanoic acid anhydrides and others can be exemplified. The ratio of amount of the lower alkanoylating agent may be at least an equimolar quantity, preferably 1 to 3 times the molar quantity to one hydroxyl group in the starting material.

Among the desired products and the starting materials according to the present invention, those having hydroxy-lower alkyl groups on the phenyl ring can also be prepared by first reacting a corresponding compound having hydrogen atoms on the phenyl ring with a compound represented by the general formula (96), $$X-Z^1-O-Z^2 \quad (96)$$

[wherein X is a halogen atom, $Z^1$ is a lower alkylene group, and $Z^2$ is a protecting group], then the protecting group is removed from the reaction product. The reaction can be carried out under conditions similar to those employed in the reaction of compound (11) with compound (12) in reaction process formula-3A. As to the protecting group, tetrahydropyranyl group and others can be exemplified. The above-mentioned reaction for removal of the protecting group can be carried out under conditions similar to those employed in the demethoxymethylation in reaction process formula-1.

When any protecting group is required to a compound having hydroxy-lower alkyl group as mentioned above for the purpose of using such compound in various reactions, the above-mentioned demethoxymethylation may not be conducted and such compound may be used to the desired reaction, or may be supplemented another suitable protecting group newly upon request.

Among the desired products and the starting material according to the present invention, those having lower alkyl groups on the phenyl ring can be prepared by reaction of a corresponding compound having hydrogen atoms on the phenyl ring with a lower alkyl halide. The reaction can be carried out under conditions similar to those employed in the reaction of compound (11) with compound (12) in reaction process formula-3A.

Using a compound represented by the general formula (97), $$X-G-C\equiv C-R^7 \quad (97)$$

wherein X, G and $R^7$ are the same as defined above, in place of the above-mentioned lower alkyl halide, under conditions similar to those used in the above reaction, among the desired products and the starting materials according to the present invention those having a group of the formula $-G-C\equiv C-R^7$ can be prepared Furthermore, using a compound represented by the general formula (98),

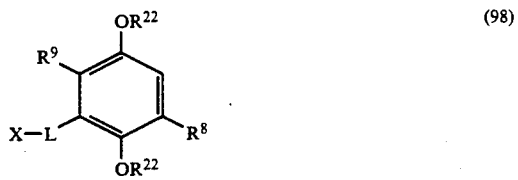

(98)

[wherein X, L, $R^8$, $R^9$ and $R^{22}$ are the same as defined above], in place of the above-mentioned lower alkyl halide, under conditions similar to those used in the above reaction, among the desired products and the starting materials according to the present invention those having a group of the formula

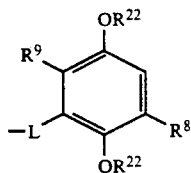

can be prepared.

In carrying out the above-mentioned reactions, when a compound having hydroxyl groups or amino groups is used, the hydroxyl groups or amino groups may be first protected with protecting groups similar to those generally employed in these type of reactions, then such protecting groups are removed from the protected groups.

As to the protecting groups for hydroxyl group, methoxymethyl group, tetrahydropyranyl group, benzyl group, tri(lower alkyl)silyl group and others can be exemplified, further as to the protecting groups for amino group, tert-butoxycarbonyl group, benzyloxycarbonyl group and others can be exemplified.

In case of introducing methoxymethyl group as to the protecting group for hydroxyl group, the reaction can be carried out under conditions similar to those employed in the reaction of compound (9) with compound (10) in reaction process formula-3A. In case of introducing tetrahydropyranyl group, the reaction can be carried out in a suitable solvent for a halogenated hydrocarbon such as methylene chloride or the like; a saturated hydrocarbon such as n-hexane, in the presence of p-toluenesulfonic acid or a pyridine salt thereof or a strong acidic ion-exchange resin such as Amberlist H-15 (a trademark for a series of ion-exchange resins manufactured by Rohm & Haas Co., Philadelphia, Pa., U.S.A.) or the like, with tetrahydropyran at room temperature to 60° C., for 1 to 5 hours. By using 1 to 2 times molar quantity of tetrahydropyran to 1 mole of the hydroxy group, tetrahydropyranyl group can be introduced. In case of introducing benzyl group or tri(lower alkyl)silyl group, the reaction can be carried out under conditions similar to those employed in the reaction process formula-3A, except that a benzyl halide such as benzyl chloride or the like; or a tri(lower alkyl)silyl halide such as tri(lower alkyl)silyl chloride is used in place of compound (10).

In case of introducing tert-butoxycarbonyl group as to the protecting group for amino group, the reaction can be carried out in a water-soluble organic solvent such as alcohol or the like in the presence of sodium hydroxide or triethylamine, by adding di-tert-butyl dicarbonate or 2-tert-butoxycarbonyloximino-2-phenylacetonitril at 0° C. to room temperature for 10 minutes to 5 hours. By using 1 to 2 times the molar quantity of tert-butoxycarbonyl group to 1 mole of the amino group, tert-butoxycarbonyl group can be introduced. In case of introducing benzyloxycarbonyl group, the reaction can be carried out in a water-soluble organic solvent such as alcohol or the like in the presence of sodium hydroxide or sodium carbonate, by adding benzyl chloroformate at 0° C. to room temperature for 30 minutes to 5 hours. By using 1 to 2 times the molar quantity of benzyloxycarbonyl group to 1 mole of the amino group, benzyloxycarbonyl group can be introduced.

In case of removing the methoxymethyl group from the hydroxyl group protected with methoxymethyl group, the reaction can be carried out under conditions similar to those employed in the demethoxymethylation of reaction process formula-1 and -2. In case of removing the tetrahydropyranyl group, the reaction can be carried out in a suitable inert solvent for example an alcohol such as methanol, ethanol or the like, in the presence of an organic acid such as p-toluenesulfonic acid, acetic acid or the like; or an inorganic acid such as boric acid; an ion-exchange resin such as Amberlist H-15, Dowex 50W-X8 (a trademark for a series of synthetic ion-exchange resins manufactured by Dow Chemical Co., Midland, Mich., U.S.A.) or the like, at room temperature to 100° C. for 1 to 5 hours. In case of removing benzyl group or tri(lower alkyl)silyl group, the reaction can be carried out under conditions similar to those employed in the debenzylation or detri(lower alkyl)silylation in reaction process formula-9.

In case of removing the tert-butoxycarbonyl group or benzyloxycarbonyl group from the amino group protected with tert-butoxycarbonyl group or benzylcarbonyl group, the reaction can be carried out in an inert solvent for example ethyl acetate, benzene, ethanol, acetic acid, dioxane or the like, by using about 10 times the equimolar quantity of hydrogen chloride at room temperature for 30 minutes to 1 hour; or treated with trifluoroacetic acid at room temperature for 1 hour; or treated with trimethylsilyl iodide in chloroform or acetonitrile at room temperature for 30 minutes. In case of removing the benzyloxycarbonyl group the reaction can be carried out in an organic solvent for example an alcohol; or ammonia, by catalytically reducing in the presence of palladium-carbon, palladium black or the like at −50° C. to 100° C. for 30 minutes to 10 hours, so that debenzyloxycarbonylation can be proceeded.

Some of the desired products according to the present invention can be isolated from a plant as follows. Thus, 3-(Z-10-pentadecenyl)-1,4-benzoquinone and 5-methoxy-2-hydroxy-5-methoxy-3-(cis-8-tridecenyl)-1,4-benzoquinone can be extracted and isolated from a plant of *Ardisia japonica* (Thunb.) Blume originated in Japan, China and other countries. In that, leaves, stems, roots and fruits (preferably stems and roots) of *Ardisia japonica* (Thunb.) Blume are extracted with a solvent for example a lower alcohol such as methanol, ethanol, isopropanol or the like; an aromatic hydrocarbon such as benzene, toluene, xylene or the like; a halogenated hydrocarbon such as chloroform, dichloromethane, dichloroethane or the like; an ether such as diethyl ether, dioxane, tetrahydrofuran or the like; an aliphatic hydrocarbon such as n-hexane, cyclohexane, n-heptane or the like, and the extract is concentrated under reduced pressure to obtain the primary extract. A method for isolating the above-mentioned desired compound from the primary extract is not specifically restricted and any known method applying physico-chemical properties of the compound can be employed. Thus, the isolation can be carried out by, for example, a method applying the difference of the solubility between the compound and impurities, a method applying the difference of the adsorptive affinity to a common adsorbent such as activated carbon, XAD-2, silica gel; ion-exchange resins or Sephadex products, or a method applying the difference of the distribution coefficients between the two liquid phases, or combinations of these methods. More specifically, the primary extract is treated by a distributional solvent extraction method, for example the primary extract is dissolved in a mixture of a water-soluble organic solvent with water, such as a mixture of methanol-water (1:4 by volume/volume), then the solution is extracted with a solvent such as n-hexane, benzene, ethyl acetate, diethyl ether, chloroform or the like, further the resultant extract is concentrated under a reduced pressure, and the concentrate is treated by a column chromatography. As to the carrier used in the column chromatography, any one employed in usual separation method can be applied, for example ion-exchange resins, gel filtration carriers and others such as silica gel, activated alumina, silver nitrate-silica gel, calcium phosphate, activated carbon, Florisil (a trademark for powdered magnesia-silica gel, manufacture by Floridin Co., Pittsburgh, Pa., U.S.A.) magnesia, styrene-type polymer resine, Dowex ion-exchange resins (a trademark for a series of ion-exchange resins manufactured by Dow Chemical Co., Midland, Mich., U.S.A.), Amberlite (a trademark for a series of ion-exchange resins manufactured by Rohm & Haas Co., Philadelphia, Pa., U.S.A.), ion exchange cellulose can be exemplified. As to the eluents used in the isolation procedure, any solvent for example n-hexane, benzene, diethyl ether, chloroform, ethyl acetate, acetone, methanol, ethanol, water, an aqueous solution of acetic acid, an aqueous solution of hydrochloric acid and others can be exemplified, and these solvent can be used singly or in the form of a mixed solvent thereof. After purifying the desired compound by the column chromatography, the compound can be further purified, upon request by several purification and isolation methods for example precipitation method, solvent extraction method, dilution method, recrystallization method, high speed liquid chromatography, gas chromatography, liquid drop counter current partition chromatography, thin layer chromatography, distillation, gel filtration and others. On the other hand, the primary extract may be purified and isolated by method of column chromatography without treated through a distributional solvent extraction.

According to the present invention, 16-(2- hydroxy-5-methoxy-1,4-benzoquinone-3-yl)-1-(2-hydroxy-5-methoxy-6-methyl-1,4-benzoquinone-3-yl)-Z-8-hexadecene, 1-(2-hydroxy-5-methoxy-1,4-benzoquinone-3-yl)-16-(3,5-dihydroxy-4-methylphenyl)-Z-8-hexadecene and 1-(2-hydroxy-5-methoxy-1,4-benzoquinone-3-yl)-16-(3,5-dihydroxyphenyl)-Z-8-hexadecene are isolated from *Ardisia Sieboldii* Miq. originated in Japan, China and other countries, through the following procedures. Thus, leaves, branches, woods, barks, roots, skins of root, fruits, seeds (preferably leaves) are extracted with a solvent, for example the solvent used in the extraction from the above-mentioned *Ardisia japonica* (Thunb.) Blume, and the extract is concentrated under a reduced pressure to obtain the primary extract. Then this primary extract is further extracted by a method of distributional solvent extraction with a solvent same as used in case of the extraction from *Ardisia japonica* (Thunb.) Blume, and the resulting extract is concentrated under a reduced pressure to obtain the secondary extract. The secondary extract is purified by means of a column chromatography. As to the carriers and the eluent for this purpose, those used in the purification from *Ardisia japonica* (Thunb.) Blume can also be employed. After purifying the desired compounds by means of column chromatography, the compounds may further be purified, upon request by several purification as shown in the case of the extraction of *Ardisia japonica* (Thunb.) Blume.

Among the desired compounds of the present invention, those having acidic groups can be able to form pharmaceutically acceptable salts with basic compounds. As to the basic compounds, metal hydroxides such as sodium hydroxide, potassium hydroxide, calcium hydroxide and others; alkali metal carbonates and hydrogen carbonates such as sodium carbonate, sodium hydrogen carbonate and others; alkali metal alcoholates such as sodium methylate, potassium ethylate and others; ammonia; amines such as triethylamine, tripropylamine and others can be exemplified. Furthermore, among the desired compounds of the present invention, those having basic groups can be able to form pharmaceutically acceptable salts with acids. As to the acids, hydrochloric acid, hydrobromic acid, oxalic acid, citric acid, succinic acid and others can be exemplified.

The desired products prepared respectively in the above-mentioned steps can easily be isolated and purified by usual separation means. Furthermore, the active ingredient, 5-lipoxygenase inhibitor of the present invention may preferably be purified finally. As to the purification and isolation methods, solvent extraction, dilution method, recrystallization, distillation, adsorption chromatography, ion-exchange chromatography, gel-permeation chromatography and others can be exemplified.

The desired products of the present invention are used in the form of generally acceptable pharmaceutical compositions which are prepared by using diluents and excipients such as fillers, bulking agents, binders, wetting agents, disintegrating agents, surfactants, lubricants and the like. Administration unit forms of these pharmaceutical compositions of the present invention can be varied and selected so as to meet various therapeutical purposes. Typical forms of the pharmaceutical compositions can be exemplified such as tablets, aerosols, pills, powders, liquids, suspensions, emulsions, granules, capsules, suppositories, injections (liquids, suspensions and others) and the like.

In shaping into the form of tablets, those known as the carriers in this field can widely be applied for example, excipients such as lactose, purified sugar, sodium chloride, glucose, urea, starch, calcium carbonate, kaolin, crystalline cellulose, silicic acid and others; binders such as water, ethanol, propanol, simple syrup, a glucose solution, starch solution, gelatin solution, carboxymethyl cellulose, shellac, methyl cellulose, potassium phosphate, polyvinylpyrrolidone and others; disintegrating agents such as dried starch, sodium alginate, agar-agar powder, laminalia powder, sodium hydrogen carbonate, calcium carbonate, a fatty acid ester of polyoxyethylene sorbitan, sodium laurylsulfate, monoglyceride of stearic acid, starch, lactose and others; disintegration inhibitors such as purified sugar, stearin, cacao butter, hydrogenated oils and others; absorption accelerators such as quaternary ammonium base, sodium lauryl-sulfate and others; wetting agents such as glycerin, starch and others; adsorption accelerators such as starch, lactose, kaolin, bentonite, colloidal silicic acid and others; and lubricants such as purified talcum powder, stearic acid salts, boric acid powder, polyethylene glycol and others can be exemplified. If necessary, the tablets can further be coated with usual coating film to make them into coated tablets, for example sugar-coated tablets, gelatin film-coated tablets, enteric film-coated tablets, film-coated tablets, or double-layered tablets, multiple layers tablets and others. In shaping into the form of pills, those known as the carriers in this field can widely be applied for example, excipients such as glucose, lactose, starch, cacao butter, hydrogenated vegetable oils, kaolin, talcum powder and others; binders such as powdered gum arabic, powdered tragacanth gum, gelatin, ethanol and others; disintegrating agent such as laminalia, agar-agar powder and others. In shaping into the form of suppositories, those known in this field can widely be applied for example, polyethylene glycol, cacao butter, a higher alcohol, an ester of a higher alcohol, gelatin, semi-synthesized glyceride and others. In case of preparing injections, solutions and suspensions being prepared are sterilized, and they are preferably as isotonic to the blood. In preparing into the form of liquids, emulsions and suspensions, those known as the diluents in this field can widely be applied, for example water, ethanol, propylene glycol, ethoxylated isostearyl alcohol, polyoxylated isostearyl alcohol, a polyoxyethylene sorbitan fatty acid ester, and others. In case of preparing isotonic solutions, sufficient amount of sodium chloride, glucose or glycerin may be added to make the solution to be isotonic to the blood. The pharmaceutical compositions for injection preparation may further be contain usual dissolving agents, buffer solutions, analgesic agents or the like if necessary. The pharmaceutical composition of the present invention may also be contain coloring agents, preservatives, perfumes, seasoning agents, sweetening agents and others, as well as contain other medicines, if necessary.

In shaping into the form of aerosols, those known as the dispersing agents, propellants in this field can widely be applied. As to the dispersing agents, lecithins such as soybean lecithin, egg yolk lecithin or the like; fatty acids such as oleic acid, linoleic acid, linolenic acid or the like; sorbitans such as sorbitan trioleate, sorbitan monooleate and the like can be exemplified. As to the propellants, usual inflammable liquified gases such as Freon-11, Freon-12, Freon-114 (trademarks for a series of fluorocarbon products manufactured by E. I. Du Pont de Nemours & Co., Wilmington, Del., U.S.A.) and others can be exemplified.

The amount of the desired product according to the present invention to be contained as the active ingredient in the pharmaceutical composition is not specifically restricted and can be selected from a wide range, generally 1 to 70% by weight, preferably 1 to 30% by weight may be used.

Administration method of the above-mentioned pharmaceutical composition is not specifically restricted and can be administered through a suitable method for the respective types of administration forms, depending upon age of the patient, distinction of the sex and other conditions, conditions of the patient and others. For example, tablets, pills, liquids, suspensions, emulsions, granules and capsules are administered orally; injections are administered intraveneously singly or as a mixture with usual injectable transfusions such as a glucose solution, an amino acids solutions, and others; and if necessary the injections are administered singly intramuscularly, intracutaneously, subcutaneously or intraperitoneally; and the suppositories are administered into rectum; and the aerosols are administered into the bronchus by spraying through the mouth or the nose.

The dosage of the desired products of the present invention may suitably be selected depending upon the method for administration, age of the patient, distinction of sex and other conditions, and conditions of the symptoms, and generally the active ingredient can be administered in about 0.005 to 10 mg, preferably 0.1 to 1 mg/kg of the body weight/day.

The present invention will be illustrated more specifically by way of showing the following examples, in which the preparations of compounds to be used as the starting materials will be shown in Reference Examples, and the preparations of the desired products will be shown in Examples. Furthermore, examples of pharmaceutical compositions as well as pharmacological test results are shown. The present invention, however will not be restricted to these examples.

REFERENCE EXAMPLE 1

10 Grams of 1,4-dimethoxy-2,5-bis(methoxymethoxy)benzene was dissolved in 300 ml of tetrahydrofuran, and the solution was cooled to $-78°$ C. in a dry ice-acetone bath. To this cooled solution was added dropwise 35 ml of sec-butyllithium (1.3M-cyclohexane solution) and was stirred for 30 minutes. Furthermore, 15 ml of 1,5-dibromopentane (0.11 mole) was added dropwise thereto, next 12 g of sodium iodide and 20 ml of hexamethylphosphoric triamide was added to the reaction mixture. The whole reaction mixture was stirred at room temperature for 12 hours. Tetrahydrofuran was removed under reduced pressure, and the residue thus obtained was dissolved in 1,000 ml of a mixed solvent of benzene-ether (1:1). The organic layer was washed 4 times with 200 ml of water, and 4 times with a saturated sodium chloride aqueous solution, and was dried over anhydrous magnesium sulfate.

The solvent was removed by evaporation under a reduced pressure, and the residue obtained was treated by a silica gel column chromatography (diameter 8 cm×length 30 cm, solvent: ethyl acetate:n-hexane=1:4, "Wakogel C-200") to yield 11.24 g (yield=71.2%) of 1-(5-bromopentyl)-2-5-dimethoxy-3,6-bis(methoxymethoxy)benzene. Oily substance.

PMR, $\delta$ ppm (CDCl$_3$): 1.56 (4H, brm), 1.88 (2H, brm), 2.65 (2H, brt, J=6.8Hz), 3.40 (2H, t, J=6.8Hz), 3.52 (3H, s), 3.58 (3H, s), 3.78 (6H, s), 5.02 (2H, s), 5.17 (2H, s), 6.65 (1H, s).

REFERENCE EXAMPLE 2

By a method as described in Reference Example 1 except that 1,9-dibromononane was used in place of 1,5-dibromopentane, there was prepared 1-(9-bromononyl)2,5-dimethoxy-3,6-bis(methoxymethoxy)-benzene. Oily substance.

PMR, $\delta$ ppm (CDCl$_3$): 1.2–1.7 (12H, brm), 1.82 (2H, brm), 2.70 (2H, brt, J=6.9Hz), 3.40 (2H, t, J=6.9Hz), 3.53 (3H, s), 3.59 (3H, s), 3.79 (6H, s), 5.02 (2H, s), 5.17 (2H, s), 6.64 (1H, s).

REFERENCE EXAMPLE 3

10 Grams of 1,4-dimethoxy-2,5-bis(methoxymethoxy)benzene was dissolved in 500 ml of tetrahydrofuran, then to this solution was added 7.01 ml (46.44 mM) of N,N,N',N'-tetramethylethylenediamine and the whole mixture was cooled to $-78°$ C. in a dry ice-acetone bath. To this cooled mixture was added dropwise 29.1 ml of n-butyllithium (1.6M-hexane solution), then stirred for 30 minutes. Next, 26.4 ml (2.091M solution) of tetrahydrofuran solution of ethylene oxide and 0.5 ml of boron trifluoride-diethyl ether (BF$_3$·Et$_2$O were added to the reaction mixture. 10 Minutes after, the dry ice-acetone bath was removed from the reaction equipment, then 2 hours later, the reaction mixture was concentrated to obtain the residue and 500 ml of diethyl ether was added thereto, and washed 4 times with 200 ml of water, further washed 4 times with 200 ml of a saturated sodium chloride aqueous solution, next dried over anhydrous magnesium sulfate. After removal of the solvent under reduced pressure, the residue was treated by a silica gel column chromatography [diameter 6 cm×length 30 cm, eluent: ethyl acetate:n-hexane=(2:3), "Wakogel C-200"] to yield 8.5 g of 1-(2-hydroxyethyl)-2,5-dimethoxy-3,6-bis(methoxymethoxy)benzene. Colorless needless crystals. Melting point: 121°–123° C.

PMR, δ ppm (CDCl$_3$): 3.01 (3H, t, J=6.0Hz), 3.51 (3H, s), 3.58 (3H, s), 3.79 (3H, s), 3.80 (2H, t, J=6.0Hz), 3.82 (3H, s), 5.02 (2H, s), 5.13 (2H, s), 6.65 (1H, s).

REFERENCE EXAMPLE 4

1.3 Grams (4.3 mM) of 1-(2-hydroxyethyl)-2,5-dimethoxy-3,6-bis(methoxymethoxy)benzene was dissolved in 15 ml of dichloromethane, then under ice-cooling condition, 1 g of pyridinium chlorochromate was added thereto and the reaction mixture was stirred at a room temperature for 10 hours. After filtration, the filtrate was concentrated under a reduced pressure, and the residue obtained was treated by a silica gel column chromatography (diameter 3 cm×length 15 cm, eluent: 30% ethyl acetate: n-hexane, "Wakogel C-200") to yield 1 g of 2-[2,5-dimethoxy-3,6-bis(methoxymethoxy)phenyl]acetoaldehyde. Colorless oily substance.

PMR, δ ppm (CDCl$_3$): 3.49 (2H, d, J=2.1Hz), 3.50 (3H, s), 3.55 (3H, s), 3.76 (3H, s), 3.80 (3H, s), 5.01 (2H, s), 5.17 (2H, s), 6.78 (1H, s), 9.67 (1H, t, J=2.1Hz).

REFERENCE EXAMPLE 5

351 Milligrams (1.36 mM) of 1,4-dimethoxy-2,5-bis(methoxymethoxy)benzene was dissolved in a mixed solvent of 10 ml of tetrahydrofuran with 1 ml of hexamethylphosphoric triamide, and the solution was cooled to −78° C. in a dry ice-acetone bath. Then 1.60 ml (1.05M cyclohexane solution, 1.68 mM) of sec-butyllithium was added to the reaction mixture and stirred for 30 minutes. Next, a tetrahydrofuran solution containing 334 mg (1.11 mM) of 2-[2,5-dimethoxy-3,6-bis(methoxymethoxy)phenyl]acetoaldehyde in 2 ml of tetrahydrofuran was added thereto and stirred for 8 hours. The reaction mixture was concentrated under a reduced pressure, and the residue obtained was purified by a silica gel column chromatography (diameter 2 cm×length 10 cm, eluent: 40% ethyl acetate-n-hexane) to yield 503 mg of 1,2-bis[2,5-dimethoxy-3,6-bis(methoxymethoxy)phenyl]ethanol. Colorless oily substance.

PMR, δ ppm (CDCl$_3$): 2.99 (1H, dd, J=8.2, 2.5Hz), 3.12 (1H, dd, j=8.2, 2.5Hz), 3.53 (6H, s), 3.55 (3H, s), 3.63 (3H, s), 3.76 (1H, dd, J=2.5, 2.0Hz), 3.80 (3H, s), 3.81 (3H, s), 3.82 (3H, s), 3.90 (3H, s), 5.16–5.00 (4H, m), 5.16 (4H, br.s), 6.70 (1H, s), 6.72 (1H, s).

REFERENCE EXAMPLE 6

2.7 Grams (9.0 mM) of 2-[2,5-dimethoxy-3,6-bis(methoxymethoxy)phenyl]acetoaldehyde was dissolved in 80 ml of benzene, then to this solution was added 1.56 g (10.8 mM) of Meldrum's acid (2,2-dimethyl-1,3-dioxane-4,6-dione) and 2.18 g (21.6 mM) of triethylamine were added and the reaction mixture was stirred at room temperature for 12 hours. 100 Milliliters of benzene was added to the reaction mixture and washed twice with 200 ml of water and further washed twice with a saturated sodium chloride aqueous solution, then the benzene solution was dried over anhydrous magnesium sulfate. The benzene solution was concentrated under reduced pressure and the residue obtained was purified by a silica gel column chromatography (diameter 5 cm×length 15 cm, eluent: 30% ethyl acetatehexane, "Wakogel C-200") to yield 2.9 g of 1-[2,5-dimethoxy-3,6-bis(methoxymethoxy)phenyl]-2-(2,2-dimethyl-4,6-dioxo-1,3-dioxan-5-ylidene)ethane. Light yellow indefinite form powdery substance.

PMR, δ ppm (CDCl$_3$): 1.77 (6H, s), 3.51 (3H, s), 3.52 (3H, s), 3.76 (3H, s), 3.84 (3H, s), 4.35 (2H, d, J=6.5Hz), 5.03 (2H, s), 5.17 (2H, s), 6.75 (1H, s), 7.82 (2H, t, J=6.5Hz).

REFERENCE EXAMPLE 7

2.9 Grams of 1-[2,5-dimethoxy-3,6-bis(methoxymethoxy)phenyl]-2-(2,2-dimethyl-4,6-dioxo-1,3-dioxan-5-ylidene)ethane was dissolved in a mixed solvent of 90 ml of methanol with 90 ml of ethyl acetate, then under an ice-cooled condition, 3 g of sodium boron hydride was added thereto. 1 Hour later, the reaction mixture was concentrated under a reduced pressure, to the residue obtained was added 300 ml of ethyl acetate, and this mixture was washed twice with 200 ml of water, further washed twice with 200 ml of a saturated sodium chloride aqueous solution, then dried over anhydrous magnesium sulfate. The dehydrated ethyl acetate solution was concentrated under a reduced pressure to obtain the residue, and the residue was dissolved in a mixed solvent of 20 ml of ethanol with 40 ml of pyridine, then a catalytic amount of copper powder was added thereto and the mixture was heated at 100° C. in an oil bath and stirred for 8 hours. The reaction mixture was concentrated under a reduced pressure, to the residue thus obtained was added 300 ml of ethyl acetate, then the solution was washed twice with 200 ml of a diluted aqueous solution of hydrochloric acid (pH 3), further washed 4 times with 200 ml of water, next washed twice with 200 ml of a saturated sodium chloride aqueous solution, dried over anhydrous sodium sulfate, then concentrated under reduced pressure. The residue thus obtained was purified by a silica gel column chromatography (diameter 5 cm×length 15 cm, eluent: 40% ethyl acetate-n-hexane solution, "Wakogel C-200") to yield 1.9 g of ethyl 4-[2,5-dimethoxy-3,6-bis(methoxymethoxy)phenyl]butyrate. Colorless oily substance.

PMR, δ ppm (CDCl$_3$): 1.24 (3H, t, J=7.8Hz), 1.92 (2H, m), 2.37 (2H, t, J=8.0Hz), 2.75 (2H, t, J=8.0Hz), 3.56 (3H, s), 3.58 (3H, s), 3.80 (6H, s), 4.11 (2H, q, J=7.8Hz), 5.02 (2H, s), 5.18 (2H, s), 6.67 (1H, s).

REFERENCE EXAMPLE 8

1.9 Grams of ethyl 4-[2,5-dimethoxy-3,6-bis(methoxymethoxy)phenyl]butyrate was dissolved in 60 ml of tetrahydrofuran, then under an ice-cooled condition, 800 mg of lithium aluminium hydride was added thereto and stirred for 1 hour. Under an ice-cooled condition, 20 ml of ethyl acetate was added to the reaction mixture, then concentrated under a reduced pressure. To the residue thus obtained was added 300 ml of ethyl acetate, washed twice with 200 ml of water, then washed twice with 200 ml of a saturated sodium chloride aqueous solution, and dried over anhydrous sodium sulfate. Concentrated under a reduced pressure, thus 1.43 g of theus obtained alcohol was dissolved in 30 ml of dichloromethane, under an ice-cooled condition, 0.9 ml of triethylamine and 0.4 ml of methanesulfonyl chloride acid were added thereto and stirred at room temperature for 5 hours. 200 Milliliters of dichloromethane was added the reaction mixture, then washed twice with water, and washed twice with a saturated sodium chloride aqueous solution, then dried over anhydrous magnesium sulfate. Concentrated under reduced pressure to yield 1.5 g of 4-[2,5-dimethoxy-3,6-bis(methoxymethoxy)phenyl]butyl methanesulfonate. Colorless oily substance.

PMR, δ ppm (CDCl$_3$): 1.9–1.6 (4H, m), 2.75 (2H, t, J=7.5Hz), 2.97 (3H, s), 3.56 (3H, s), 3.58 (3H, s), 3.79 (3H, s), 3.80 (3H, s), 4.25 (2H, t, J=7.5Hz), 5.01 (2H, s), 5.18 (2H, s), 6.68 (1H, s).

REFERENCE EXAMPLE 9

1.5 Grams of 4-[2,5-dimethoxy-3,6-bis(methoxymethoxy)phenyl]butyl methanesulfonate was dissolved in a mixed solvent of 40 ml of acetone with 4 ml of hexamethylphosphoric triamide, then 2 g of sodium iodide was added to thereto and the whole mixture was heated at 70° C. in an oil bath and stirred for 1.5 hours. After the completion of the reaction, the reaction mixture was concentrated under a reduced pressure, then 200 ml of diethyl ether was added thereto, and washed twice with 100 ml of water, further washed twice with 100 ml of a saturated sodium chloride aqueous solution, and dried over anhydrous magnesium sulfate. Concentrated under reduced pressure to yield 1.3 g of 1-(4-iodobutyl)-2,5-dimethoxy-3,6-bis(methoxymethoxy)benzene. Colorless oily substance.

PMR, δ ppm (CDCl$_3$): 2.0–1.6 (4H, m), 2.70 (2H, t, J=7.8Hz), 3.23 (2H, t, J=7.8Hz), 3.56 (3H, s), 3.57 (3H, s), 3.80 (6H, s), 5.02 (2H, s), 5.17 (2H, s), 6.65 (1H, s).

REFERENCE EXAMPLE 10

30 Grams (0.116 moles) of 1,4-dimethoxy-2,5-bis(methoxymethoxy)benzene was dissolved in 1200 ml of anhydrous tetrahydrofuran and 300 ml of hexamethylphosphoric triamide, and the solution was cooled to −78° C. under argon gas stream. Next, 99.4 ml (1.2 equimolar quantity) of sec-butyllithium (1.4M solution) was added dropwise and the reaction mixture was stirred additionally. 30 Minutes later, 100 ml of anhydrous tetrahydrofuran solution of formaldehyde (containing about 5 g of formaldehyde, which is corresponding to 1.5 times the molar quantity) was added dropwise, and the temperature of the reaction mixture was gradually raised from −78° C. to room temperature, then the mixture was stirred continuously for 4 hours at room temperature. Tetrahydrofuran was removed by evaporation under reduced pressure, to the residue thus obtained was added a mixed solvent of 500 ml of benzene with 500 ml of diethyl ether, then the organic layer was washed four times with 300 ml of water, next washed three times with 200 ml of a saturated sodium chloride aqueous solution. After concentrating the solution, the residue thus obtained was treated by a silica gel column chromatography (diameter 5 cm×length 30 cm), and eluted with 20% ethyl acetate-n-hexane solution, then with 30% ethyl acetate-n-hexane solution to yield 17.8 g of desired product of 2,5-dimethoxy-3,6-bis(methoxymethoxy)phenylmethanol. Corless oily substance.

PMR, δ ppm (CDCl$_3$):: 3.10 (1H, t, J=7.5Hz), 3.53 (3H, s), 3.58 (3H, s), 3.81 (3H, s), 3.87 (3H, s), 4.72 (2H, d, J=7.5Hz), 5.05 (2H, s), 5.18 (2H, s), 6.76 (1H, s).

REFERENCE EXAMPLE 11

5 Grams (0.017 mole) of 2,5-dimethoxy-3,6-bis(methoxymethoxy)phenylmethanol was dissolved in 100 ml of carbon tetrachloride, then 9.90 g (2 times the molar quantity) of triphenylphosphine was added to this solution and the reaction mixture was refluxed under nitrogen gas stream for 8 hours. Then 500 ml of diethyl ether was added to the reaction mixture, the precipitates formed were removed by filtration, and the filtrate was concentrated, then was treated on a silica gel column chromatography (diameter 3.2 cm×length 13.5 cm), and eluted with first with benzene, next with 10% ethyl acetate-benzene solution to yield 4.2 g of the desired product of 1-chloromethyl-2,5-dimethoxy-3,6-bis(methoxymethoxy)benzene. Colorless oily substance.

PMR, δ ppm (CDCl$_3$):: 3.50 (3H, s), 3.60 (3H, s), 3.79 (3H, s), 3.89 (3H, s), 4.72 (2H, s), 5.10 (2H, s), 5.13 (2H, s), 6.75 (1H, s).

REFERENCE EXAMPLE 12

10 Grams of 1,4-dimethoxy-2,5-bis(methoxymethoxy)benzene was dissolved in 500 ml of anhydrous tetrahydrofuran and 50 ml of hexamethylphosphoric triamide. Next 7 ml of N,N,N',N'-tetramethylethylenediamine (TMEDA) was added thereto, and under argon gas stream, the reaction mixture was cooled to −78° C. Then 30 ml of n-butyllithium (1.6M solution) was added dropwise to the reaction mixture and stirred for 30 minutes. Next, 10 ml of anhydrous N,N-dimethylformamide (DMF) was added, further 0.5 ml of boron trifluoride-diethyl ether (BF$_3$·Et$_2$O) (47% ether solution) was added as the reaction accelerator to the reaction mixture, and the mixture was stirred at −78° C. for 2 hours. The temperature of the reaction mixture was elevated to room temperature, then the solvent was removed by evaporation under reduced pressure, to the residue thus obtained was added 300 ml of benzene and 300 ml of diethyl ether, then the organic layer was washed 4 times with 200 ml of water, and further washed three times with 100 ml of a saturated sodium chloride aqueous solution. After concentrated the organic layer under reduced pressure, the resultant residue was treated on a silica gel column chromatography, and eluted with 20% ethyl acetate-n-hexane solution to yield 6 g of 2,5-dimethoxy-3,6-bis(methoxymethoxy)benzaldehyde. Light yellow powdery substance.

PMR, δ ppm (CDCl$_3$): 3.53 (3H, s), 3.56 (3H, s), 3.84 (3H, s), 3.87 (3H, s), 5.10 (2H, s), 5.20 (2H, s), 7.03 (1H, s), 10.42 (1H, s).

REFERENCE EXAMPLE 13

3 Grams (10.48 mM) of 2,5-dimethoxy-3,6-bis(methoxymethoxy)benzaldehyde was dissolved in 100 ml of benzene, next 1.82 g (1.2 times the equivalent) of Meldrum's acid and 3 ml of triethylamine were added thereto, and the reaction mixture was stirred at room temperature for 5 hours. 200 milliliters of ethyl acetate was added to the reaction mixture, and the organic layer was washed twice with 50 ml of water, then washed three times with a saturated sodium chloride aqueous solution. The organic layer was then dehydrated on anhydrous sodium sulfate and concentrated to yield 4.39 g of 1-(2,2-dimethyl-4,6-dioxo-1,3-dioxan-5-ylidene)-1-[2,5-dimethoxy-3,6-bis(methoxymethoxy)-phenyl]methane. Yellow powdery substance.

PMR, δ ppm (CDCl₃): 1.84 (6H, s), 3.48 (3H, s), 3.53 (3H, s), 3.74 (3H, s), 3.82 (3H, s), 5.06 (2H, s), 5.18 (2H, s), 6.92 (1H, s), 8.46 (1H, s).

REFERENCE EXAMPLE 14

4.39 Grams of 1-(2,2-dimethyl-4,6-dione-1,3-dioxan-5-ylydene)-1-[2,5-dimethoxy-3,6-bis(methoxymethoxy)phenyl]methane was dissolved in 100 ml of methanol and 100 ml of ethyl acetate, and the solution was ice-cooled to 0° C. Next a large excess amount of sodium borohydride (NaBH₄) was added, and the reaction mixture was stirred, the reaction was completed in 1 hour. The solvent was removed by evaporation under reduced pressure, then to the residue was added 200 ml of ethyl acetate, and the organic layer was washed with a diluted hydrochloric acid, water and a saturated sodium chloride aqueous solution in this order, and dried on anhydrous sodium sulfate. The ethyl acetate solution was concentrated under reduced pressure to yield 4.07 g of 1-[2,5-dimethoxy-3,6-bis(methoxymethoxy)phenyl]-1-(2,2-dimethyl-4,6-dioxo-1,3-dioxan-5-yl)methane. Colorless oily substance.

PMR, δ ppm (CDCl₃): 1.77 (3H, s), 1.79 (3H, s), 3.49 (2H, d, J=6.4Hz), 3.53 (3H, s), 3.55 (3H, s), 3.80 (3H, s), 3.85 (3H, s), 4.61 (1H, t, J=6.4Hz), 5.10 (2H, s), 5.18 (2H, s), 6.73 (1H, s).

REFERENCE EXAMPLE 15

4.07 Grams of 1-[2,5-dimethoxy-3,6-bis(methoxymethoxy)phenyl]-1-(2,2-dimethyl-4,6-dioxo-1,3-dioxan-5-yl)methane was dissolved in 20 ml of ethanol and 40 ml of pyridine, then a catalytic amount of copper powder was added thereto and refluxed for 10 hours. The reaction mixture was filtered, and the filtrate was concentrated under reduced pressure, to the residue thus obtained was added 20 ml of ethyl acetate. The organic layer was washed with a diluted hydrochloric acid, water, a saturated sodium chloride aqueous solution in this order, dried over anhydrous sodium sulfate, concentrated under a reduced pressure to yield 3.42 g of ethyl 3-[2,5-dimethoxy-3,6-bis(methoxymethoxy)phenyl]propionate as an ethyl ester. Colorless oily substance.

PMR, δ ppm (CDCl₃): 1.25 (3H, t, J=7.2Hz), 2.57 (2H, brt, J=7.3Hz), 3.02 (2H, brt, J=7.3Hz), 3.52 (3H, s), 3.58 (3H, s), 3.79 (6H, s), 4.15 (2H, q, J=7.2Hz), 5.03 (2H, s), 5.17 (2H, s), 6.67 (1H, s).

REFERENCE EXAMPLE 16

900 Milligrams of the ethyl ester derivative obtained above was dissolved in 20 ml of anhydrous tetrahydrofuran, under an ice-cooled and nitrogen gas stream conditions, a large excess amount of lithium aluminium hydride was added thereto with stirring. The reaction was completed in 4 hours, then ethyl acetate was added to decompose unreacted excess lithium aluminium hydride. Further ice was added to the reaction mixture and the extraction with ethyl acetate was carried out. The organic layer was collected together and dried over anhydrous sodium sulfate, concentrated under reduced pressure to yield 700 mg of 3-[2,5-dimethoxy-3,6-bis(methoxymethoxy)phenyl]propionylalcohol. Colorless oily substance.

REFERENCE EXAMPLE 17

700 Milligrams of 3-[2,5-dimethoxy-3,6-bis(methoxymethoxy)phenyl]propionyl alcohol was dissolved in 20 ml of anhydrous methylene chloride, under argon gas stream condition, 0.21 ml of methanesulfonyl chloride, 0.3 ml of triethylamine were added thereto under ice-cooled condition. The temperature of the reaction mixture was elevated to room temperature, then the reaction mixture was stirred continuously for 12 hours. 100 Milliliters of ethyl acetate was added to the reaction mixture, and the organic layer was washed with water, a saturated sodium chloride aqueous solution, then concentrated to yield 700 mg of 3-[2,5-dimethoxy-3,6-bis(methoxymethoxy)phenyl]propyl methanesulfonate was obtained as a mesylate. Colorless oily substance.

PMR, δ ppm (CDCl₃): 2.04 (2H, tt, J=7.6, 6.4Hz), 2.81 (2H, t, J=7.6Hz), 3.01 (3H, s), 3.53 (3H, s), 3.58 (3H, s), 3.80 (6H, s), 4.26 (2H, t, J=6.4Hz), 5.03 (2H, s), 5.18 (2H, s), 6.68 (1H, s).

REFERENCE EXAMPLE 18

700 Milligrams of the mesylate prepared in the above-mentioned

REFERENCE EXAMPLE 17 was dissolved in 80 ml of acetone, and 1 g of sodium iodide was added to the solution, then the mixture was refluxed for 1.5 hours.

Acetone was removed by evaporation under reduced pressure, then to the residue thus obtained was added 200 ml of ethyl acetate and 50 ml of water, the organic layer was washed with water and a saturated sodium chloride aqueous solution in this order, and concentrated. The residue thus obtained was treated on a silica gel column chromatography (diameter 1.8 cmm × length 20 cm), then eluted with 20% ethyl acetate-n-hexane solution to yield 500 mg of 1-(3-iodopropyl)-2,5-dimethoxy-3,6-bis(methoxymethoxy)benzene. Colorless powdery substance.

PMR, δ ppm (CDCl₃): 2.11 (2H, tt, J=7.7, 7.1Hz), 2.78 (2H, br.t, J=7.7Hz), 3.24 (2H, t, J=7.1Hz), 3.53 (3H, s), 3.59 (3H, s), 3.79 (3H, s), 3.80 (3H, s), 5.03 (2H, s), 5.17 (2H, s), 6.67 (1H, s).

REFERENCE EXAMPLE 19

50 Grams of 1,4-dimethoxy-2,5-bis(methoxymethoxy)benzene was dissolved in 1 liter of anhydrous toluene, then to this solution were added 250 ml of hexamethylphosphoric triamide and 43.85 ml of N,N,N',N'-tetramethylethylenediamine, and the whole mixture was cooled to −78° C. under argon gas stream condition. 182 Milliliters of n-butyllithium (1.6M solution) was added dropwise to the reaction mixture and stirred. The reaction mixture was kept at −78° C. and stirred for 30 minutes, then 58 ml of 1,5-diiodomethane was added and the reaction mixture was further stirred for 10 to 12 hours. 500 Milliliters of benzene was added to the reaction mixture, and the organic layer was washed with water and a saturated sodium chloride aqueous solution in this order, then dehydrated on anhydrous magnesium sulfate. The solvent was removed by evaporation under reduced pressure, and the residue thus obtained was treated on a silica gel column chromatography (diameter 5 cm × length 30 cm), and eluted with n-hexane, then with 5% ethyl acetate-n-hexane to yield 40.5 g of 1-(5-iodopentyl)-2,5-dimethoxy-3,6-bis(methoxymethoxy)benzene. Colorless oily substance.

PMR, δ ppm (CDCl₃): 1.5–2.0 (6H, m), 2.66 (2H, br.t, J=7Hz), 3.16 (2H, t, J=7Hz), 3.50 (3H, s), 3.57 (3H, s), 3.76 (6H, s), 4.99 (2H, s), 5.12 (2H, s), 6.62 (1H, s).

REFERENCE EXAMPLE 20

126 Milligrams of 1,4-dimethoxy-2,5-bis(methoxymethoxy)benzene was dissolved in 2 ml of anhydrous tetrahydrofuran, then 0.2 ml of hexamethylphosphoric triamide was added to the solution and whole mixture was cooled to −78° C. in a dry ice-acetone bath. Under argon gas stream conditions, 0.5 ml of sec-butyllithium was added dropwise to the reaction mixture and stirred for 30 minutes. Then 140 mg of 2-bromoethyl tert-butyldimethylsilyl ether and 70 mg of anhydrous sodium iodide were added to the reaction mixture and was stirred at −78° C. for 4 hours, then the temperature was elevated to room temperature. The solvent was removed by evaporation under reduced pressure, then to the residue thus obtained were added 50 ml of benzene and 50 ml of diethyl ether, the organic layer was washed three times with 30 ml of water, then washed three times with 30 ml of a saturated sodium chloride aqueous solution, and dried over anhydrous magnesium sulfate. The solvent was removed by evaporation under reduced pressure, then the residue was treated on a silica gel thin layer chromatography, and purified by developing with 30% ethyl acetate-n-hexane mixed solvent to yield 15.0 mg of 2-[2,5-dimethoxy-3,6-bis(methoxymethoxy)phenyl]ethyl tert-butyldimethylsilyl ether. Colorless oily substance.

PMR, δ ppm (CDCl$_3$): 0.03 (6H, s), 0.90 (9H, s), 2.94 (2H, t, J=8.5Hz), 3.53 (3H, s), 3.57 (3H, s), 3.60 (2H, t, J=8.5Hz), 3.76 (6H, s), 5.02 (2H, s), 5.13 (2H, s), 6.67 (1H, s).

15.0 Milligrams of 2-[2,5-dimethoxy-3,6-bis(methoxymethoxy)phenyl]ethyl tert-butyldimethylsilyl ether was dissolved in 2 ml of anhydrous tetrahydrofuran, under argon gas stream conditions, 0.1 ml of tetrahydrofuran solution of 1 mole of tetra-n-butylammonium fluoride was added thereto and stirred for 30 minutes, the reaction of removal of the protecting group was completed quantitatively. The solvent was removed by evaporation under reduced pressure, and the residue obtained was treated on a silica gel thin layer chromatography and purified by developing with 30% ethyl acetate-n-hexane to yield 9.0 mg of 1-(2-hydroxyethyl)-2,5-dimethoxy-3,6-bis(methoxymethoxy)benzene.

REFERENCE EXAMPLE 21

4.81 Grams of 2-[2,5-dimethoxy-3,6-bis(methoxymethoxy)phenyl]ethanol was dissolved in 50 ml of dichloromethane, then 4.2 ml of diisopropylethylamine was added, then under an ice-cooled condition, 1.4 ml of methoxymethyl chloride was added. The temperature of the reaction mixture was elevated to a room temperature, and stirred for additional 5 hours. 50 Milliliter of dichloromethane was added to the reaction mixture, and the organic layer was washed with water and a saturated sodium chloride aqueous solution, then dried over anhydrous magnesium sulfate, and concentrated. The residue thus obtained was purified by a silica gel column chromatography (diameter cm×length 15 cm, Merck, eluent: 30% ethyl acetate-n-hexane solution) to yield 4.9 g of 1-methoxymethoxy-2-2,5-dimethoxy-3,6-bis(methoxymethoxy)]phenylethane. Colorless oily substance.

PMR, δ ppm (CDCl$_3$): 3.19 (2H, t, J=7.6Hz), 3.32 (3H, s), 3.53 (3H, s), 3.57 (3H, s), 3.75 (2H, t, J=7.6Hz), 3.80 (3H, s), 3.82 (3H, s), 4.71 (2H, s), 5.06 (2H, s), 5.18 (2H, s), 6.72 (1H, s).

REFERENCE EXAMPLE 22

259 Milligrams of 1,4-dimethoxy-2,5-bis(methoxymethoxy)benzene was dissolved in a mixed solvent of 12 ml of toluene with 3 ml of hexamethylphosphoric triamide, to this solution was added 0.303 ml of N,N,N',N'-tetramethylethylenediamine, then the whole mixture was cooled to −78° C. in a dry ice-acetone bath. Next, 1.34 ml of n-butyllithium (1.6 mole hexane solution) was added dropwise to the reaction mixture and stirred for 20 minutes. Further, 0.14 ml of dimethyl disulfide was added dropwise and stirred for additional 2 hours. The reaction mixture was warmed to room temperature, 30 ml of diethyl ether was added, then the organic layer was washed three times with 20 ml of water, further washed three times with 20 ml of a saturated sodium chloride aqueous solution, and dried over anhydrous magnesium sulfate. Then this solution was concentrated under reduced pressure, and the residue obtained was purified by thin layer chromatography (thickness 2 mm, silica gel, solvent: 40% ethyl acetate-n-hexane solution) to yield 152 mg of 1,4-dimethoxy-2,5-bis(methoxymethoxy)-3-methylthiobenzene. Colorless oily substance.

PMR, δ ppm (CDCl$_3$): 2.46 (3H, s), 3.54 (3H, s), 3.67 (3H, s), 3.82 (3H, s), 3.85 (3H, s), 5.12 (2H, s), 5.19 (2H, s), 6.78 (1H, s).

REFERENCE EXAMPLE 23

5.0 Grams of 1,4-dimethoxy-2,5-(dimethoxymethoxy)benzene was dissolved in a mixed solvent of 250 ml of tetrahydrofuran with 25 ml of hexamethylphosphoric triamide, then to this solution was added 3.5 ml of N,N,N',N'-tetramethylethylenediamine and the whole mixture was cooled to −78° C. in a dry ice-acetone bath. Next, 15 ml of n-butyllithium was added, and 30 minutes later oxygen gas was blown to the reaction mixture for 30 minutes. The reaction mixture was then concentrated, and 300 ml of ethyl acetate was added to the residue, the organic layer was washed twice with a saturated sodium bisulfite aqueous solution, washed with water and with a saturated sodium chloride aqueous solution, then dried over anhydrous magnesium sulfate. The solution was concentrated to yield 4.1 g of 1,4-dimethoxy-2,5-dimethoxymethyloxy-6-hydroxybenzene. Amorphous powdery substance.

PMR, δ ppm (CDCl$_3$): 3.52 (3H, s), 3.59 (3H, s), 3.80 (3H, s), 3.87 (3H, s), 5.08 (2H, s), 5.19 (2H, s), 6.33 (1H, s), 6.42 (1H, s, OH).

EXAMPLE 1

The extraction from 2.19 kilograms of rhizome of *Ardisia japonica* (Thunb.) Blume (produce of Japan) was carried out 3 times with 10 liters of methanol at room temperature for 3 days. The extract obtained was concentrated under reduced pressure to give 145 g of residue as the primary extract. Then 2 liters of methanolwater (1:4 mixture by volume/volume) was added to the primary extract, the extraction from whole mixture thus obtained was further extracted 3 times with 1 liter of n-hexane. The n-hexane extract was concentrated under reduced pressure to obtain 9.8 g of residue as the secondary extract. The secondary extract was fractionated by means of a silica gel column chromatography to obtain a fraction containing 5-methoxy-3-(Z-10-pentadecenyl)-1,4-benzoquinone (Compound A). This fraction containing Compound A was further purified by a silica gel column chromatography (adsorbent: "Silica gel 60" manufactured by E. Merck A.G., Darmstadt, Germany; eluent: chloroform). The crude product obtained containing Compound A was purified by means of a high-performance liquid chromatography (filler: 20%-silver nitrate-silica gel, diameter 8 mm×length 300 mm, eluent: n-hexane-ethyl acetate (85:15 mixture by volume/volume), flow rate: 2.5 ml/min., detector: ditection at 290 nm), then recrystallized from ethanol-water (1:4 mixture by volume/volume) to obtain 57.5 mg of 5-methoxy-3-(Z-10-pentadecenyl)-1,4-benzoquinone (Compound A). Yellow crystals.

Melting point: 39.5°–41.5° C.

IR, $\nu_{max}^{CHCl_3}$: 2960, 2875, 1680, 1650, 1625, 1605, 1460, 1325, 1220, 1180, 1055, 900, 835 cm$^{-1}$.

PMR, $\delta_{ppm}^{CDCl_3}$ (400 MHz): 0.90 (3H, t, J=7.3Hz), 1.20–14.0 (16H, m), 2.01 (4H, m), 2.43 (2H, dt, J=7.8Hz, 1.4Hz), 3.82 (3H, s), 5.35 (2H, m), 5.88 (1H, d, J=2.2Hz), 6.48 (1H, dt, J=2.2Hz, 1.4Hz).

CMR, (50 MHz $\delta_{ppm}^{CDCl_3}$): 13.9, 22.4, 27.0, 27.3, 28.0, 28.8, 29.3, 29.6, 29.8, 32.1, 56.2, 107.3, 130.0, 133.1, 147.9, 159.3, 182.2, 187.6.

UV, $\lambda_{max}^{EtOH}$: 266nm ($\epsilon$=11,000), 362nm ($\epsilon$=750).

Mass spectrometry (for $C_{22}H_{34}O_3$): Calculated m/z: 346.2507, Found m/z: 346.2497.

| Elementary analysis: | | |
|---|---|---|
| | C | H |
| Calculated (%): | 76.26 | 9.89 |
| Found (%): | 76.11 | 9.95 |

EXAMPLE 2

Following to the fractionation by means of a silica gel column chromatography conducted in the abovementioned Example 1, a fraction containing 5-methoxy-2-hydroxy-3-(Z-8-tridecenyl)-1,4-benzoquinone (Compound B) was obtained by eluting with chloroform-methanol (20:1 mixture by volume/volume). This fraction was further purified by a silica gel column chromatography (adsorbent: "Silica gel 60" manufactured by E. Merck A. G., Dalmstadt, Germany, eluent: chloroform). The crude fraction containing Compound B thus obtained was purified by means of a high performance liquid chromatography [filler: "Lichrosorb PR-2" manufactured by E. Merck A.G., Dalmstadt, Germany), diameter 8 mm×length 300 mm, eluent: methanol-water-acetic acid (75:25:0.06 by voluem/volume), flow rate: 4 ml/min., ditector: detection at 280 nm], then recrystallized from ethanol-water (4: 1 by volume/volume) to obtain 98 mg of 5-methoxy-2-hydroxy-3-(Z-8-tridecenyl -1,4benzoquinone. Orange yellow plate-like crystals.

Melting point: 62°–64° C.

IR, $\nu_{max}^{KBr}$: 3360, 2940, 2860, 1660, 1635, 1600, 1465, 1445, 1385, 1358, 1300, 1205, 1115, 1082, 1040, 1015, 970, 915, 838, 760, 600, 565 cm$^{-1}$.

PMR, $\delta_{ppm}^{CDCl_3}$ (400 MHz): 0.89 (3H, t, J=7.3Hz), 1.20–1.40 (12H, m), 1.45 (2H, m), 2.01 (4H, m), 2.43 (2H, t, J=7.5Hz), 3.85 (3H, s), 5.34 (2H, m), 5.83 (1H, s), 7.22 (1H, s).

CMR, (50 MHz $\delta_{ppm}^{CDCl_3}$): 13.9, 22.3, 22.6, 26.9, 27.2, 28.0, 29.16, 29.24, 29.5, 29.7, 31.9, 56.6, 102.2, 119.3, 129.8, 151.5, 161.2, 181.6, 182.8.

UV, $\lambda_{max}^{EtOH}$: 287 nm ($\epsilon$=17,700), 420 nm ($\epsilon$=500).

Mass spectrometry (for $C_{20}H_{30}O_4$): Calculated m/z: 334.2143; Found m/z: 334.2128.

| Elementary analysis: | | |
|---|---|---|
| | C | H |
| Calculated (%): | 71.82 | 9.04 |
| Found (%): | 71.98 | 8.95 |

EXAMPLE 3

The extraction from 1.23 kilograms of *Ardisia Sieboldii* Miq. (produce of Japan) was extracted 3 times with 10 liters of methanol at room temperature for 3 days. The extract obtained was concentrated under a reduced pressure to obtain residue as the primary extract. To 188 g of the primary extract was added 2 liters of methanol-water (1:4 mixture by volume/volume), then distributional extraction was conducted 3 times with 2 liters of n-hexane. After removal of the n-hexane layer, further extraction was conducted 3 times with 2 liters of benzene. The benzene extract was concentrated under reduced pressure to obtain 37.8 g of residue as the secondary extract. The secondary extract was fractionated by means of a silica gel column chromatography [adsorbent: "Silica gel 60" manufactured by E. Merck A. G., Darmstadt, Germany, eluent: benzene-ethyl acetate (8:1 mixture by volume/volume)] to obtain a fraction containing 5-methoxy-2-hydroxy-3-(Z-8-heptadecenyl)-1,4-benzoquinone (Compound C). This fraction containing Compound C was further purified by a silica gel column chromatography (adsorbent: "Silica gel 60", manufacture by E. Merck A.G., eluent: chloroform), then recrystallized from ethanol-water (4:1 mixture by volume/volume) to obtain 80 mg of 5-methoxy-2-hydroxy-3-(Z-8-heptadecenyl)-1,4-benzoquinone (Compound C). Orange yellow plate crystals.

Melting point: 69.5°–70.5° C.

IR, $\nu_{max}^{KBr}$: 3360, 2940, 2860, 1660, 1635, 1598, 1462, 1442, 1382, 1355, 1310, 1200, 1115, 1060, 915, 835, 760, 685, 600, 565 cm$^{-1}$.

PMR, $\delta_{ppm}^{CDCl_3}$ (400 MHz): 0.88 (3H, t, J=6.4Hz), 1.20–1.40 (20H, m), 1.45 (2H, m), 2.00 (4H, m), 3.86 (3H, s), 5.34 (2H, m), 5.85 (1H, s), 7.26 (1H, s).

CMR, (50 MHz $\delta_{ppm}^{CDCl_3}$): 14.1, 22.8, 27.4, 28.1, 29.4, 29.6, 29.9, 32.0, 56.7, 102.4, 119.6, 130.07, 130.13, 151.8, 161.6, 181.8, 183.1.

UV, $\lambda_{max}^{EtOH}$: 285 nm ($\epsilon$25,200), 420 nm ($\epsilon$=600)

Mass spectrometry: (for $C_{24}H_{38}O_4$): Calculated m/z: 390.2778; Found m/z: 390.2777.

| Elementary analysis: | | |
|---|---|---|
| | C | H |
| Calculated (%): | .73.80 | 9.81 |
| Found (%): | 73.78 | 9.90 |

EXAMPLE 4

Following to the fractionation by means of a silica gel column chromatography conducted in the abovementioned Example 3, a fraction containing 1-(5-methoxy-2-hdroxy-1,4-benzoquinone-3-yl)-16-(5-methoxy-2-hydroxy-6-methyl-1,4-benzoquinone-3-yl)-Z-8-hexadecene (Compound D) was obtained. This fraction was further purified by means of a silica gel column chromatography (adsorbent: "Silica gel 100" manufacture by E. Merck A. G., eluent: chloroform). The crude fraction thus obtained containing Compound D was purified by means of a separating thin layer chromatography (adsorbent: "Silica gel 60 F$_{254}$" manufactured by E. Merck A. G., developer: chloroform), then recrystallized from benzene-hexane (4:1 mixture by voluem/volume) to obtain 168.3 mg of 1-(5-methoxy-2-hydroxy-1,4-benzoquinon-3-yl)-16-(5-methoxy-2-hydroxy-6-methyl-1,4-benzoquinon-3-yl)-Z-8-hexadecene (Compound D). Orange yellow powdery crystals.

Melting point: 88°-90° C.

IR, $\nu_{max}^{KBr}$: 3370, 2950, 2860, 1660, 1630, 1600, 1465, 445, 1385, 1355, 1290, 1210, 1130, 990, 920, 40, 760, 685, 640, 600, 565 cm$^{-1}$.

PMR, $\delta_{ppm}^{CDCl_3}$ (400 MHz): 1.2-1.4 (16H, m), 1.44 (4H, m), 1.93 (3H, s), 2.00 (4H, m), 2.40 (2H, t, J=7.3Hz), 2.45 (2H, t, 7.3Hz), 3.86 (3H, s), 4.09 (3H, s), 5.33 (2H, m), 5.84 (1H, s), 7.19 (2H, bs).

CMR, (50 MHz $\delta_{ppm}^{CDCl_3}$): 8.0, 22.70, 22.76, 27 3, 28.1, 8.3, 29.4, 29.6, 29.8, 56.7, 61.5, 102.9, 19.1, 119.6, 122.9, 130.1, 151.1, 151.8, 57.6, 161.6, 181.8, 183.1, 183.8, 184.5.

UV, $\lambda_{max}^{EtOH}$: 287 nm ($\epsilon$34,900), 420 nm ($\epsilon$=800)

Mass spectometry (for C$_{31}$H$_{42}$O$_8$): Calculated m/z: 542.2878, Found m/z: 542.2878,

|  | Elementary analysis: | |
|---|---|---|
|  | C | H |
| Calculated (%): | 67.61 | 7.80 |
| Found (%): | 67.68 | 7.74 |

EXAMPLE 5

The fraction obtained in Example 4 was fractionated by means of a silica gel column chromatography "Silica gel 100" manufactured by E. Merck A. G., eluent: chloroform-methanol (50:1 mixture by volume/volume)], A fraction containing 1-(2-hydroxy-5-methoxy-1,4-benzoquinon-3-yl)-16(4-methyl-3,5-dihydroxyphenyl)-Z-8hexadecene was obtained. This fraction was further fractionated by means of a preparative thin layer chromatography [adsorbent: "Silica gel 60 F$_{254}$" manufactured by E. Merck A. G., developing solvent: chloroformmethanol (20:1 mixture by volume/volume)]. Thus obtained fraction was purified by another preparative thin layer chromatography [adsorbent: "Silica gel 60 F$_{254}$" manufactured by E. Merck A. G., developing solvent: benzene-ethyl acetate (5:1 mixture by volume/volume)] to obtain 131 mg of 1-(2-hydroxy-5-methoxy-1,4-benzoquinon-3-yl)-16-(4-methyl-3, -dihydroxyphenyl)-Z-8-hexadecene. Orange powdery substance.

Melting point: 85°-87° C.

IR, $\nu_{max}^{KBr}$: 3375, 3050, 2950, 2875, 1642, 1618, 1598, 1460, 1440, 1360, 1320, 1210, 1150, 1075, 835, 795, 720, 670 cm$^{-1}$.

PMR, $\delta_{ppm}^{CDCl_3}$ (300 MHz): 1.2-1.6 (20H), 2.00 (4H, m), 2.10 (3H, s) , 2.44 (4H, t, J=7.3Hz), 3.85 (3H, s), 4.90 (2H, brs), 5.33 (2H, m), 5.83 (1H, s), 6.24 (2H, s), 7.25 (1H, brs).

CMR, $\delta_{ppm}^{CDCl_3}$ (50 MHz : 7.8, 22.9, 27.5, 28.3, 29.5, 29.8, 30.0, 31.3, 35.8, 56.8, 102.5, 108.0, 108.3, 119.8, 130.2, 142.3, 152.0, 155.1, 161.8, 182.1, 183.3.

Mass spectrometry: m/z 498 (M+), 483, 177, 169, 168, 163, 151, 138, 137.

Mass spectrometry (for C$_{30}$H$_{42}$O$_6$): Calculated m/z: 498.2981, Found m/z: 498.2972.

EXAMPLE 6

The fraction obtained in Example 4 was fractionated by means of a silica gel column chromatography "Silica gel 100" manufactured by E. Merck A. G., eluent: chloroform-methanol (10:1 mixture by volume/volume)], a fraction containing 1-(2-hydroxy-5-methoxy-1,4-benzoquinon-3-yl)-16-(3,5-dihydroxyphenyl)-Z-8-hexadecene was obtained. This fraction was further fractionated by means of preparative thin layer chromatography [adsorbent: "Silica gel 60 F$_{254}$" manufactured by E. Merck A. G., developing solvent: chloroform-methanol (20:1 mixture by volume/volume)]. Thus obtained fraction was purified by means of preparative thin layer chromatography [adsorbent: "Silica gel 60 F$_{254}$" manufactured by E. Merck A. G., developing solvent: benzene-ethyl acetate (2:1 mixture by volume/volume)] to obtain 150 mg of 1-(2-hydroxy-5-methoxy-1,4-benzoquinon-3-yl)-16-(3,5-dihydroxyphenyl)-Z-8-hexadecene. Yellow brawn oily substance.

Ir, $\nu_{max}^{KBr}$: 3390, 3050, 2960, 2880, 1642, 1610, 1458, 1385, 1360, 1315, 1215, 1155, 1040, 995, 840, 795, 695 cm$^{-1}$.

PMR, $\delta_{ppm}^{CDCl_3+CD_3OD}$ (20%) (400 MHz): 1.0-1.4 (20H, m), 1.77 (4H, m), 2.18 (2H, t, J=7.6Hz), 2.22 (2H, t, J=7.3Hz), 3.60 (3H, s), 5.09 (2H, m), 5.57 (1H, s), 5.90 (1H, t, J=2.2Hz), 5.95 (2H, d, J=2.2Hz).

CMR, $\delta_{ppm}^{CDCl_3}$ (50 MHz) 22.8, 27.3, 28.1, 29.4, 29.6, 29.8, 31.0, 36.0, 56.8, 100.8, 102.4, 108.3, 119.7, 130.2, 146.2, 152.1, 157.1, 161.5, 182.2, 183.2.

Mass spectrometry (for C$_{29}$H$_{40}$O$_6$) Calculated m/z: 484.2825., Found m/z: 484.2821.

EXAMPLE 7

303 Milligrams of 1,16-bis(5-methoxy-2-hydroxy-1,4-benzoquinon-3-yl)-Z-8-hexane was dissolved in 10 ml of methylene chloride, then to this solution was added a solution prepared by dissolving 100 mg of m-chlorobenzoic acid in 5 ml of methylene chloride, and the mixture was stirred at room temperature for 2 hours. The solvent was removed from the reaction mixture by evaporation under reduced pressure, the residue obtained was purified by means of a silica gel column chromatography ["Silica gel 100" manufactured by E. Merck A. G., eluent: benzene-ethyl acetate-tetrahydrofuran (5:4:1 mixture by volume/volume)], then recrystallized from ethyl acetate-n-hexane to obtain 200 mg of 1,16-bis(5-methoxy-2-hydroxy-1,4-benzoquinon-3-yl)-8,9-epoxyhexadecane. Yellow powdery substance.

Melting point: 134°-136° C.

PMR $\delta_{ppm}^{CDCl_3}$ (400 MHz): 1.2-1.5 (24H), 2.44 (4H, t, J=7.7Hz), 2.89 (2H, brs), 3.86 (6H, s), 5.83 (2H, s), 7.26 (overlapped).

Mass spectrometry: m/z 544 (M+), 185, 167, 149, 137.

EXAMPLE 8

37 Milligrams of 1,16-bis(5-methoxy-2-hydroxy-1,4-benzoquinon-3-yl)-8,9-epoxyhexadecane was dissolved in 2 ml of tetrahydrofuran, to this solution was added 0.5 ml of 5% perchloric acid aqueous solution and the mixture was stirred at room temperature for 4 hours. Then, 30 ml of diethyl ether was added to the reaction mixture, and the organic layer was washed with a saturated sodium chloride aqueous solution in several times, and dried over anhydrous sodium sulfate. This extract was purified by means of a preparative thin layer chromatography [adsorbent: "Silica gel 60 F$_{254}$" manufactured by E. Merck A. G., developing solvent: chloroform-methanol (85:15 mixture by volume/volume)], then recrystallized from ethyl acetate-n-hexane to obtain 12 mg of 1,16-bis(5-methoxy-2-hydroxy-1,4-benzoquinon-3-yl)-8,9-dihydroxyhexadecane. Yellow powdery crystals.

Melting point: 132°–134° C.

PMR, $\delta_{ppm}^{CDCl_3}$ (400 MHz): 1.2–1.5 (24H), 2.01 (2H, brs), 2.44 (4H, t, J=7.3Hz), 3.40 (2H, brs), 3.86 (6H, s), 5.83 (2H, s), 7.30 (2H, brs).

Mass spectrometry m/z 562 (M+) 544, 516, 282, 193, 169, 153, 139.

EXAMPLE 9

12 Milligrams of 1,16-bis(5-methoxy-2-hydroxy-1,4-benzoquinon-3-yl)-Z-8-hexadecene was dissolved in 3 ml of methanol-diethyl ether (1:1 mixture by volume/volume), to this solution was added 0.5 ml of 2% diazomethan diethyl ether solution under an ice-cooling condition. The reaction mixture was treated on a preparative thin layer chromatography [adsorbent: "Silica gel 60 $F_{254}$" manufactured by E. Merck A. G., developing solvent: benzene-ethyl acetate (5:1 mixture by volume/volume)] to obtain 10 mg of 1,16-bis(2,5-dimethoxy-1,4-benzoquinon-3-yl)-Z-8-hexadecene. Yellow oily substance.

PMR, $\delta_{ppm}^{CDCl_3}$ (400 MHz): 1.2–1.5 (20H), 1.99 (4H, m), 2.42 (4H, t, J=7.5Hz), 3.80 (6H, s), 4.04 (6H, s), 5.33 (2H, m), 5.72 (2H, s).

Mass spectometry m/z 556 (M+): 374, 207, 193, 183, 169, 167, 153.

EXAMPLE 10

9 Milligrams of 1,16-bis(2,5-dimethoxy-1,4-benzoquinon-3-yl)-cis-8-hexadecene was dissolved in 1 ml of methylene chloride, then to this solution was added 8 mg of m-chlorobenzoic acid and the mixture was stirred at room temperature for 1 hour. After the completion of the reaction, the solvent was removed by evaporation under reduced pressure, and the residue obtained was purified by means of a preparative thin layer chromatography [adsrobent: "Silica gel 60 $F_{254}$" manufactured by E. Merck A. G., developing solvent: benzene-ethyl acetate (5:1 mixture by volume/volume)] to obtain 3 mg of 1,16-bis(2,5-dimethoxy-1,4-benzoquinon-3-yl)-8,9-epoxyhexadecane. Yellow oily substance.

PMR, $\delta_{ppm}^{CDCl_3}$ (200 MHz): 1.2–1.5 (24H), 2.43 (4H, t, J=7.3Hz), 2.89 (2H, m), 3.80 (6H, s), 4.05 (6H, s), 5.73 (2H, s).

Mass spectometry m/z 572 (M+) 207, 193, 183, 169, 167, 153, 139.

EXAMPLE 11

36 Milligrams of 1-(2-hydroxy-5-methoxy-1,4-benzoquinon-3-yl)-16-(2-hydroxy-5-methoxy-6-methyl-1,4-benzoquinon-3-yl)-Z-8-hexadecene was dissolved in 10 ml of diethyl ether, to this solution was added 0.5 ml of 2% diazomethane diethyl ether solution under an ice-cooling condition to conduct methylation. Next, the reaction mixture was treated on a preparative thin layer chromatography [adsorbent: "Silica gel 60 $F_{254}$" manufactured by E. Merck A. G., developing solvent: benzene-ethyl acetate (5:1 mixture by volume/volume)] to obtain 29 mg of 1-(2,5-dimethoxy-1,4-benzoquinon-3-yl)-16-(2,5-dimethoxy-6-methyl-1,4-benzoquinon-3-yl)-Z-8-hexadecene. Yellow oily substance.

PMR, $\delta_{ppm}^{CDCl_3}$ (400 MHz): 1.2–1.5 (20H, m), 1.91 (3H, s), 2.00 (4H, brs), 2.39 (2H, t, J=7.0Hz), 2.42 (2H, t, J=7.6Hz), 3.80 (3H, s), 3.98 (3H, s), 3.99 (3H, s), 4.04 (3H, s), 5.33 (2H, m), 5.72 (1H, s).

Mass spectormetry m/z 570 (M+) 197, 183, 167, 153, 147, 123.

EXAMPLE 12

25 Milligrams of 1-(2,5-dimethoxy-1,4-benzoquinon-3-yl)-16-(2,5-dimethoxy-6-methyl-1,4-benzoquinon-3-yl)-Z-8-hexadecene was dissolved in 2 ml of methylene chloride, then to this solution was added 30 mg of m-chlorobenzoic acid and the reaction mixture was stirred at room temperature for 1 hour. After the reaction was completed the solvent was removed by evaporation under reduced pressure, then the residue obtained was purified by means of a preparative thin layer chromatography [adsorbent: "Silica gel $F_{254}$" manufactured by E. Merck A. G., developing solvent: benzene-ethyl acetate (5:1 mixture by volume/volume)] to obtain 9 mg of 1-(2,5-dimethoxy-1,4-benzoquinon-3-yl)-16-(2,5-dimethoxy-6-methyl-1,4-benzoquinon-3-yl)-8,9-epoxyhexadecane. Yellow oily substance.

PMR, $\delta_{ppm}^{CDCl_3}$ (400 MHz): 1.2–1.5 (24H), 1.91 (3H, s), 2.41 (4H, m), 2.89 (2H, brs), 3.80 (3H, s), 3.98 (3H, s), 3.99 (3H, s), 4.04 (3H, s), 6.71 (1H, s).

Mass spectometry m/z 586 (M+) 568, 221, 207, 197, 183, 167, 153, 137.

EXAMPLE 13

By using 4 mg of 2-hydroxy-5-methoxy-3-(Z-10 pentadecenyl)-1,4-benzoquinon and by a method similar to that described in Example 9, there was prepared 4 mg of 2,5-dimethoxy-3-(Z-10-pentadecenyl)-1,4-benzoquinone. Yellow oily substance.

PMR, $\delta_{ppm}^{CDCl_3}$ (200 MHz): 0.89 (3H, t, J=7.0Hz), 1.2–1.5 (18H), 2.01 (4H, m), 2.42 (2H, t, J=7.6Hz), 3.80 (3H, s), 4.04 (3H, s), 5.34 (2H, m), 5.72 (1H, s).

Mass spectrometry m/z 376 (M+) 183, 169, 167, 153, 123.

EXAMPLE 14

By using 4 mg of 2,5-dimethoxy-3-(Z-10-pentadecenyl)-1,4-benzoquinone and using a method similar to that described in Example 10, there was prepared 3 mg of 1-(2,5-dimethoxy-1,4-benzoquinon-3-yl)-10,11-epoxypentadecane. Yellow oily substance.

PMR, $\delta_{ppm}^{CDCl_3}$ (200 MHz): 0.92 (3H, t, J=6.8Hz), 1.2–1.5 (22H), 2.42 (2H, t, J=7.0Hz), 2.91 (2H, m), 3.81 (3H, s), 4.05 (3H, s), 5.73 (1H, s).

Mass spectrometry m/z 392 (M+): 374, 306, 181, 169, 168, 167, 153, 139.

EXAMPLE 15

By using 3 mg of 2-hydroxy-5-methoxy-3-(Z-8-tridecenyl)-1,4-benzoquinone, and by a method similar to that described in Example 9, there was prepared 3 mg of 2,5-dimethoxy-3-(Z-8-tridecenyl)-1,4-benzoquinone. Yellow oily substance.

PMR, $\delta_{ppm}^{CDCl_3}$ (200 MHz): 0.86 (3H, t, J=7.0Hz), 1.2–1.5 (14H), 2.01 (4H, m), 2.42 (2H, t, J=7.3Hz), 3.80 (3H, s), 4.04 (3H, s), 5.33 (2H, m), 5.72 (1H, s).

Mass spectrometry m/z 348 (M+) 183, 169, 167, 153, 123.

EXAMPLE 16

By using 3 mg of 2,5-dimethoxy-3-(Z-8-tridecenyl)1,4-benzoquinone, and by a method similar to that described in Example 10, there was prepared 2 mg of 1-(2,5-dimethoxy-1,4-benzoquinon-3-yl)-8,9-epoxytridecane. Yellow oily substance.

PMR, $\delta_{ppm}^{CDCl_3}$ (400 MHz): 0.92 (3H, t, J=7.3Hz), 1.2–1.5 (18H), 2.43 (2H, t, J=7.3Hz), 2.90 (2H, m), 3.80 (3H, s), 4.05 (3H, s), 5.73 (1H, s).

Mass spectometry m/z 364 (M+): 346, 183, 169, 168, 167, 153, 139.

EXAMPLE 17

By using 6 mg of 2,5-dimethoxy-3-(Z-8-heptadecenyl)-1,4-benzoquinone, and by a method similar to that described in Example 10, there was prepared 3 mg of 1-(2,5-dimethoxy-1,4-benzoquinone-3-yl)-8,9-epoxyheptadecane. Yellow oily substance.

PMR, $\delta_{ppm}{}^{CDCl_3}$ (400 MHz): 0.88 (3H, t, J=6.8Hz, 1.2–1.5 (26H), 2.43 (2H, t, J=7.3Hz), 2.90 (2H, m), 3.81 (3H, s), 4.05 (3H, s), 5.73 (1H, s).

Mass spectrometry m/z: 420, 402, 183, 169, 167, 153, 139.

EXAMPLE 18

1.0 Gram of 1-methoxymethoxy-2-[2,5-dimethoxy-3,6-bis(methoxymethoxy)phenyl]ethane was dissolved in a mixed solvent of 20 ml of toluene with 5 ml of hexamethylphosphoric triamide, to this solution was added 0.52 ml of N,N,N',N'-tetramethylethylenediamine and the whole mixture was cooled to −78° C. in a dry ice-acetone bath, then 2.7 ml of n-butyllithium (1.6 mole solution) was added dropwise to the reaction mixture. 15 Minutes later, a solution prepared by dissolving 1.56 g of 1-(5-iodopent-1-yl)-2,5-dimethoxy-3,6-bis(methoxymethoxy)benzene in 12 ml of toluene was added to the reaction mixture, and the temperature of the reaction mixture was gradually elevated to room temperature and the reaction mixture was stirred further for 4 hours. 50 Milliliters of diethyl ether was added to the reaction mixture, and the organic layer was washed with water, and with a saturated sodium chloride aqueous solution, then dried over anhydrous sodium sulfate. After concentration, the residue thus obtained was purified by means of a silica gel column chromatography (diameter 3 cm×length 10 cm, Merck, eluent: 30% ethyl acetate-n-hexane) to obtain 2.1 g of 1-[2,5-dimethoxy-3,6-bis(methoxymethoxy)phenyl]-5-[2,5-dimethoxy-3,6-bis(methoxymethoxy)-4-(2-methoxymethyloxyethyl)phenyl]pentane. Amorphous powdery substance.

PMR, $\delta$ppm (CDCl$_3$) 1.7–1.45 (6H, m), 2.75–2.55 (4H, m), 2.98 (2H, t, J=7.0Hz), 3.30 (3H, s), 3.54 (3H, s), 3.57 (3H, s), 3.58 (3H, s), 3.60 (3H, s), 3.72 (2H, t, J=7.0Hz), 3.75 (3H, s), 3.79 (9H, s), 4.63 (2H, s), 5.03 (2H, s), 5.05 (2H, s), 5.07 (2H, s), 5.18 (2H, s), 6.65 (1H, s).

EXAMPLE 19

560 Milligrams of 1-[2,5-dimethoxy-3,6-bis(methoxymethoxy)phenyl]-5-[2,5-dimethoxy-3,6-bis(methoxymethoxy)-4-(2-methoxymethyloxyethyl)phenyl]pentane was dissolved in a mixed solvent of 20 ml of tetrahydrofuran with 4 ml of hexamethylphosphoric triamide, then to this solution was added 0.15 ml of N,N,N',N'-tetramethyl diamine and the whole mixture was cooled to −78° C. in a dry ice-acetone bath, then 0.8 ml of n-butyllithium was added to the reaction mixture. 15 Minutes later, oxygen gas was blown into the reaction mixture for about 30 minutes. Temperature of the reaction mixture was gradually elevated to a room temperature, and the reaction mixture was further stirred for 4 hours. The reaction mixture was concentrated and to the residue obtained was added 50 ml of ethyl acetate, and was washed twice with a saturated sodium hydrogen sulfite aqueous solution, further washed once with water and with a saturated sodium chloride aqueous solution, and dried over anhydrous magnesium sulfate. This ethyl acetate solution was concentrated to obtain 530 mg of the residue which was then dissolved in 4 ml of methanol, to this methanol solution was added a diethyl ether solution of diazomethane under an ice-cooled condition, then this reaction mixture was allowed to stand for 3 hours and concentrated. The residue obtained was treated by means of a preparative thin layer chromatography (adsorbent: "Silica gel" manufactured by E. Merck A. G., dimentions: 20 cm×20 cm×thickness 2 mm, 2 plates were used, developing solvent: 50% ethyl acetate-n-hexane) to obtain 1-[2,4,5-trimethoxy-3,6-bis(methoxymethoxy)phenyl]-5-[2,5-dimethoxy-3,6-bis(methoxymethoxy)-4-(2-methoxymethyloxyethyl)phenyl]pentane. Amorphous powder.

PMR, $\delta$ ppm (CDCl$_3$) 1.7–1.4 (6H, m), 2.7–2.5 (4H, m), 2.99 (2H, t, J=6.3Hz), 3.31 (3H, s), 3.59 (6H, s), 3.61 (3H, s), 3.62 (3H, s), 3.72 (2H, t, J=6.3Hz), 3.78 (3H, s), 3.80 (3H, s), 3.82 (3H, s), 3.83 (3H, s), 3.90 (3H, s), 4.64 (2H, s), 5.04 (2H, s), 5.07 (2H, s), 5.08 (2H, s), 5.09 (2H, s).

EXAMPLE 20

503 Milligrams of 1-[2,4,5-trimethoxy-3,6-bis(methoxymethoxy)phenyl]-5-[ 2,5-dimethoxy-3,6-bis(methoxymethoxy)-4-(2-methoxymethyloxyethyl)phenyl]pentane was dissolved in a mixed solvent of 5 ml of tetrahydrofuran with 5 ml of isopropanol, to this solution was added 1 milliliter of tetrahydrofuran-isopropanol (1:1) solution of 20%-hydrogen chloride, and the whole mixture was stirred for 12 hours. After concentrated the reaction mixture, the residue was treated by an azeotropic distillation with benzene, then dissolved in 8 ml of methanol, further a small amount of sodium hydrogen carbonate was added thereto, and oxygen gas was blown into the solution. 2 Hours later, the solution was concentrated, and 50 ml of dichloromethane was added, then washed with water and a saturated sodium chloride aqueous solution, and dried over anhydrous magnesium sulfate. After concentrated, the residue was re-crystallized from diethyl ether to obtain 123 mg of 2-(2,5,6-trimethoxy)-1,4-benzoquinon-3-yl)-5-[2,5-dimethoxy-6(2-hydroxyethyl)-1,4-benzoquinon-3-yl]pentane. Yellow crystals.

Melting point 65°–67° C.

PMR, $\delta$ ppm (CDCl$_3$) 1.45–1.3 (6H, m), 2.45–2.35 (4H, m), 2.73 (2H, t, J=5.2Hz), 3.72 (2H, t, J=5.2Hz), 3.99 (3H, s), 4.02 (3H, s), 4.03 (3H, s), 4.04 (3H, s), 4.06 (3H, s).

EXAMPLE 21

550 Milligrams of 1-[2,5-dimethoxy-3,6-bis(methoxymethoxy)phenyl]-5-[2,5-dimethoxy-3,6-bis(methoxymethoxy)-4-(2-methoxymethyloxyethyl)phenyl]pentane was dissolved in a mixed solvent of 8 ml of toluene with 2 ml of hexamethylphosphoric triamide, to this solution was added 0.12 ml of N,N,N',N'-tetramethylethylenediamine and the whole mixture was cooled to −78° C. in a dry ice-acetone bath, then 0.64 ml of n-butyllithium was added to the reaction mixture. 15 Minutes later, 0.16 ml of n-butyl iodide was added to the reaction mixture, and temperature of the reaction mixture was gradually elevated to room temperature, and further stirred for 4 hours. 50 Milliliters of diethyl ether was added to the reaction mixture, and the organic layer was washed with water, a saturated sodium chloride aqueous solution, dried over anhydrous magnesium sulfate, and then concentrated. The residue obtained was purified by means of a silica gel column chromatography (diameter 2 cm×length 10 cm, adsorbent: "Silica gel 60" manufactured by E. Merck A. G., developing solvent: 30% ethyl acetate-hexane) to obtain 520 mg of 1-[2,5-dimethoxy-4-butyl-3,6-bis(methoxymethoxy)-phenyl]-5-[2,5-dimethoxy-3,6-bis(methoxymethoxy)4-(2-methoxymethyloxyethyl)phenyl]pentane. Amorphous powdery substance.

PMR, $\delta$ ppm (CDCl$_3$) 0.96 (3H, t, J=6.8Hz), 1.7–1.2 (10H, m), 2.7–2.5 (6H, m), 2.98 (2H, t, J=7.0Hz), 3.30 (3H, s), 3.56 (3H, s), 3.57 (3H, s), 3.58 (3H, s), 3.59 (3H, s), 3.70 (2H, t, J=7.0Hz), 3.76 (3H, s), 3.77 (6H, s), 3.97 (3H, s), 4.62 (2H, s), 5.03 (2H, s), 5.04 (2H, s), 5.07 (2H, s).

EXAMPLE 22

520 Milligrams of 1-[2,5-dimethoxy-4-butyl-3,6-bis(-methoxymethoxy)phenyl]-5-[2,5-dimethoxy-3,6-bis(methoxymethoxy)-4-(2-methoxymethyloxyethyl)phenyl]pentane was dissolved in 5 ml of tetrahydrofuran with 5 ml of isopropanol, to this solution was added 1 milliliter of tetrahydrofuran-isopropanol (1:1) solution of 20%-hydrogen chloride, and the whole mixture was stirred at room temperature for 12 hours. After concentrated the reaction mixture, the residue obtained was treated by an azeotrotic distillation with benzene, then dissolved in 8 ml of methanol, further a small amount of sodium hydrogen carbonate was added thereto, and oxygen gas was blown into the solution for 2 hours. This solution was concentrated, and 50 ml of dichloromethane was added to the residue and the solution was washed with water and with a saturated sodium chloride aqueous solution, and concentrated. Then this product was purified by means column chromatography (diameter 2 cm×length 10 cm, adsorbent: "Silica gel 60" manufacture by E. Merck A. G., developing solvent: 30% ethyl acetate-n-hexane) to obtain 231 mg of 1-(2,5-dimethoxy-6-butyl-1,4-benzoquinone-3-yl)-5-[2,5-dimethoxy-6-(2-hydroxyethyl)-1,4-benzoquinon-3-yl]pentane. Amorphous powdery substance.

PMR, $\delta$ ppm (CDCl$_3$): 1.92 (3H, t, J=4.1Hz), 1.5–1.25 (10H, m), 2.40 (6H, m), 2.74 (2H, t, J=4.3Hz), 3.73 (2H, t, J=4.3Hz), 3.97 (3H, s), 3.98 (3H, s), 3.99 (3H, s), 4.40 (3H, s).

EXAMPLE 23

530 Milligrams of 1-[2,5-dimethoxy-3,6-bis(methoxymethoxy)phenyl]-5-[2,5-dimethoxy-3,6-bis(methoxymethoxy)-4-(2-methoxymethyloxyethyl)phenyl]pentane was dissolved in a mixed solvent of 8 ml of toluene with 2 ml of hexamethylphosphoric triamide, to this solution was added 0.11 ml of N,N,N',N'-tetramethylethylenediamine, and the whole mixture was cooled to −78° C. in a dry ice-acetone bath, then 0.62 ml of n-butyllithium was added to the reaction mixture. 15 Minutes later, 0.14 ml of ethyl chloroformate was added to the reaction mixture, and temperature of the reaction mixture was elevated gradually to a room temperature, and further stirred for 5 hours. 50 Milliliters of ethyl acetate was added to the reaction mixture, and washed with water, a saturated sodium chloride aqueous solution, then dried over anhydrous magnesium sulfate, concentrated to obtain 498 mg of the residue. 498 Milligrams of this residue was dissolved in a mixed solvent of 5 ml of ethanol with 5 ml of tetrahydrofuran, to this solution was added 1 milliliter of tetrahydrofuran-ethanol (1:1) solution of 20%-hydrogen chloride and the mixture was stirred for 12 hours. After concentrated the reaction mixture, the residue was treated by azeotropic distillation with benzene, then dissolved in 8 ml of acetonitrile, and to this solution was added a small amount of Cu$_4$Cl$_4$O$_2$ (CH$_3$CN)$_3$, then oxygen gas was blown into the reaction mixture for 2 hours. After the reaction mixture was filtered, then the filtrate was concentrated, to the residue obtained was added 50 ml of dichloromethane, then washed with water and with a saturated sodium chloride aqueous solution, and dried over anhydrous magnesium sulfate and concentrated. The residue obtained was purified by means of a preparative thin layer chromatography (adsorbent: "Silica gel" manufactured by E. Merck A. G., dimentions 20 cm×20 cm, thickness 2 mm, 2 plates were used, developing solvent: 10%-ethyl acetate-n-hexane) to obtain 102 mg of 1-(2,5-dimethoxy-6-ethoxycarbonyl)-1,4-benzoquinon-3-yl)-5-[2,5-dimethoxy-6-(hydroxyethyl)-1,4-benzoquinon-3-yl]pentane. Amorphous powdery substance.

PMR, $\delta$ ppm (CDCl$_3$): 1.38 (3H, t, J=7.1Hz), 1.40 (6H, m), 2.41 (4H, m), 2.72 (2H, t, J=6.8Hz), 3.72 (2H, t, J=6.8Hz), 4.00 (3H, s), 4.05 (6H, s), 4.06 (3H, s), 4.37 (2H, q, J=7.1Hz).

EXAMPLE 24

560 Milligrams of 1-[2,5-dimethoxy-3,6-bis(methoxymethoxy)phenyl]-5-[2,5-dimethoxy-3,6-bis(methoxymethoxy)-4-(2-methoxymethoxy)phenyl]pentane was dissolved in a mixed solvent of 20 ml of tetrahydrofuran with 4 ml of hexamethylphosphoric triamide, to this solution was added 0.15 ml of N,N,N',N'-tetramethylethylenediamine, and the whole mixture was cooled to −78° C. in a dry ice-acetone bath, then 0.80 ml of n-butyllithium was added to the reaction mixture, and temperature of the reaction mixture was gradually elevated to room temperature, and further stirred for 5 hours. 50 Milliliters of ethyl acetate was added to the reaction mixture, and the organic layer was washed with water and with a saturated sodium chloride aqueous solution, then dried over anhydrous magnesium sulfate, and concentrated. The residue obtained was purified by means of a silica gel column chromatography (diameter 2 cm×length 10 cm, adsorbent: "Silica gel" manufactured by E. Merck A. G., developing solvent: 30% ethyl acetate-n-hexane) to obtain 503 mg of 1-[2,5-dimethoxy-3,6-bis(methoxymethoxy)-4-methylthiophenyl]-5-(2,5-dimethoxy-3,6-bis(methoxymethoxy)-4-(2methoxymethoxyethylphenyl]pentane. Colorless oily substance.

PMR, $\delta$ ppm (CDCl$_3$): 1.7–1.4 (6H, m), 2.33 (3H, s), 2.7–2.4 (4H, m), 2.93 (2H, t, J=8.1Hz), 3.24 (3H, s), 3.54 (6H, s), 3.57 (3H, s), 3.68 (3H, s), 3.69 (3H, s), 3.70 (3H, s), 3.72 (3H, s), 4.52 (2H, s), 5.01 (2H, s), 5.03 (4H, s), 5.07 (2H, s).

EXAMPLE 25

503 Milligrams of 1-[2,5-dimethoxy-3,6-bis(methoxymethoxy)-4-methylthiophenyl]-5-[2,5-dimethoxy3,6-bis(methoxymethoxy)-4-(2-methoxymethoxyethyl)-phenyl]pentane was dissolved in a mixed solvent of 5 ml of tetrahydrofurn with 5 ml of isopropanol, to this solution was added 1 milliliter of tetrahydrofuran-isopropanol (1:1) solution of 20%-hydrogen chloride and the whole mixture was stirred for 12 hours. After concentrated the reaction mixture, the residue obtained was treated by azeotropic distillation with benzene, and dissolved in 8 ml of methanol, a small amount of sodium hydrogen carbonate was added thereto, then oxygen gas was blown into the solution. After concentrated this solution, the residue obtained was dissolved in 50 ml of dichloromethane, then washed with water, and with a saturated sodium chloride aqueous solution, and concentrated. The residue obtained was purified by means of a preparative thin layer chromatography (adsorbent: "Silica gel" manufactured by E. Merck A. G., developing solvent: 30% ethyl acetatehexane) to obtain 23.6 mg of 1-(2,5-dimethoxy6-methylthio-1,4-benzoquinon-3-yl)-5-[2,5-dimethoxy-6-(2-hydroxyethyl)1,4-benzoquinon-3-yl]pentane. Amorphous powdery substance.

PMR, δ ppm (CDCl$_3$) 1.55–1.4 (6H, m), 2.45–2.23 (4H, m), 2.48 (3H, s), 2.72 (2H, t, J=7.6Hz), 3.70 (2H, t, J=7.6Hz), 3.98 (6H, s), 4.02 (3H, s), 4.06 (3H, s).

EXAMPLE 26

521 Milligrams of 1,4-dimethoxy-2,5-bis(methoxymethyoxy)-3-hydroxybenzene was dissolved in 8 ml of dimethylformamide, under an ice-cooling condition, 40 mg of sodium hydride (60% dispersion in oil) was added thereto, and 1 milliliter of 1,3-diiodopropane was further added to the reaction mixture and stirred at room temperature for 14 hours. 50 Milliliters of ethyl acetate was added to the reaction mixture and washed with water, a saturated sodium chloride aqueous solution and dried, then purified by means of a silica gel column chromatography (diameter 2 cm×length 10 cm, adsorbent: "Silica gel" manufactured by E. Merck A. G., developing solvent: 20% ethyl acetate-n-hexane) to obtain 318 mg of 1,4-dimethoxy-2,5-bis(dimethoxymethoxy)-3-(3-iodopropoxy)benzene. Colorless oily substance.

PMR, δ ppm (CDCl$_3$) 2.23 (2H, tt, J=5.6, 7.5), 3.42 (2H, t, J=7.5Hz), 3.53 (3H, s), 3.60 (3H, s), 3.91 (3H, s), 3.93 (3H, s), 4.13 (2H, t, J=5.6Hz), 5.06 (2H, s), 5.17 (2H, s), 6.55 (1H, s).

EXAMPLE 27

403 Milligrams of 1,4-dimethoxy-2,5-bis(methoxymethoxy)-3-hydroxybenzene was dissolved in 6 ml of dimethylformamide, under an ice-cooling condition a small amount of sodium hydride was added thereto, and 318 mg of 1,4-dimethoxy-2,5-bis(methoxymethoxy)-3-(iodopropoxy)benzene was added to the reaction mixture and stirred at room temperature for 14 hours. 50 Milliliters of ethyl acetate was added to the reaction mixture, and washed with water and with a saturated sodium chloride aqueous solution, then dried over anhydrous magnesium sulfate. This solution was concentrated and the residue obtained was purified by means of a silica gel column chromatography (diameter 2 cm×length 10 cm, adsorbent: "Silica gel" manufactured by E. Merck A. G., eluent: 40% ethyl acetate-n-hexane) to obtain 523 mg of 3,3-trimethylenedioxy-bis[1,4-dimethoxy-2,5-bis(methoxymethoxy)benzene]. Amorphous powdery substance.

PMR, δ ppm (CDCl$_3$) 2.17 (2H, quintet, J=7.5Hz), 3.52 (6H, s), 3.59 (6H, s), 3.80 (6H, s), 3.81 (6H, s), 4.29 (4H, t, J=7.5 Hz), 5.07 (4H, s), 5.18 (4H, s), 6.56 (2H, s).

EXAMPLE 28

523 Milligrams of 3,3-trimethylenedioxy-bis[1,4-dimethoxy-2,5-bis(methoxymethoxy)benzene] was dissolved in a mixed solvent of 5 ml of tetrahydrofuran with 5 ml of isopropanol, to this solution was added 1 milliliter of tetrahydrofuran-isopropanol (1:1) solution of 20%-hydrogen chloride and the whole mixture was stirred for 12 hours. After concentrated the reaction mixture, the residue obtained was treated by azeotropic distillation with benzene, then was dissolved in 8 ml of methanol, further a small amount of sodium hydrogen carbonate was added thereto, then oxygen gas was blown into the solution for 2 hours. After concentrated, 50 ml of dichloromethane was added to the residue obtained, and washed with water, a saturated sodium chloride aqueous solution and dehydrated with anhydrous magnesium sulfate. This solution was concentrated and recrystallized from methanol to obtain 231 mg of 3,3-trimethylenedioxy-bis(2,5-dimethoxy-1,4-benzoquinone). Yellow crystals.

Melting point: 144°–145° C.

PMR, δ ppm (CDCl$_3$) 2.22 (2H, quintet, J=8.2Hz), 3.79 (6H, s), 4.10 (6H, s), 4.27 (4H, t, J=8.2Hz), 5.73 (2H, s).

EXAMPLE 29

100 Milligrams of 3,3'-pentamethylene-bis(2,5-diamino-1,4-benzoquinone) was dissolved in 6 ml of methanol, and 1 milliliter of ammonia water (28%) was added to the solution and stirred for 5 hours. The reaction mixture was concentrated, and recrystallized from methanol to obtain 21.3 mg of 2,2'-pentamethylenebis(3,6-diamino-p-benzoquinone). Reddish violet crystals.

Melting point: over 250° C.

PMR, δ ppm (DMSO-d$_6$) 1.24 (6H, m), 2.18 (4H, m), 5.25 (2H, s).

EXAMPLE 30

(1) 5 Grams of 1,4-dimethoxy-2,5-bis(methoxymethoxy)benzene was dissolved in 140 ml of tetrahydrofuran, then the solution was cooled to −78° C. under argon gas stream condition, in a dry ice-acetone bath. Then 18 ml of sec-butyllithium (1.3 mole cyclohexane solution) was added dropwise thereto and stirred for 30 minutes. To the reaction mixture was added dropwise 10 g (6.7 ml) of 1,7-dibromoheptane, next 6 g of sodium iodide and 10 ml of hexamethylphosphoric triamide were added to the reaction mixture. The cooling bath was removed from the reaction apparatus, and the reaction mixture was stirred at room temperature for 12–14 hours. Tetrahydrofuran was removed by evaporation under reduced pressure, the residue obtained was dissolved in 500 ml of a mixed solvent benzene-diethyl ether (1:1). The organic layer was washed with 100 ml of water in 4 times, and with 100 ml of saturated sodium chloride aqueous solution in 4 times, and dried over anhydrous magnesium sulfate. After the removal of the solvent by evaporating under reduced pressure, the residue obtained was treated by means of a silica gel column chromatography (diameter 5 cm×length 30 cm, adsorbent: "Wakol-C200") and developed and eluted with 20%-ethyl acetate-n-hexane to obtain 6.06 g (yield=72%) of 1-bromo-7-[2,5-dimethoxy-3,6-bis(methoxymethoxy)phenyl]heptane. Colorless oily substance.

PMR, δ$_{ppm}$$^{CDCl3}$: 1.2–1.65 (8H, brm), 1.82 (2H, brm), 2.67 (2H, brt, J=6.9Hz), 3.40 (2H, t, J=6.8Hz), 3.53 (3H, s), 3.58 (3H, s), 3.79 (6H, s), 5.02 (2H, s), 5.17 (2H, s), 6.65 (1H, s).

(2) To 17 ml of 1-hexyne was added 20 ml of anhydrous tetrahydrofuran, and was cooled to −78° C. under argon gas stream condition. Then 4.7 ml of n-butyllithium (1.6 mole n-hexane solution) was added dropwise to the above-mentioned cooled solution and the whole mixture was stirred for 30 minutes. A solution prepared by dissolving 2.17 g of 1-bromo-7-[2,5-dimethoxy-3,6-bis(methoxymethoxy)phenyl]heptane obtained in the above-mentioned process (1) in 5 ml of anhydrous tetrahydrofuran was added dropwise to the mixture, then 2 ml of hexamethylphosphoric triamide was added thereto. The cooling bath was removed from the reaction apparatus, and the reaction mixture was continuously stirred at room temperature for 4 hours. Tetrahydrofuran was removed by evaporation under reduced pressure, to the residue obtained was added 300 ml of a mixed solvent of benzene-diethyl ether (1:1), the organic layer was washed 4 times with water, and further washed 4 times with a saturated sodium chloride aqueous solution, then dried over anhydrous magnesium sulfate, and concentrated, to yield 2.2 g (almost about 100%) of 1-[2,5-dimethoxy-3,6-bis(methoxymethoxy)phenyl]tridec-8-yne. Colorless oily substance.

PMR, $\delta_{ppm}^{CDCl_3}$: 0.89 (3H, t, J=7.3Hz), 1.25–1.65 (14H, brm), 2.12 (4H, brm), 2.65 (2H, brm, J=7.8Hz), 3.52 (3H, s), 3.57 (3H, s), 3.78 (6H, s), 5.01 (2H, s), 5.16 (2H, s), 6.63 (1H, s).

(3) 1 Gram of 1-[2,5-dimethoxy-3,6-bis(methoxymethoxy)phenyl]tridec-8-yne prepared in the above-mentioned (2) was dissolved in 10 ml of methanol, to this solution was added 40 mg of 5%-palladium-barium sulfate-quinoline (1:1) and the mixture was catalytically reduced under a normal hydrogen pressure at room temperature for 4 hours. This reaction was traced by means of a high performance liquid chromatography. Thus, the reaction was determined by measuring the optical density (OD) at $UV_{254}$ under conditions of ODS column, 80%-acetonitrile-water, 2 ml/minute. After the reaction was completed, the catalyst was removed by filtration, and methanol was removed by evaporation under reduced pressure, and the residue obtained was treated by means of a column chromatography ("Robar" column, LiChrosorb RP-8, Type C, manufactured by E. Merck A. G.) and eluted with 75%-acetonitrile-water at the flow rate of 5 ml/minute to obtain both Z-isomer and E-isomer, respectively. There was obtained 0.65 g of 1-[2,5-dimethoxy-3,6-bis-Imethoxymethoxy)phenyl]tridec-8-ene (Z-isomer) as in the form of colorless oily substance.

PMR, $\delta_{ppm}^{CDCl_3}$: 0.89 (3H, t, J=7.3Hz), 1.2–1.65 (14H, brm), 2.01 (4H, brm), 2.66 (2H, brt, J=7.3Hz), 3.53 (3H, s), 3.58 (3H, s), 3.78 (6H, s), 5.02 (2H, s), 5.17 (2H, s), 5.34 (2H, m), 6.63 (1H, s).

(4) 500 Milligrams of the compound obtained in the above-mentioned (3) was dissolved in 20 ml of methanol, and to this solution was added 2 ml of isopropanol-tetrahydrofuran mixed solvent solution of 20%-hydrogen chloride, under nitrogen gas stream condition at room temperature and the mixture was stirred for 3 hours. The solvent was removed by evaporation under reduced pressure at a temperature below 20° C. on a bath, further 20 ml of benzene was added thereto, and the mixture was concentrated under a reduced pressure to remove hydrogen chloride. To the residue thus obtained was added 20 ml of methanol and air or oxygen gas was blown into this methanol solution for 1 to 2 hours during the reaction vessel is heated at 60° C. on a water bath, the color of the methanol solution turned yellow. Methanol was removed by evaporation under reduced pressure to concentrate the solution, the residue thus obtained was treated by a thin layer chromatography ("Silica gel TLC, $F_{254}$", manufactured by E. Merck A. G., thickness: 2 mm), developed with 10%-ethyl acetate-benzene, and eluted with ethyl acetate to obtain 300 mg (yield=75%) of 2,5-dimethoxy-3-(Z-8-tridecenyl)-1,4-benzoquinone as in the form of yellow oily substance. The physical properties of this compound were identical to those shown by the compound prepared in Example 15 as mentioned above.

(5) By using procedures similar to those described in the above-mentioned Example 30 (2), except that 1-bromo-5-[2,5-dimethoxy-3,6-bis(methoxymethoxy)-phenyl]pentane was used in place of 1-bromo-7-[2,5-dimethoxy-3,6-bis methoxymethoxy)phenyl]heptane, there was obtained 1,4-dimethoxy-2,5-bis(methoxymethoxy)-3-(6-undecynyl)benzene. Colorless oily substance.

PMR, $\delta$ ppm (CDCl$_3$): 0.90 (3H, t, J=7.0Hz), 1.6–1.35 (10H, m), 2.14 (4H, brm), 2.67 (2H, t, J=8.1Hz), 3.53 (3H, s), 3.59 (3H, s), 3.79 (6H, s), 5.02 (2H, s), 5.17 (2H, s), 6.64 (1H, s).

(6) By using procedures similar to those described in the above-mentioned Example 30 (4), except that 1,4-dimethoxy-2,5-(methoxymethoxy)-3-(6-undecynyl)benzene prepared in the above-mentioned Example 30 (5) was treated under conditions of the removal of protecting group and of the oxidation, there was obtained 2,5-dimethoxy-3-(6-undecynyl)-1,4-benzoquinone. Yellow oily substance.

PMR, $\delta$ ppm (CDCl$_3$) 0.90 (3H, t, J=7.0Hz), 1.42 (10H, brm), 2.13 (4H, m), 2.43 (2H, t, J=7.3Hz), 3.80 (3H, s), 4.05 (3H, s), 5.72 (1H, s).

(7) By using procedures similar to those described in the above-mentioned Example 30 (4), except that 1-[2,5-dimethoxy-3,6-bis(methoxymethoxy)phenyl]-tridec-8-yne prepared in the above-mentioned Example 30 (2) was treated, there was obtained 2,5-dimethoxy-3-(8-tridecynyl)-1,4-benzoquinone. Yellow oily substance.

PMR, $\delta$ ppm (CDCl$_3$) 0.90 (3H, t, J=7.0Hz), 1.5–1.25 (14H, m), 2.13 (4H, m), 2.43 (2H, t, J=7.0Hz), 3.80 (3H, s), 4.05 (3H, s), 5.72 (1H, s).

(8) 500 Milligrams of 1,4-dimethoxy-2,5-bis(methoxymethoxy)-3-(Z-6-undecenyl)benzene was dissolved in 10 ml of a mixed solvent of isopropanol-tetrahydrofuran, and at room temperature, under nitrogen gas stream conditions, 2 ml of isopropanol-tetrahydrofuran (1:1) solution containing 20% of hydrogen chloride was added thereto and the whole mixture was stirred for 3 hours. The solvent was removed by evaporating under reduced pressure on a water bath at below 20° C. The residue obtained was further treated by evaporation under reduced pressure with adding 20 ml of benzene so as to remove hydrogen chloride. The residue obtained was dissolved in 20 ml of methanol, and a small amount of sodium hydrogen carbonate was added, and the mixture was stirred for 1 hour under oxygen gas stream conditions. The color of the reaction mixture turned yellow, and the solvent was removed by evaporation under reduced pressure. The residue obtained was treated by means of a separative silica gel thin layer chromatography ($F_{254}$, thickness: 2 mm, developer: 10% ethyl acetate-benzene) to obtain 320 mg of 2,5-dimethoxy-3(Z-6-undecenyl)-1,4-benzoquinone. Yellow oily substance.

PMR, $\delta$ ppm (CDCl$_3$) 0.89 (3H, t, J=7.0Hz), 1.35 (10H, brm), 2.01 (4H, brm), 2.43 (2H, brt, J=7.3Hz), 3.80 (3H, s), 4.05 (3H, s), 5.34 (2H, m), 5.72 (1H, s).

EXAMPLE 31

(1) By using procedures similar to those described in Example 30 (1), provided that 10 g (7.4 ml) of 1,9- dibromononane was used in place of 1,7-dibromobutane, there was prepared 7.2 g (yield=80.2%) of 1-bromo-9-[2,5-dimethoxy-3,6-bis(methoxymethoxy)-phenyl]nonane as in the form colorless oily substance.

PMR, $\delta_{ppm}^{CDCl_3}$: 1.2–1.7 (12H, brm), 1.82 (2H, brm), 2.70 (2H, brt, J=6.9Hz), 3.40 (2H, t, J=6.9Hz), 3.53 (3H, s), 3.59 (3H, s), 3.79 (6H, s), 5.02 (2H, s), 5.17 (2H, s), 6.64 (1H, s).

(2) By using procedures similar to those described in Example 30 (2), provided except that 2.31 g of 1-bromo-9-[2,5-dimethoxy-3,6-bis(methoxymethoxy)phenyl]nonane obtained in the above mentioned Example 31 (1) was used in place of 1-bromo-7-[2,5-dimethoxy-3,6-bis(methoxymethoxy)phenyl]heptane, there was prepared 2.3 g (yield=almost 100%) of 1-[2,5-dimethoxy-3,6-bis(methoxymethoxy)phenyl]pentadec-10-yne as in the form of colorless oily substance.

PMR, $\delta_{ppm}^{CDCl_3}$: 0.89 (3H, t, J=7.0Hz), 1.25–1.65 (18H, brm), 2.13 (4H, m), 2.65 (2H, brt, J=7.8Hz), 3.52 (3H, s), 3.58 (3H, s), 3.78 (6H, s), 5.01 (2H, s), 5.16 (2H, s), 6.63 (1H, s).

(3) 1 Gram of 1-[2,5-dimethoxy-3,6-bis(methoxymethoxy)phenyl]pentadec-10-yne prepared in the above-mentioned Example 31 (2) was catalyticall reduced under conditions similar to those described in Example 30 (3), and the reaction product obtained was purified by a reversed phase column chromatography. The catalytic reduction was traced by means of a high performance liquid chromatography. Thus, the reaction was determined by measuring the optical density (OD) at $UV_{254}$ under conditions of ODS column, 80%-acetonitrile-water, 2 ml/minute. After the reaction was completed, the catalyst was removed by filtration, and methanol was removed by evaporation under reduced pressure, the residue thus obtained was treated by means of a column chromatography ("Robar" column, LiChrosorb PR-8, Type C, manufactured by E. Merck A. G.), and developed and eluted with 80%-acetonitrile-water at flow rate of 5 ml/minute to obtain 0.65 g of 1-[2,5-dimethoxy-3,6-bis(methoxymethoxy)phenyl]-pentadec-10-ene (Z-isomer) as in the form of colorless oily substance.

PMR, $\delta_{ppm}^{CDCl_3}$: 0.89 (3H, t, J=7.0Hz), 1.2–1.65 (18H, brm), 2.01 (4H, brm), 2.66 (2H, brt, J=7.3Hz), 3.53 (3H, s), 3.58 (3H, s), 3.78 (6H, s), 5.02 (2H, s), 5.17 (2H, s), 5.34 (2H, m), 6.64 (1H, s).

(4) 500 Milligrams of 1-[2,5-dimethoxy-3,6-bis(methoxymethoxy)phenyl]-pentadec-10-ene obtained in the above-mentioned Example 31 (3) was treated under conditions similar to those described in Example 30 (4), there was prepared 306 mg (yield=76%) of 2,5-dimethoxy-3-(Z-10-pentadecenyl)-1,4-benzoquinone as in the form of yellow oily substance. The physical properties of this compound were identical to those shown by the compound prepared in Example 13 as mentioned above.

(5) By using procedures similar to those described in the above-mentioned Example 31 (4), except that 1-[2,5-dimethoxy-3,6-bis(methoxymethoxy)phenyl]-pentadec-10-yne was treated under conditions of the removal of protecting group and of the oxidation, there was obtained 2,5-dimethoxy-3-(10-pentadecynyl)-1,4-benzoquinone. Yellow oily substance.

PMR, δ ppm (CDCl$_3$) 0.90 (3H, t, J=7.0Hz), 1.5–1.2 (18H, m), 2.13 (4H, m), 2.42 (2H, t, J=7.3Hz), 3.80 (3H, s), 4.05 (3H, s), 5.72 (1H, s).

EXAMPLE 32

Under argon gas stream conditions, 100 ml of anhydrous tetrahydrofuran was cooled in a dry ice-acetone bath, to this solution was added dried acetylene gas by bubbling for 1 hour. Next, to this reaction mixture was added dropwise 9.6 ml of n-butyllithium (1.6M, n-hexane solution) and the whole mixture was stirred. 15 Minutes later, 10 ml of anhydrous tetrahydrofuran solution of 1-(5-bromopentyl)-2,5-dimethoxy-3,6-bis(methoxymethoxy)benzene prepared in Reference Example 1 was added dropwise to the reaction mixture, further 2 ml of hexamethylphosphoric triamide was added to the reaction mixture and stirred for 12 hours, then temperature of the reaction mixture was elevated to room temperature. Progress state of the reaction was traced by means of a high performance liquid column chromatography (ODS column, eluent: 60% acetonitrile-water, flow rate: 1.5 ml/minute). The solvent was removed by evaporation under a reduced pressure, to the residue obtained was added 400 ml of a mixed solvent of diethyl ether-benzene (1:1), and the organic layer was washed 4 times with water and a saturated sodium chloride aqueous solution in this order, then dried order anhydrous magnesium sulfate. The solvent was removed by evaporation under reduced pressure, and the residue was treated by a silica gel chromatography (diameter 3 cm×length 10 cm), then eluted with 20%-ethyl acetate-n-hexane to obtain 1.71 g of 1,4-dimethoxy-2,5-bis(methoxymethoxy)-3-(6-heptynyl)benzene. Colorless oily substance.

PMR, δ ppm (CDCl$_3$) 1.7–1.4 (6H, brm), 1.92 (1H, t, J=2.4Hz), 2.19 (2H, t, d, J$_1$=7.0Hz, 4Hz), 2.67 (2H, brt, J=7.6Hz), 3.52 (3H, s), 3.58 (3H, s), 3.78 (6H, s), 5.01 (2H, s), 5.16 (2H, s), 6.64 (1H, s).

By a method similar to that described in Example 32, there were prepared compounds of Examples 33 and 34 as follows.

EXAMPLE 33

1,4-Dimethoxy-2,5-bis(methoxymethoxy)-3-(8-nonynyl)benzene. Colorless oily substance.

PMR, δ ppm (CDCl$_3$) 1.7–1.25 (10H, brm), 1.93 (1H, t, J=2.6Hz), 2.17 (2H, t, d, J$_1$=6.7Hz, J$_2$=2.6Hz), 2.67 (2H, brt, J=7.1Hz), 3.52 (3H, s), 3.58 (3H, s), 3.78 (6H, s), 5.01 (2H, s), 5.17 (2H, s), 6.63 (1H, s).

EXAMPLE 34

1.25 (10H, brm), 1.93
1,4-Dimethoxy-2,5-bis(methoxymethoxy)-3-(10-undecynyl)benzene. Colorless oily substance.

PMR, δ ppm (CDCl$_3$) 1.7–1.25 (14H, brm), 1.93 (1H, t, J=7.6Hz), 2.17 (2H, t, d, J$_1$=6.7Hz, J$_2$=2.6Hz), 2.67 (2H, brt, J=7.6Hz), 3.52 (3H, s), 3.58 (3H, s), 3.78 (6H, s), 5.01 (2H, s), 5.17 (2H, s), 6.63 (1H, s).

EXAMPLE 35

1.61 Grams of 1,4-dimethoxy-2,5-bis(methoxymethoxy)-3-(6-heptynyl)benzene was dissolved in 40 ml of anhydrous tetrahydrofuran, and under argon gas stream condition the solution was cooled in a dry ice-acetone bath. To this cooled solution was added 3.42 ml of n-butyllithium (1.6M, hexane solution) was added dropwise thereto and stirred for 30 minutes. Then a solution prepared by dissolving 2.23 g of 1-(5-bronopentyl)-2,5-dimethoxy-3,6-bis(methoxymethoxy)benzene in 10 ml of anhydrous tetrahydrofuran was added dropwise to the reaction mixture. Further, 2 ml of hexamethylphosphoric triamide was added dropwise thereto, and temperature of the reaction mixture was elevated to room temperature in 12 hours. The solvent was removed by evaporation under reduced pressure, to the residue obtained was added 400 ml of a mixed solvent of diethyl ether-benzene (1:1), the organic layer was washed with water and a saturated sodium chloride aqueous solution in this order, then dried over anhydrous magnesium sulfate. Then the solvent was removed by evaporation under reduced pressure, the residue obtained was treated by means of a silica gel column chromatography, and eluted with a mixed solvent of from 20%–50% ethyl acetate-hexane those of which increasing the mixing ratios stepwise, then 2.09 g of 2,2'-(6-dodecynylene)bis[1,4-dimethoxy-3,6-bis(methoxymethoxy)benzene] was obtained. Colorless oily substance.

PMR, $\delta$ ppm (CDCl$_3$) 1.65–1.35 (12H, brm), 2.14 (4H, brm), 2.67 (4H, brt, J=7.0Hz), 3.52 (6H, s), 3.58 (6H, s), 3.78 (12H, s), 5.01 (4H, s), 5.17 4H, s), 6 63 2H, s).

By a method similar to that described in EXAMPLE 35, there were prepared compounds of Examples 36 and 37 respective as follows.

EXAMPLE 36

2,2'-(8-Hexadecynylene)bis[1,4-dimethoxy-3,6-bis(methoxymethoxy)benzene]. Colorless oily substance.

PMR, $\delta$ ppm (CDCl$_3$): 1.6–1.25 (20H, brm), 2.12 (4H, t, J=7.0 Hz), 2.66 (4H, brt, J=8.1 Hz), 3.53 (6H, s), 3.58 (6H, s), 3.78 (12H, s), 5.01 (4H, s), 5.17 (4H, s), 6.64 (2H, s).

EXAMPLE 37

2,2'-(10-Eicosynylene)bis[1,4-dimethoxy-3,6-bis(methoxymethoxy)benzene]. Colorless oily substance.

PMR, $\delta$ ppm (CDCl$_3$ 1.6-1.2 (28H, brm), 2.13 (4H, t, J=7.0Hz), 2.65 (4H, brt, J=8.2Hz), 3.53 (6H, s), 3.58 (6H, s), 3.78 (12H, s), 5.01 (4H, s), 5.17 (4H, s), 6.64 (2H, s).

EXAMPLE 38

By a method similar to that described above, except that 1 g of 1,4-dimethoxy-2,5-bis(methoxymethoxy)benzene, 40 ml of tetrahydrofuran, 3.57 ml of sec-butyllithium (1.3M, cyclohexane solution), 0.26 ml of 1,5-dibromopentane, 700 mg of sodium iodide, and 2 ml of hexamethylphosphoric triamide were used, among of which the amount of 1,5-dibromopentane was relatively smaller, there was prepared 335 mg of 2,2'-pentamethylene-bis[1,4-dimethoxy-3,6-bis(methoxymethoxy)benzene]. Colorless needles crystals.

Melting point: 67°–68° C.

PMR, $\delta$ppm (CDCl$_3$): 1.54 16H, m), 2.67 (4H, brt, J=7.3Hz), 3.52 (6H, s), 3.57 (6H, s), 3.77 (6H, s), 3.78 (6H, s), 5.01 (4H, s), 5.17 (4H, s), 6.64 (2H, s).

By a method similar to that described in Example 38, there were prepared compounds of Example 39 to Example 44 as follows.

EXAMPLE 39

2,2'-Hexamethylenebis[1,4-dimethoxy-3,6-bis(methoxymethoxy)benzene]. Colorless powdery substance.

Melting point: 59°–60° C.

PMR, $\delta$ ppm (CDCl$_3$): 1.43 (4H, brm), 1.50 (4H, brm), 2.65 (4H, t, J=7.0Hz), 3.53 (6H, s), 3.58 (6H, s), 3.77 (6H, s), 3.78 (6H, s), 5.01 (4H, s), 5.16 (4H, s), 6.63 (2H, s).

EXAMPLE 40

2,2'-Heptamethylenebis[1,4-dimethoxy-3,6-bis(methoxymethoxy)benzene]. Colorless oily substance.

PMR, $\delta$ ppm (CDCl$_3$ 1.39 6H, m), 1.55 (4H, m), 2.65 (4H, brt, J=7.8Hz), 3.53 3H, s), 3.58 (3H, s), 3.780 6H, s), 3.786 (6H, s), 5.01 (4H, s), 5.17 (4H, s), 6.63 2H, s).

EXAMPLE 41

2,2'-Octamethylenebis[1,4-dimethoxy-3,6-bis(methoxymethoxy)benzene]. Colorless oily substance.

PMR, $\delta$ ppm (CDCl$_3$) 1.6–1.3 (12H, m), 2.66 (4H, t, J=6.9Hz), 3.52 (6H, s), 3.58 (6H, s), 3.78 (12H, s), 5.02 (4H, s), 5.17 (4H, s), 6.63 (2H, s).

EXAMPLE 42

2,2'-Nonamethylenebis[1,4-dimethoxy-3,6-bis(methoxymethoxy)benzene]. Colorless oily substance.

PMR, $\delta$ ppm (CDCl$_3$) 1.4–1.25 (10H, m), 1.54 (4H, m), 2.65 (4H, brt, J=7.5Hz), 3.53 (6H, s), 3.58 (6H, s), 3.784 (6H, s), 3.787 (6H, s), 5.01 (4H, s), 5.17 (4H, s), 6.63 (2H, s).

EXAMPLE 43

2,2'-Decamethylenebis[1,4-dimethoxy-3,6-bis(methoxymethoxy)benzene]. Colorless oily substance.

PMR, $\delta$ ppm (CDCl$_3$) 1.6–1.2 (16H, m), 2.65 (4H, t, J=7.0Hz), 3.53 (6H, s), 3.58 (6H, s), 3.78 (12H, s), 5.02 (4H, s), 5.17 (4H, s), 6.64 (2H, s).

EXAMPLE 44

2,2'-Dodecamethylenebis-[1,4-dimethoxy-3,6-bis(methoxymethoxy)benzene]. Colorless oily substance.

PMR, $\delta$ ppm (CDCl$_3$) 1.4–1.2 (16H, m), 1.56 (4H, m), 2.66 (4H, brt, J=7.3Hz), 3.53 (6H, s), 3.58 (6H, s), 3.79 (12H, s), 5.01 (4H, s), 5.17 (4H, s), 6.63 (2H, s).

EXAMPLE 45

500 Milligrams of 2,2'-(6-dodecynylene)bis[1,4-dimethoxy-3,6-bis(methoxymethoxy)benzene]was dissolved in a mixed solvent of 5 ml of tetrahydrofuran with 5 ml of isopropanol. The gas phase in the reaction vessel was replaced with argon gas three times under reduced pressure deaeration. 1 Milliliter of tetrahydrofuran-isopropanol solution of hydrogen chloride (20%) was added to the reaction mixture and was stirred for 12 hours at room temperature. The reaction mixture was further heated to 40° C. for 1 hour to complete the reaction. The solvent was removed by evaporation under reduced pressure, to the residue thus obtained was added 10 ml of benzene and the solvent was removed by evaporation under a reduce pressure. There was prepared 2,2'-(6-docecynylene)bis(1,4-dihydroxy-3,6-dimethoxybenzene) as in the form of colorless powdery substance.

By a method similar to that described in Example 45, there were prepared compounds of Example 46 to Example as follows.

EXAMPLE 46

2,2'-(8-Hexadecynylene)bis(1,4-dihydroxy-3,6-dimethoxybenzene). Colorless oily substance.

PMR, $\delta$ ppm (CDCl$_3$): 1.7–1.2 (20H, brm), 2.12 (4H, t, J=7.0Hz), 2.63 (4H, brt, J=7.6Hz), 3.74 (6H, s), 3.82 (6H, s), 5.22 (2H, s), 5.29 (2H, s), 6.43 (2H, s).

EXAMPLE 47

2,2'-(10-Eicosynylene)bis(1,4-dihydroxy-3,6-dimethoxybenzene).

EXAMPLE 48

2,2'-Pentamethylenebis(1,4-dihydroxy-3,6dimethoxybenzene). Colorless powdery substance.
Melting point: 152°–152° C.
PMR, δ ppm (CDCl$_3$) 1.8–1.2 (6H, brm), 2.66 (4H, t, J=6.7Hz), 3.74 (6H, s), 3.82 (6H, s), 5.19 (2H, s), 5.25 (2H, s), 6.43 (2H, s).

EXAMPLE 49

2,2'-Hexamethylenebis(1,4-dihydroxy-3,6-dimethoxybenzene).

EXAMPLE 50

2,2'-Heptamethylenebis(1,4-dihydroxy-3,6-dimethoxybenzene).

EXAMPLE 51

2,2'-Octamethylenebis(1,4-dihydroxy-3,6-dimethoxybenzene).

EXAMPLE 52

2,2'-Nonamethylenebis(1,4-dihydroxy-3,6-dimethoxybenzene). Colorless powdery substance.
Melting point: 100°–102° C.
PMR, δ ppm (CDCl$_3$) 1.8–1.2 (14H, brm), 2.63 (4H, t, J=7.6Hz), 3.74 (6H, s), 3.81 (6H, s), 5.35 (4H, s), 6.43 (2H, s).

EXAMPLE 53

2,2'-Decamethylenebis(1,4-dihydroxy-3,6-dimethoxybenzene).

EXAMPLE 54

2,2'-Dodecamethylene(1,4-dihydroxy-3,6-dimethoxybenzene).

EXAMPLE 55

9.8 Grams of 2,2'-pentamethylenebis[1,4-imethoxy-3,6-(methoxymethoxy)benzene] was dissolved in 400 ml of anhydrous tetrahydrofuran under argon gas stream conditions, to this solution was added 100 ml of hexamethylphosphoric triamide, and the whole mixture was cooled in a dry ice-acetone bath. 29.35 Milliliters of sec-butyllithium (1.4M, cyclohexane solution) was added dropwise to the reaction mixture and stirred for 1 hour. Next, thereto 4.3 ml of methyl iodide was added dropwise and the whole reaction mixture was cooled in a dry ice-acetone bath for 12 hours with stirring. The solvent was removed from the reaction mixture by evaporation under reduced pressure, to the residue obtained was added 2 liters of a mixed solvent of diethyl etherbenzene (1:1) and the organic layer was washed with water and with a saturated sodium chloride aqueous solution in this order, then dried over anhydrous magnesium sulfate. The dried organic layer was concentrated to obtain 11 g of 2,2'-pentamethylenebis[1,4-dimethoxy-3,6-bis(methoxymethoxy)-5-methylbenzene]. Colorless needles crystals.
Melting point: 83°–84° C.
PMR, δ ppm (CDCl$_3$) 1.7–1.4 (6H, brm), 2.19 (6H, s), 2.61 (4H, brt, J=7.0Hz), 3.55 (12H, s), 3.70 (6H, s), 3.73 (6H, s), 5.01 (8H, s).

EXAMPLE 56

140 Milligrams of 2,2'-pentamethylene-bis[1,4-dimethoxy-3,6-bis(methoxymethoxy)benzene] was dissolved in 5 ml of anhydrous tetrahydrofuran under argon gas stream conditions, then 0.5 ml of hexamethylphosphoric triamide was added to this solution and the mixture was cooled in a dry ice-acetone bath. Next, 0.23 ml of sec-butyllithium (1.4M, cyclohexane solution) was added dropwise to the reaction mixture and stirred for 1 hour. Then, 0.06 ml of methyl iodide was added dropwise thereto under cooling in a dry ice-acetone bath for 12 hours with stirring. The solvent was removed by evaporation under reduced pressure, to the residue obtained was added 100 ml of a mixed solvent of diethyl etherbenzene (1:1), and the organic layer was washed with water then with a saturated sodium chloride aqueous solution, and dried over anhydrous magnesium sulfate. The dried solution was concentrated under reduced pressure to obtain 100 mg of 1,4-dimethoxy-2,5-bis(methoxymethoxy)-3-methyl-6-{5-[2,5-dimethoxy-3,6-bis(methoxymethoxy)phenyl]pentyl}benzene. Colorless needles crystals.
Melting point: 76°–77° C.
PMR, δ ppm (CDCl$_3$) 1.8–1.3 (6H, brm), 2.18 (3H, s), 2.63 (4H, brm), 3.51 (3H, s), 3.56 (9H, s), 3.70 (3H, s), 3.74 (3H, s), 3.76 (6H, s), 5.02 (6H, s), 5.13 (2H, s), 6.70 (1H, s).

EXAMPLE 57

By a method similar to that described in Example 45, there was prepared the following compound.
2,2'-Pentamethylenebis[1,4-dimethoxy-3,6-dimethoxy-5-methylbenzene]. Colorless powdery substance.
PMR, δ ppm (CDCl$_3$-DMSO-D$_6$) 1.7–1.3 (6H, brm), 2.10 (6H, s), 2.5 (4H, brm), 3.65 (6H, s), 3.69 (6H, s), 7.20 (2H, s), 7.35 (2H, s).

EXAMPLE 58

1.1 Grams (1.8 mmoles) of 2,2'-(1,5-pentamethylene)-bis[1,4-dimethoxy-3,6-bis(methoxymethoxy)benzene] was dissolved in a mixed solvent of 20 ml of tetrahydrofuran with 4 ml of hexamethylphosphoric triamide, and the solution was cooled in a dry ice-acetone bath to −78° C. Then to this cooled solution was added sec-butyllithium (1.4 mmoles/ml) and stirred for 1 hour. Next, 1 milliliter of tetrahydrofuran solution of ethylene oxide (2.1 mmoles/ml) was added further a small amount of boron trifluoride etherate (BF$_3$—OEt$_2$) was added thereto. The reaction mixture was stirred for 4 hours at −78° C., and concentrated under reduced pressure. To the residue obtained was added 300 ml of a mixed solvent benzene-diethyl ether (1:1), and the organic layer was washed with water and then with a saturated sodium chloride aqueous solution, and dried over anhydrous magnesium sulfate, then filtered. The filtrate obtained was purified by means of a silica gel column chromatography (adsorbent: 20 g of silica gel, eluent: 40% ethyl acetatebenzene) to obtain 0.6 g of 1-(2-hydroxyethyl)-2,5-dimethoxy-3,6-bis(methoxymethoxy)-4-{5-[3,6-dimethoxy-2,5-bis(methoxymethoxy)-phenyl]pentyl}benzene. Amorphous powdery substance.
PMR, δ ppm (CDCl$_3$) 1.4–1.6 (6H, brm), 2.60 (4H, t, J=6.0Hz), 2.95 (2H, t, J=6.0Hz), 3.52 (3H, s), 3.53 (6H, s), 3.55 (3H, s), 3.76 (3H, s), 3.77 (6H, s), 3.80 (3H, s), 5.01 (4H, s), 5.03 (4H, s), 6.60 (1H, s).

EXAMPLE 59

By a method similar to that described in Example 58, except that 2 times the amount of sec-butyllithium and 5 times the amount of ethylene oxide were used, there was obtained 0.9 g of 4,4'-pentamethylenebis[1-(2-hydroxyethyl)2,5-dimethoxy-3,6-bis(methoxymethoxy)benzene]. Colorless needles crystals.

Melting point: 68°–70° C. PMR, $\delta$ ppm (CDCl$_3$) 1.4–1.6 (6H, brm), 2.50 (4H, 6, J=6.0Hz), 2.96 (4H, t, J=6.0Hz), 3.53 (6H, s), 3.54 (6H, s), 3.75 (6H, s), 3.76 (6H, s), 3.79 (4H, t, J=6.0Hz), 5.01 (4H, s), 5.04 (4H, s).

EXAMPLE 60

200 Milligrams of 2,2'-pentamethylenebis(1,4-dihydroxy-3,6-dimethoxybenzene) was dissolved in 20 ml of methanol, the solution was heated at 60° C. and oxygen gas was blown into the solution. A small amount of sodium hydrogen carbonate was added thereto and reacted for about 1 hour. The solvent was removed by evaporation under reduced pressure, and the residue obtained was treated by means of a silica gel thin layer chromatography (thickness: 2 mm, developer: 20% ethyl acetate-benzene) to obtain 135 mg of crude product of 2,2'-pentamethylenebis(3,6-dimethoxy-1,4-benzoquinone) as in the form of yellow oily substance. Recrystallized from ethanol-water to obtain yellow needles crystals thereof.

Melting point: 113°–115° C.

PMR, $\delta$ ppm (CDCl$_3$) 1.35 (6H, brm), 2.42 (4H, brt, J=7.3Hz), 3.80 (6H, s), 4.04 (6H, s), 5.72 (2H, s).

By a method similar to that described in Example 60, there were prepared compounds of Example 61 to Example 66 as follows.

EXAMPLE 61

2,2'-Hexamethylenebis(3,6-dimethoxy-1,4benzoquinone). Yellow needles crystals.

Melting point: 120°–122° C.

PMR, $\delta$ ppm (CDCl$_3$) 1.5–1.2 (8H, brm), 2.42 (4H, t, J=6.8Hz), 3.80 (6H, s), 4.05 (6H, s), 5.72 (2H, s).

EXAMPLE 62

2,2'-Heptamethylenebis(3,6-dimethoxy-1,4-benzoquinone). Yellow needles crystals.

Melting point: 77°–78° C.

PMR, $\delta$ ppm (CDCl$_3$) 1.5–1.2 (10H, brm), 2.41 (4H, t, J=7.3Hz), 3.80 (6H, s), 4.04 (6H, s), 5.72 (2H, s).

EXAMPLE 63

2,2'-Octamethylenebis(3,6-dimethoxy-1,4-benzoquinone). Yellow needles crystals.

Melting point: 108°–110° C.

PMR, $\delta$ ppm (CDCl$_3$) 1.5–1.2 (12H, brm), 2.42 (4H, t, J=6.8Hz), 3.80 (6H, s), 4.04 (6H, s), 5.72 (2H, s).

EXAMPLE 64

2,2'-Nonamethylenebis(3,6-dimethoxy-1,4-benzoquinone). Yellow prism-like crystals.

Melting point: 72°–74° C.

PMR, $\delta$ ppm (CDCl$_3$) 1.5–1.2 (14H, brm), 2.42 (4H, t, J=7.6Hz), 3.80 (6H, s), 4.04 (6H, s), 5.72 (2H, s).

EXAMPLE 65

2,2'-Decamethylenebis(3,6-dimethoxy-1,4-benzoquinone). Yellow oily substance.

PMR, $\delta$ ppm (CDCl$_3$) 1.6–1.2 (16H, m), 2.42 (4H, t, J=7.9Hz), 3.80 (6H, s), 4.05 (6H, s), 5.72 (2H, s).

EXAMPLE 66

2,2'-Dodecamethylenebis(3,6-dimethoxy-1,4-benzoquinone). Yellow oily substance.

PMR, $\delta$ ppm (CDCl$_3$) 1.5–1.2 (20H, m), 2.42 (4H, t, J=7.6Hz), 3.80 (6H, s), 4.04 (6H, s), 5.72 (2H, s).

EXAMPLE 67

2,2'-(6-Dodecynylene)bis(3,6-dimethoxy-1,4-benzoquinone). Yellow oily substance.

PMR, $\delta$ ppm (CDCl$_3$) 1.65–1.2 (12H, brm), 2.12 (4H, brt, J=6.7 Hz), 2.43 (4H, brt, J=7.0Hz), 3.79 (6H, s), 4.05 (6H, s), 5.72 (2H, s).

EXAMPLE 68

2,2'-(8-Hexadecynylene)bis(3,6-dimethoxy-1,4-benzoquinone). Yellow oily substance.

PMR, $\delta$ ppm (CDCl$_3$) 1.7–1.2 (20H, brm), 2.12 (4H, t, J=7.3Hz), 2.42 (4H, t, J=7.3Hz), 3.80 (6H, s), 4.05 (6H, s), 5.72 (2H, s).

EXAMPLE 69

2,2'-(10-Eicosynylene)bis(3,6-dimethoxy-1,4-benzoquinone). Yellow oily substance.

PMR, $\delta$ ppm (CDCl$_3$) 1.7–1.2 (28H, brm), 2.12 (4H, t, J=7.3Hz), 2.42 (4H, J=7.3Hz), 3.80 (6H, s), 4.04 (6H, s), 5.72 (2H, s).

EXAMPLE 70

7 Grams of 2,2'-pentamethylenebis(1,4-dihydroxy-3,6-dimethoxy-5-methylbenzene) was dissolved in 200 ml of methanol, and a small amount of sodium hydrogen carbonate was added to the solution and the mixture was heated at 60° C. The reaction was carried out by blowing oxygen gas for 2 hours, then the solvent was removed by evaporation under reduced pressure. The residue obtained was treated by means of a silica gel column chromatography (eluent: 10% ethyl acetate-n-hexane) to obtain yellow oily substance. Then, this substance was recrystallized from ethanol-water to obtain 2,2'-pentamethylenebis(3,6-dimethoxy-5-methyl-1,4-benzoquinone). Yellow needles crystals.

Melting point: 84°–86° C.

PMR, $\delta$ ppm (CDCl$_3$): 1.40 (6H, brm), 1.91 (6H, s), 2.40 (4H, brt, J=7.3 Hz), 3.99 (12H, s).

EXAMPLE 71

426 Milligrams of 1,4-dimethoxy-2,5-bis(methoxymethoxy)-3-methyl-6-{5-[2,5-dimethoxy-3,6-bis(methoxymethoxy)phenyl]pentyl}benzene was dissolved in 5 ml of tetrahydrofuran and 5 ml of isopropanol, under nitrogen gas stream conditions, 1 ml of tetrahydrofuran-isopropanol (1:1) solution of 20% hydrogen chloride was added thereto, and the mixture was stirred at room temperature for 12 hours. The solvent was removed by evaporation under reduced pressure to obtain colorless powdery substance. This substance was dissolved, without being purified, in 20 ml of methanol, and a small amount of sodium hydrogen carbonate was added, then the mixture was heated at 60° C., and was stirred for 2 hours under oxygen gas stream condition. The solvent was removed by evaporation under reduced pressure, and the residue obtained was developed on a preparative thin layer chromatography (eluent: 40% ethyl acetate-n-hexane) to obtain 262 mg of 2,5-dimethoxy3-methyl-6-[5-(2,5-dimethoxy-1,4-benzoquinon-3-yl)pentyl]1,4-benzoquinone. Yellow powdery substance.

Melting point: 48°–49° C.

PMR, δ ppm (CDCl₃) 1.45–1.25 (6H, brm), 1.91 (3H, s), 4.39 (2H, t, J=7.8Hz), 2.43 (2H, t, J=7.8Hz), 3.79 (3H, s), 3.98 (6H, s), 4.05 (3H, s), 5.72 (1H, s).

EXAMPLE 72

402 Milligrams of 4,4′-pentamethylenebis[1-(2-hydroxyethyl)-2,5-dimethoxy-3,6-bis(methoxymethoxy)benzene] was dissolved in a mixed solvent of 4 ml of tetrahydrofuran with 4 ml of isopropanol, under ice-cooling conditions, 0.8 ml of tetrahydrofuran-isopropanol (1:1) solution containing 20% of hydrogen chloride was added thereto. The reaction mixture was heated at 50° C. on a water bath for 5 hours with stirring. The reaction mixture was concentrated, and to the residue obtained was added 10 ml of methanol and a small amount of sodium hydrogen carbonate, then whole mixture was heated at 50 to 60° C., on a water bath and oxygen gas was blown into the reaction mixture for 5 hours. After the reaction was completed, the reaction mixture was filtered, and concentrated, the residue obtained was treated by means of a preparative thin layer chromatography (silica gel plate: 20×20 cm, thickness 2 mm, 2 plates were used, developing solvent: ethyl acetate:benzene=1:1), then recrystallized from petroleum ether to obtain 305 mg of 5,5′-pentamethylenebis[2-(2-hydroxyethyl)-3,6-dimethoxy-1,4-benzoquinone] was obtained. Yellow needles crystals.

Melting point: 97°–99° C.

PMR, δ ppm (CDCl₃) 1.2–1.5 (6H, m), 2.35 (4H, brt, J=6.5Hz), 2.68 (4H, t, J=7.5Hz), 3.67 (4H, t, J=7.5Hz), 3.96 (6H, s), 4.00 (6H, s).

EXAMPLE 73

280 Milligrams (1.08 mmoles) of 1,4-dimethoxy-2,5-bis(methoxymethoxy)benzene was dissolved in a mixed solvent of 5 ml of tetrahydrofuran with 1 ml of hexamethylphosphoric triamide, then this solution was cooled to −78° C. in a dry ice-acetone bath. To this cooled solution was added 1.08 ml (1.21 mmoles) of secbutyllithium (1.21 M, cyclohexane solution) and the mixture was stirred for 30 minutes, then 2 ml of tetrahydrofuran solution containing 440 mg (1.0 mmole) of 1-(4-iodobutyl)-2,5-dimethoxy-3,6-bis(methoxymethoxy)benzene was added thereto and stirred for 12 hours. The reaction mixture was concentrated, to the residue obtained was added 60 ml of diethyl ether, and washed twice with water, then washed twice with a saturated sodium chloride aqueous solution, then dried over anhydrous magnesium sulfate. The dried diethyl ether solution was concentrated under reduced pressure, the residue obtained was purified by means of a silica gel column chromatography (diameter 2 cm×length 20 cm, eluent: 20% ethyl acetate-benzene) to obtain 467 mg of 2,2′-tetramethylenebis[1,4-dimethoxy-3,6-bis(methoxymethoxy)benzene]. Colorless oily substance.

PMR, δ ppm (CDCl₃) 1.6–1.7 (4H, m), 2.70 (4H, br, t, J=7.5Hz), 3.53 (6H, s), 3.57 (6H, s), 3.80 (6H, s), 3.79 (6H, s), 5.00 (4H, s), 5.17 (4H, s), 6.63 (2H, s).

EXAMPLE 74

374 Milligrams of 1-(2-hydroxyethyl)-2,5-dimethoxy-3,6-bis(methoxymethoxy)benzene was dissolved in 3 ml of dimethylformamide, under ice-cooling conditions, 80 mg of sodium hydride (60% dispersion) was added thereto, then 2 ml of tetrahydrofuran solution containing 527 mg of 1-(3-iodopropyl)-2,5-dimethoxy-3,6-bis(methoxymethoxy)benzene was added. The reaction mixture was heated at 50° C. in an oil bath. 6 Hours later, ice water and 100 ml of diethyl ether were added to the reaction mixture. The ether layer was washed twice with 50 ml of water, then washed twice with 50 ml of a saturated sodium chloride aqueous solution, then dried over anhydrous magnesium sulfate. This solution was concentrated under reduced pressure, and the residue obtained was purified by means of a silica gel column chromatography (diameter 3 cm×length 15 cm, eluent: 40% ethyl acetate-n-hexane mixed solvent, adsorbent: "Wakogel C-200") to obtain 484 mg of 2-[2,5-dimethoxy-3,6-bis(methoxymethoxy)phenyl]ethyl 3-[2,5-dimethoxy-3,6-bis(methoxymethoxy)phenyl]propyl ether.

PMR, δ ppm (CDCl₃): 1.85 (2H, m), 2.73 (2H, t, J=6.1Hz), 3.00 (2H, t, J=6.2Hz), 3.53 (2H, t, J=6.1Hz), 3.54 (6H, br, s), 3.58 (6H, br, s), 3.59 (2H, t, J=6.2Hz), 3.79 (9H, br, s), 3.80 (3H, s), 5.03 (4H, br, d, J=5.1Hz), 5.17 (4H, br, s), 6.65 (1H, s), 6.67 (1H, s).

EXAMPLE 75

696 Milligrams of 1-hydroxymethyl-2,5-dimethoxy-3,6-bis(methoxymethoxy)benzene was dissolved in 10 ml of dimethylformamide, then under ice-cooling conditions, 114 mg of sodium hydride (60% dispersion) was added thereto, next 3 ml of dimethylformamide solution containing 741 mg of 1-chloromethyl-2,5-dimethoxy-3,6-bis(methoxymethoxy)benzene was added to the mixture and the whole mixture was heated to 50°–60° C. for 12 hours with stirring. Ice water was added to the reaction mixture and extracted with 100 ml of ethyl acetate. The ethyl acetate layer was washed twice with 50 ml of water, then washed twice with 50 ml of a saturated sodium chloride aqueous solution, and dried over anhydrous sodium sulfate. This dried extract was concentrated, and the residue obtained was purified by means of a silica gel column chromatography (diameter 2 cm×length 15 cm, eluent: 20% ethyl acetate(diameter benzene mixed solvent, adsorbent: "Wakogel C-200") to obtain 1.2 g of bis:[2,5-dimethoxy-3,6-bis(methoxymethoxy)phenyl]methyl}ether. Colorless powder.

PMR, δ ppm (CDCl₃) 3.47 (6H, s), 3.53 (6H, s), 3.76 (6H, s), 3.78 (6H, s), 4.65 (4H, s), 5.00 (4H, s), 5.14 (4H, s), 6.71 (2H, s).

EXAMPLE 76

140 Milligrams of 1,4-dimethoxy-2,5-bis(methoxymethoxy)benzene was dissolved in 4 ml of anhydrous tetrahydrofuran, to this solution was added 1 ml of hexamethylphosphoric triamide. This mixture was cooled to −78° C., and 0.54 ml of sec-butyllithium (1.2 M solution) was added dropwise to the mixture and stirred for 30 minutes. Next, a solution prepared by dissolving 350 mg of 1-(3-iodopropyl)-2,5-dimethoxy-3,6-bis(methoxymethoxy)benzene in 1 ml of anhydrous tetrahydrofuran was added to the reaction mixture and stirred for 2 hours to complete the reaction. The reaction mixture was concentrated under reduced pressure, the residue thus obtained was treated by means of a silica gel preparative thin layer chromatography (thickness: 2 mm, adsorbent: silica gel), and was developed twice with 30% ethyl acetate-n-hexane. There was obtained 169 mg of the desired product of 2,2′-trimethylenebis[1,4-dimethoxy-3,6-bis(methoxymethoxy)benzene]. Colorless oily substance.

PMR, δ ppm (CDCl₃) 1.83 (2H, m), 2.78 (4H, br, t, J=7Hz), 3.51 (6H, s), 3.56 (6H, s), 3.77 (12H, s), 4.99 (4H, s), 5.15 (4H, s), 6.62 (2H, s).

EXAMPLE 77

300 Milligrams (1.25 mmoles) of sodium sulfide (Na$_2$S·9H$_2$O) was dissolved in 10 ml of ethanol, to this solution was added a solution prepared by dissolving 573.7 mg of 1-(3-iodopropyl)-2,5-dimethoxy-3,6-bis(methoxymethoxy)benzene in 6 ml of ethanol under ice-cooling conditions. Then, the reaction mixture was stirred at a room temperature for 20 minutes, further stirred for 2 hours under refluxing conditions. The reaction mixture was cooled and concentrated under reduce pressure, the residue obtained was treated by means of a preparative thin layer chromatography (adsorbent: Silica gel 60, thickness: 1 mm, manufactured by E. Merck A. G., developer: ethyl acetate:n-hexane=3:7) to obtain 290.0 mg of bis{3-[2,5-dimethoxy-3,6-bis(methoxymethoxy)phenyl]propyl}disulfide. Colorless oily substance.

PMR, δ ppm (CDCl$_3$) 1.8–2.1 (4H, m), 2.7–1.85 (8H, m), 3.53 (6H, s), 3.59 (6H, s), 3.80 (12H, s), 5.03 (4H, s), 5.18 (4H, s), 6.66 (2H, s).

EXAMPLE 78

60.97 Milligrams (0.25 mmole) of sodium sulfide (Na2S 9H$_2$O) was dissolved in 2 ml of ethanol, under ice-cooling conditions, a solution prepared by dissolving 230.5 mg (0.5 mmole) of 1-(5-iodopentyl)-2,5-dimethoxy-3,6-bis(methoxymethoxy)benzene in 2 ml of ethanol was added dropwise, and the reaction mixture was stirred for 20 minutes under refluxing conditions. After cooling the reaction mixture, it was concentrated under a reduce pressure, and the residue obtained was treated by means of a preparative thin layer chromatography (adsorbent: Silica gel 60, thickness 1 mm, manufactured by E. Merck A. G., developer: ethyl acetate:n-hexane=3:7) to obtain 56.9 mg of bis{5-[2,5-dimethoxy-3,6-bis(methoxymethoxy)phenyl]pentyl}sulfide. Colorless oily substance.

PMR, δ ppm (CDCl$_3$) 1.33–1.73 (12H, m), 2.37–2.80 (8H, m), 3.48 (6H, s), 3.53 (6H, s), 3.76 (12H, s), 4.97 (4H, s), 5.13 (4H, s), 6.61 (2H, s).

EXAMPLE 79

1.4 Grams of 2,5-dihydroxy-1,4-benzoquinone was dissolved in 40 ml of tetrahydrofuran, to this solution was added 10 ml of acetic acid and 0.2 ml of 37%-formalin aqueous solution and the mixture was stirred over night at room temperature. The reaction mixture was concentrated to dryness, and the residue obtained was dissolved in 50 ml of tetrahydrofuran, and was methylated by adding an excess amount of diazomethane-ether solution at 0° C., being stirred for 0.5 hour. Next, the reaction mixture was treated by means of a silica gel column chromatography [eluent: ethyl acetatedichloromethane (5:95 mixture by volume/volume)]to obtain a crude product. Then this crude product was recrystallized from ethanol to obtain 220 mg of 2,2'-methylenebis(3,6-dimethoxy-1,4-benzoquinone). Yellow needles crystals.

Melting point: 198°–199° C.
PMR, δ ppm (CDCl$_3$) 3.62 (2H, s), 3.80 (6H, s), 4.07 (6H, s), 5.73 (2H, s).

EXAMPLE 80

Under ice-cooling conditions, 302 mg of 1,2-bis[2,5-dimethoxy-3,6-bis(methoxymethoxy)phenyl]ethanol was dissolved in 5 ml of trifluoroacetic acid, then 0.4 ml of triethylsilane was added to the solution. This mixture was stirred under ice-cooling conditions for 2 hours. After concentrated the reaction mixture, benzene was added and the mixture was further treated under a reduced pressure. The residue thus obtained was dissolved in 5 ml of methanol, and a catalytic amount of sodium hydrogen carbonate was added thereto, and oxygen gas was blown into the reaction mixture. 2 Hours later, the reaction mixture was filtered, and the filtrate was concentrated under a reduced pressure. The residue obtained was treated by means of a thin layer chromatography (adsorbent: silica gel, manufactured by E. Merck A. G., size: 20 cm×20 cm, thickness: 2 mm, 2 plates were used, developping solvent: 30% ethyl acetate-n-hexane) to obtain 132 mg of 2,2'-ethylenebis(3,6-dimethoxy1,4-benzoquinone). Yellow oily substance.

PMR, δ ppm (CDCl$_3$) 2.60 (4H, s), 3.58 (6H, s), 3.87 (6H, s), 5.62 (2H, s).

EXAMPLE 81

355 Milligrams of 2,2'-tetramethylenebis[1,4-dimethoxy-3,6-bis(methoxymethoxy)benzene] was dissolved in a mixed solvent of 8 ml of isopropanol with 4 ml of tetrahydrofuran, to this solution was added 1.2 ml of solution prepared by dissolving 10% (by weight/weight) of hydrogen chloride in a mixed solvent of tetrahydrofuran-isopropanol (1:1), and the mixture was stirred at room temperature for 12 hours. The reaction mixture was concentrated under reduced pressure, to the residue obtained was added benzene, and further concentrated under reduced pressure. The residue thus obtained was dissolved in 5 ml of methanol, and a catalytic amount of sodium hydrogen carbonate was added thereto and oxygen gas was blown thereinto. 2 Hours later, the reaction mixture was filtered, and the filtrate was concentrated under reduced pressure, and the residue obtained was purified by means of a silica gel chromatography (diameter 2 cm×length 5 cm, eluent: 30%-ethyl acetate-n-hexane mixed solvent, adsorbent: "Wakogel C-200") to obtain 120 mg of 2,2'-tetramethylenebis(3,6-dimethoxy-1,4-benzoquinone). Yellow needles crystals.

Melting point: 185°–186° C.
PMR, δ ppm (CDCl$_3$) 1.42 (4H, m), 2.43 (4H, t, J=7.6Hz), 3.80 (6H, s), 4.03 (6H, s), 5.72 (2H, s).

EXAMPLE 82

484 Milligrams of 2-[2,5-dimethoxy-3,6-bis(methoxymethoxy)phenyl]ethyl 3-[2,5-dimethoxy-3,6bis(methoxymethoxy)phenyl]propyl ether was dissolved in a mixed solvent of 5 ml of tetrahydrofuran with 5 ml of isopropanol, to this solution was added 1.0 ml of solution prepared by dissolving 10% (by weight) of hydrogen chloride in a mixture of tetrahydrofuran with isopropanol (1:1), and the whole mixture was stirred at room temperature for 14 hours. The reaction mixture was concentrated, and benzene was added then further treated under reduced pressure to concentrated. The residue obtained was dissolved in 10 ml of methanol, and a catalytical amount of sodium hydrogen carbonate was added thereto and oxygen gas was blown thereinto. The precipitated crystals were dissolved by adding dichloromethane and filtered. The filtrate was concentrated and the residue obtained was purified by means of a silica gel column chromatography, (diameter 2 cm×length 5 cm, developping solvent: 10% ethyl acetate-dichloromethane solution, adsorbent: "Wakogel C-200", to obtain a crude product, then recrystallized from ethanol to obtain 243 mg of 2-(3,6-dimethoxy1,4- benzoquinon-2-yl)ethyl 3-(3,6-dimethoxy-1,4-benzoquinon2-yl)propyl ether. Yellow needles crystals.

Melting point: 129°–130° C.

PMR, δ ppm (CDCl$_3$) 1.8–1.5 (2H, m), 2.48 (2H, t, J=7.6Hz), 2.73 (2H, t, J=7.2Hz), 3.5–3.3 (4H, m), 3.80 (6H, br, s), 4.06 (3H, s), 4.07 (3H, s), 5.72 (1H, s), 5.73 (1H, s).

EXAMPLE 83

402 Milligrams of bis{[1,4-dimethoxy-3,6-bis(methoxymethoxy)phenyl]methyl}ether was dissolved in a mixed solvent of 4 ml of tetrahydrofuran with 4 ml of isopropanol, to this solution was added 0.8 ml of solution prepared by dissolving 10% by weight) of hydrogen chloride in a mixed solvent of tetrahydrofuran-isopropanol (1:1), then the whole mixture was heated at 40 to 50° C. for 4 hours. The reaction mixture was concentrated, then to the residue obtained was added benzene and further concentrated. The residue thus obtained was dissolved in acetonitrile and a catalytical amount of cuprous chloride, then oxygen gas was blown into the solution. 1 Hour later, the solution was filtered and the filtrate was concentrated under a reduced pressure, then the residue obtained was treated by means of a silica gel column chromatography (diameter 1.5 cm×length 10 cm, eluent: 20% ethyl acetate-benzene, adsorbent: "Wakogel C-200"), to obtain 82 mg of bis [(3,6-dimethoxy-1,4-benzoquinon-2-yl)methyl]ether. Yellow oily substance.

PMR, δ ppm (CDCl$_3$) 3.48 (4H, s), 3.51 (6H, s), 3.96 (6H, s), 5.80 (2H, s).

EXAMPLE 84

169 Milligrams of 2,2'-trimethylenebis[1,4-dimethoxy-3,6-bis(methoxymethoxy)benzene] was dissolved in 2 ml of tetrahydrofuran and 2 ml of isopropanol, then to this solution was added 0.4 ml of a tetrahydrofuranisopropanol (1:1) solution containing 20% (by weight) of hydrogen chloride, then the mixture was stirred at room temperature for 1 day under argon gas stream condition. The solvent was removed by evaporation under reduced pressure, then the residue obtained was dissolved in 20 ml of methanol, and a small amount of sodium hydrogen carbonate was added to this solution, and stirred at room temperature for 30 minutes with blowing oxygen gas thereinto. The solvent was removed by evaporation, the resulting residue was treated by means on a preparative thin layer chromatography (thickness 1 mm, adsorbent: silica gel), and developped with a mixed solvent of ethyl acetate-n-hexane (1:1) to obtain 50 mg of crude product. The crude product was recrystallized from ethanol to obtain 20.4 mg of 2,2'-trimethylenebis(3,6-dimethoxy1,4-benzoquinone). Yellow fine needles crystals.

Melting point: 157°–159° C.

PMR, δ ppm (CDCl$_3$) 1.54 (2H, m), 2.47 (4H, br, t, J=7.6Hz), 3.80 (6H, s), 4.06 (6H, s), 5.73 (2H, s).

EXAMPLE 85

259.7 Milligrams of bis{3-[2,5-dimethoxy-3,6-bis(methoxymethoxy)phenyl]propyl} disulfide was dissolved in a mixed solvent of 4 ml of tetrahydrofuran with 4 ml of isopropanol. The gas phase in the reaction vessel was replaced with argon gas three times under reduced pressure deaeration. 1 Milliliter of tetrahydrofuranisopropanol solution containing 20% (by weight) of hydrogen chloride was added to the reaction mixture, and the reaction mixture was heated at 70° C. with stirring, the reaction was completed in about 1 hour. The solvent was removed by evaporation under reduced pressure, then 5 ml of benzene was added to the residue, this mixture was further treated under reduced pressure to obtain light brawn oily substance. The crude substance was dissolved in 10 ml of methanol without being purified, and to this solution a small amount of sodium hydrogen carbonate was added, and oxygen gas was bubbled thereinto at room temperature for about 2 hours. The solvent was removed by evaporation under reduced pressure, the residue obtained was treated by means of a silica gel preparative thin layer chromatography (thickness: 1 mm, developing solvent: 50% ethyl acetate-benzene) to obtain 45.0 mg of bis[3-(3,6-dimethoxy-1,4-benzoquinon-2-yl)propyl]disulfide. Yellow oily substance.

PMR, δ ppm (CDCl$_3$): 1.81 (6H, m), 2.55 (6H, t, J=7.6Hz), 2.69 (6H, t, J=7.2Hz), 3.81 (6H, s), 4.09 (6H, s), 5.74 (2H, s).

High resolution mass spectrometry (for C$_{22}$H$_{26}$O$_8$S$_2$): Calculated (m/z): 482.1069; Found (m/z): 482.1096.

EXAMPLE 86

118.0 Milligrams (0.17 mmole) of bis{5-[2,5-dimethoxy-3,6-bis(methoxymethoxy)phenyl]pentyl} sulfide was dissolved in a mixed solvent of 1 ml of tetrahydrofuran—1 ml of isopropanol. The gas phase in the reaction vessel was replaced three times with argon gas under reduced pressure deaeration. 0.2 Milliliters of tetrahydrofuran-isopropanol solution containing 20% (by weight) of hydrogen chloride was added to the reaction vessel, and the reaction mixture was stirred at room temperature for 1 hour, then the temperature was elevated to 70° C., and the reaction was completed in an hour. The solvent was removed by evaporation under reduced pressure, then 2 ml of benzene was added to the residue, this mixture was further treated under reduced pressure to obtain light brawn oily product. This product was dissolved in 5 ml of methanol without purified, then this solution was heated to 40° C., a small amount of sodium hydrogen carbonate was added thereto, and oxygen gas was bubbled therein, and the reaction was completed in about 1 hour. The solvent was removed under reduced pressure, and the residue obtained was treated by means of a silica gel preparative thin layer chromatography (thickness: 1 mm, developing solvent: 50% ethyl acetate-n-hexane) to obtain 60.5 mg of bis[5-(3,6-dimethoxy-1,4-benzoquinon-2-yl)pentyl] sulfide. Yellow oily substance.

PMR, δ ppm (CDCl$_3$) 1.3–1.9 (12H, m), 2.3–2.6 (8H, m), 3.80 (6H, s), 4.06 (6H, s), 5.68 (2H, s).

EXAMPLE 87

Following the elution of 2,2'-methylenebis(3,6-dimethoxy-1,4-benzoquinone) carried out the silica gel column chromatography in Example 79, the remaining fraction was further eluted and concentrated. The residue was crystallized from ethanol to obtain 150 mg of 2,5-dimethoxy-3,6-bis(2,5-dimethoxy-1,4-benzoquino-3-ylmethyl)-1,4-benzoquinone. Yellow needles crystals.

Melting point: 219°–219.5° C.

PMR, δ ppm (CDCl$_3$) 3.56 (4H, s), 3.81 (6H, s), 3.97 (6H, s), 4.03 (6H, s), 5.74 (2H, s).

EXAMPLE 88

Following the elution of 2,2'-pentamethylenebis[1,4-dimethoxy-3,6-bis(methoxymethoxy)benzene] carried out in the silica gel column chromatography in Example 38, the remaining fraction was further eluted with a mixed solvent of ethyl acetate : n-hexane (=3:7) to obtain 35 mg of 1,4-dimethoxy-2,5-bis(methoxymethoxy)-3,6-bis{5-[2,5-dimethoxy-3,6-bis(methoxymethoxy)phenyl]-pentyl}benzene. Colorless solid substance.

PMR, δ ppm (CDCl₃) 1.4–1.7 (12H, m), 2.5–2.8 (8H, m), 3.53 (6H, s), 3.57 (12H, s), 3.76 (6H, s), 3.79 (12H, s), 5.02 (4H, s), 5.04 (4H, s), 5.23 (4H, s), 6.65 (2H, s).

EXAMPLE 89

By a method similar to that described in Example 81, 500 mg of 1,4-dimethoxy-2,5-bis(methoxymethoxy)-3,6-bis{5-[2,5-dimethoxy-3,6-bis(methoxymethoxy)phenyl]-pentyl}benzene was treated for removal of methoxymethyl group and was oxidized, then the reaction product was purified by a silica gel column chromatography (developing solvent: 5% ethyl acetate-dichloromethane mixture) and crystallized from ethanol to obtain 150 mg of 2,5-dimethoxy-3,6-bis[5-(2,5-dimethoxy-1,4-benzoquinon-3-yl)pentyl]-1,4-benzoquinone. Orange needles crystals.

Melting point: 134°–135° C.

PMR, δ ppm (CDCl₃) 1.3–15. (12H, m), 2.3–2.5 (8H, m), 3.81 (6H, s), 3.99 (6H, s), 4.20 (6H, s), 5.73 (2H, s).

EXAMPLE 90

50 Milligrams of 2,2'-pentamethylenebis(3,6-dimethoxy-1,4-benzoquinone) was dissolved in 5 ml of solvent of methanol-tetrahydrofuran (3:2), to this solution was added 1 milliliter of 6N-hydrochloric acid and the mixture was stirred at room temperature for 4 hours. Next, the reaction mixture was diluted with 30 ml of water, and extracted three times with 15 ml of diethyl ether. The diethyl ether layers were combined together, washed with water, then washed with a saturated sodium chloride aqueous solution, dehydrated over anhydrous magnesium sulfate. This dried extract was concentrated by evaporation under reduced pressure, and the residue obtained was purified by means of a column chromatography [adsorbent: "Toyopearl HW40" manufactured by Toyo Soda Manufacturing Co., Ltd., Tokyo, Japan, developing solvent: chloroform-methanol (1:1)], to obtain 5 mg of 2,2'-pentamethylenebis(3-hydroxy-5-methoxy-1,4-benzoquinone). Orange powdery substance.

PMR, δ ppm (CDCl₃) 1.48 (6H, m), 2.43 (4H, t, J=7.0Hz), 3.85 (6H, s), 5.83 (2H, s), 7.22 (2H, s).

EXAMPLE 91

500 Milligrams of 2,2'-pentamethylenebis(1,4-dihydroxy-3,6-dimethoxybenzene) was suspended in 40 ml of deaerated dichloromethane under argon gas stream conditions, to this suspension was added 0.308 ml of acetyl chloride under ice-cooling conditions. Next, 0.528 ml of diisopropylethylamine was added thereto with stirring, the temperature of the reaction mixture was backed to room temperature by taking for 14 hours. The reaction mixture was poured into ice-water, and the dichloromethane layer was washed with water then concentrated. The residue obtained was purified by means of a silica gel column chromatography (eluent: ethyl acetate-benzene =1:4) to obtain 444 mg of 2,2'-pentamethylenebis(1,4-diacetoxy-3,6-dimethoxybenzene). Colorless needle-like cyrstals.

Melting point: 94.5°–95.0° C.

PMR, δ ppm (CDCl₃): 1.3–1.6 (6H, m), 2.27 (6H, s), 2.30 (6H, s), 2.4–2.6 (4H, m), 3.73 (12H, s), 6.54 (2H, s).

EXAMPLE 92

By using procedures similar to those described in Example 38, except that 202 mg of 1-[2,5-dimethoxy-3,6-bis(methoxymethoxy)phenyl]non-4-yne and 322 mg of 1-(5-bromopentyl)-2,5-dimethoxy-3,6-bis(methoxymethoxy)benzene were used in place of 1,4-dimethoxy-2,5-bis(methoxymethoxy)benzene and dibromopentane there was obtained 160 mg of 1,4-dimethoxy-2,5-bis(methoxymethoxy)-6-(4-nonynyl)-3-{5-(2,5-dimethoxy-3,6-bis(methoxymethoxy)phenyl]pentyl} benzene. Powdery substance.

PMR, δ ppm (CDCl₃): 0.90 (3H, t, J-7.1Hz), 1.35–1.55 (4H, m), 1.55–1.67 (6H, m), 1.67–1.84 (2H, m), 2.15 (2H, tt, J=7.12, 2.4Hz), 2.23 (2H, tt, J=7.12, 2.4Hz), 2.62 (2H, t, J=7.1Hz), 2.69 (2H, t, J=7.8Hz), 2.70 (2H, t, J=7.8 Hz), 3.53 (3H, s), 3.568 (3H, s), 3.572 (3H, s), 3.59 (3H, s), 3.75 (3H, s), 3.76 (3H, s), 3.788 (3H, s), 3.790 (3H, s), 4.98 (2H, s), 4.99 (2H, s), 5.08 (4H, s), 6.64 (1H, s).

EXAMPLE 93

By using procedures similar to those described in Example 81, except that, 150 mg of 1,4-dimethoxy-2,5-bis(methoxymethoxy)-6-(4-nonynyl)-3-{5-[2,5-dimethoxy-3,6-bis(methoxymethoxy)phenyl]pentyl}benzene was treated for removal of methoxymethyl group and was oxidized, there was obtained 72 mf og 2,5-dimethoxy-3-(4-nonynyl)-6-[5-(2,5-dimethoxy-1,4-benzoquinon-3-yl)pentyl]-1,4-benzoquinone. Orange powdery substance.

PMR, δ ppm (CDCl₃) 0.90 (3H, t, J=6.8Hz), 1.2–1.8 (12H, m), 2.1–2.3 (4H, m), 2.3–2.6 (6H, m), 4.01 (3H, s), 4.05 (3H, s), 4.06 (6H, s), 5.73 (1H, s).

EXAMPLE 94

By using procedures similar to those described in Example 76, except that 608 mg of 1-[2,5-dimethoxy 3,6-bis(methoxymethoxy)phenyl]non-4-yne was used in place of 1,4-dimethoxy-2,5-bis(methoxymethoxy)benzene, there was obtained 522 mg of 1,4-dimethoxy-2,5-bis(methoxymethoxy)-6-(nonynyl)-3-{3-[2,5-dimethoxy-3,6-bis(methoxymethoxy)phenyl]propyl}benzene. Colorless powdery substance.

PMR, δ ppm (CDCl₃) 0.90 (3H, t, J=7.0Hz), 1.4–1.5 (4H, m), 1.6–1.9 (4H, m), 2.1–2.3 (4H, m), 2.6–2.9 (6H, m), 3.52 (3H, s), 3.56 (3H, s), 3.57 (3H, s), 3.58 (3H, s), 3.750 (3H, s), 3.752 (3H, s), 3.77 (3H, s), 3.78 (3H, s), 4.99 (2H, s), 5.02 (2H, s), 5.03 (2H, s), 5.16 (2H, s), 6.63 (1H, s).

EXAMPLE 95

By using procedures similar to those described in Example 81, except that 523 mg of 1,4-dimethoxy-2,5-bis(methoxymethoxy)-6-(4-nonynyl)-3-{3-[2,5-dimethoxy-3,6-bis(methoxymethoxy)phenyl]propyl}benzene was treated for removal of methoxymethyl group and was oxidized to obtain 108 mg of 2,5-dimethoxy-3-(4-nonynyl)-6-[3-(2,5-dimethoxy-1,4-benzoquinon-3-yl)propyl]-1,4-benzoquinone. Orange powdery substance.

PMR, δ ppm (CDCl₃): 0.90 (3H, t, J=7.0Hz), 1.3–2.0 (8H, m), 2.0–2.3 (4H, m), 2.3–2.6 (6H, m), 3.80 (3H, s), 4.00 (6H, s), 4.06 (3H, s), 5.72 (1H, s).

EXAMPLE 96

10 Grams of 1,4-dimethoxy-2,5-bis(methoxymethoxy)benzene was dissolved in 200 ml of anhydrous toluene under argon gas stream conditions, to this solution were added 50 ml of hexamethylphosphoric triamide and 8.75 ml of N,N,N',N'-tetramethylethylenediamine (TMEDA), and the mixture was cooled in a dry ice-acetone mixture bath. To this cooled mixture was added dropwise 39 ml of n-butyllithium (1.5 M, n-hexane solution), then stirred the mixture for 30 minutes. Next, 8.9 ml of 1-iodobutane was added to the reaction mixture, and the temperature was back to room temperature by taking for 12 hours. By procedures similar to those described in Reference Example 1, the above-mentioned reaction mixture was purified to obtain 8.5 g of 3-butyl-1,4-dimethoxy-2,5-bis(methoxymethoxy)benzene. Colorless oily substance.

PMR, δ ppm (CDCl$_3$) 0.93 (3H, t, J=7.3Hz), 1.3–1.6 (4H, m), 2.67 (2H, t, J=7.3Hz), 3.53 (3H, s), 3.59 (3H, s), 3.79 (6H, s), 5.02 (2H, s), 5.17 (2H, s), 6.64 (1H, s).

EXAMPLE 97

By using procedures similar to those described in Example 38, except that 5 g of 3-butyl-1,4-dimethoxy-2,5-bis(methoxymethoxy)benzene was used in place of 1,4-dimethoxy-2,5-bis(methoxymethoxy)benzene, there was obtained 6.1 g of 1,4-dimethoxy-2,5-bis(methoxymethoxy)-6-butyl-3-{5-[2,5-dimethoxy-3,6-bis(methoxymethoxy)phenyl]pentyl}benzene. Colorless solid substance.

PMR, δ ppm (CDCl$_3$): 0.94 (3H, t, J=7.0Hz), 1.3–1.7 (10H, m), 2.6–2.75 (6H, m), 3.53 (3H, s), 3.57 (3H, s), 3.58 (3H, s), 3.59 (3H, s), 3.75 (3H, s), 3.76 (3H, s), 3.79 (6H, s), 5.02 (2H, s), 5.05 (4H, s), 5.17 (2H, s),

EXAMPLE 98

By using procedures similar to those described in Example 81, except that, 1 g of 1,4-dimethoxy-2,5-bis(methoxymethoxy)-6-butyl-3-{5-[2,5-dimethoxy-3,6-bis(methoxymethoxy)phenyl]pentyl}benzene was treated for removal of methoxymethyl group and was oxidized to obtain mg of 2,5-dimethoxy-3-butyl-6-[5-(2,5-dimethoxy-1,4-benzoquinon-3-yl)pentyl]-1,4-benzoquinone. Orange powdery substance.

PMR, δ ppm (CDCl$_3$) 0.90 (3H, t, J=7.0Hz), 1.3–1.5 (10H, m), 2.3–2.5 (6H, m), 3.81 (3H, s), 3.99 (6H, s), 4.06 (3H, s), 5.73 (1H, s).

EXAMPLE 99

Under argon gas stream conditions 2 g of 1,4-dimethoxy-2,5-bis(methoxymethoxy)-6-butyl-3-{5-[2,5-dimethoxy-3,6-bis(methoxymethoxy)phenyl]pentyl}benzene was dissolved in 50 ml of a mixed solvent of anhydrous toluene-tetrahydrofuran (4:1), to this solution were added 10 ml of hexamethylphosphoric triamide and 0.94 ml of N,N,N',N'-tetramethylethylenediamine, then the whole mixture was cooled on a dry ice-acetone bath. 4 Milliliter of n-butyllithium (1.5 M, n-hexane solution) was added dropwise to the reaction mixture and stirred 30 minutes. Next, oxygen gas was bubbled into the reaction mixture for 30 minutes, then the temperature of the reaction mixture was returned back to room temperature by taking for 4 hours. The reaction mixture was concentrated, to the residue obtained was added 100 ml of ethyl acetate, then the ethyl acetate layer was washed twice with 30 ml of a saturated sodium bisulfite aqueous solution, once with 30 ml of water, further washed once with 30 ml of a saturated sodium chloride aqueous solution. The ethyl acetate layer was dried over anhydrous magnesium sulfate, and concentrated, then the residue obtained was purified by a silica gel column chromatography (eluent: ethyl acetate-n-hexane=1:9) to obtain 1.3 g of 1,4-dimethoxy-2,5-bis(methoxymethoxy)-6-butyl-3{5-[2,5-dimethoxy-3,6-bis(methoxymethoxy)-4-hydroxyphenyl]pentyl} benzene. Colorless oily substance.

PMR, δ ppm (CDCl$_3$) 0.93 (3H, t, J=6.5Hz), 1.3–1.7 (10H, m), 2.5–2.7 (6H, m), 3.56 (6H, s), 3.57 (3H, s), 3.58 (3H, s), 3.76 (6H, s), 3.79 (3H, s), 3.83 (3H, s), 5.03 (4H, s), 5.06 (2H, s), 5.08 (2H, s), 6.24 (1H, s).

EXAMPLE 100

1.3 Grams of 1,4-dimethoxy-2,5-bis(methoxymethoxy)-6-butyl-3-{5-[2,5-dimethoxy-3,6-bis(methoxymethoxy)-4-hydroxyphenyl]pentyl}benzene was dissolved in 50 ml of methanol, to this solution was added an excess amount of diazomethane-ether solution was added and the reaction mixture was stirred for 3 hours. The reaction mixture was concentrated to obtain 1.3 g of 1,4-dimethoxy-2,5-bis(methoxymethoxy)-6-butyl-3-{5-[2,4,5-trimethoxy-3,6-bis(methoxymethoxy)phenyl]pentyl}benzene. Colorless oily substance.

PMR, δ ppm (CDCl$_3$) 0.93 (3H, t, J=6.6Hz), 1.3–1.6 (10H, m), 2.5–2.7 (6H, m), 3.56 (6H, s), 3.58 (3H, s), 3.62 (3H, s), 3.76 (6H, s), 3.81 (3H, s), 3.82 (3H, s), 3.90 (3H, s), 5.05 (4H, s), 5.06 (2H, s), 5.10 (2H, s).

EXAMPLE 101

By using procedures similar to those described in Example 81, except that 1.3 g of 1,4-dimethoxy-2,5-bis(methoxymethoxy)-6-butyl-3-{5-[2,4,5-trimethoxy-3,6-bis(methoxymethoxy)phenyl]pentyl}benzene was treated for removal of methoxymethyl group and was oxidized, there was obtained 600 mg of 2,5-dimethoxy-3-butyl-6-[5-(2,3,5-trimethoxy-1,4-benzoquinon-6-yl)pentyl]-1,4-benzoquinone. Red powder substance.

PMR, δ ppm (CDCl$_3$) 0.93 (3H, t, J=6.5Hz), 1.3–1.5 (10H, m), 2.3–2.5 (6H, m), 3.97 (3H, s), 3.99 (9H, s), 4.02 (3H, s).

EXAMPLE 102

By using procedures similar to those described in Example 99, except that 1 g of 1,4-dimethoxy-2,5-bis(methoxymethoxy)-6-butyl-3-{5-[2,5-dimethoxy-3,6-bis(methoxymethoxy)phenyl]pentyl}benzene was reacted with 0.3 ml of ethyl chloroformate in place of oxygen gas, there was obtained 1.3 g of 1,4-dimethoxy-2,5-bis(methoxymethoxy)-6-butyl-3-{5-[2,5-dimethoxy-3,6-bis(methoxymethoxy)-4-(ethoxycarbonyl)phenyl]pentyl}benzene. Colorless oily substance.

PMR, δ ppm (CDCl$_3$) 0.95 (3H, t, J=7.0Hz), 1.40 (3H, t, J=7.0Hz), 1.4–1.7 (10H, m), 2.5–2.7 (6H, m), 3.53 (3H, s), 3.57 (3H, s), 3.58 (3H, s), 3.59 (6H, s), 3.79 (6H, s), 3.80 (3H, s), 3.83 (3H, s), 4.40 (2H, q, J=7.0Hz), 5.05 (2H, s), 5.06 (2H, s), 5.07 (2H, s), 5.09 (2H, s).

EXAMPLE 103

By using procedures similar to those described in Example 99, except that 2 g of 1,1'-pentamethylenebis[2,5-dimethoxy-3,6-bis(methoxymethoxy)benzene] was oxidized in place of 1,4-dimethoxy-2,5-bis(methoxymethoxy)- 6-butyl-3-{5-[2,5-dimethoxy-3,6-bis(methoxymethoxy)phenyl]pentyl}benzene, and the reaction product was purified by a silica gel column chromatography, there were obtained 250 mg of 1,4-dimethoxy-2,5-bis(methoxymethoxy)-6-hydroxy-3-{5-[2,5-dimethoxy-3,6-bis(methoxymethoxy)phenyl]pentyl}benzene and 80 mg of 1,1'-pentamethylenebis[2,5- dimethoxy-4-hydroxy-3,6-bis(methoxymethoxy)benzene]. Colorless oily substance. The former compound:

PMR, δ ppm (CDCl₃) 1.4–1.7 (6H, m), 2.5–2.7 (4H, m), 3.53 (3H, s), 3.55 (3H, s), 3.574 (3H, s), 3.578 (3H, s), 3.60 (3H, s), 3.78 (3H, s), 3.79 (3H, s), 3.85 (3H, s), 5.02 (2H, s), 5.07 (2H, s), 5.10 (2H, s), 5.17 (2H, s), 6.24 (1H, s), 6.64 (1H, s).

The latter compound:

PMR, δ ppm (CDCl₃) 1.4–1.7 (6H, m), 2.5–2.7 (4H, m), 3.57 (6H, s), 3.60 (6H, s), 3.79 (6H, s), 3.85 (6H, s), 5.08 (4H, s), 5.10 (4H, s), 6.25 (2H, s).

EXAMPLE 104

By using procedures similar to those described in Example 100, except that in place of 1,4-dimethoxy-2,5-bis(methoxymethoxy)-6-butyl-3-{5-[2,5-dimethoxy-3,6-bis(methoxymethoxy)-4-hydroxyphenyl]pentyl}benzene, 250 mg of 1,4-dimethoxy-2,5-bis(methoxymethoxy)-6-hydroxy- 3-{5-[2,5-dimethoxy-3,6-bis(methoxymethoxy)phenyl]pentyl}benzene was methylated, there was prepared 250 mg of 2,4,5-trimethoxy-3,6-bis(methoxymethoxy)-1-{5-[2,5-dimethoxy-3,6-bis(methoxymethoxy)phenyl]pentyl}benzene. Colorless oily substance.

PMR, δ ppm (CDCl₃): 1.4–1.7 (6H, m), 2.7–2.8 (4H, m), 3.53 (3H, s), 3.58 (6H, s), 3.61 (3H, s), 3.791 (3H, s), 3.795 (3H, s), 3.81 (3H, s), 3.83 (3H, s), 3.90 (3H, s), 5.02 (2H, s), 5.08 (2H, s), 5.09 (2H, s), 5.18 (2H, s), 6.65 (1H, s).

EXAMPLE 105

By using procedures similar to those described in Example 100, except that 80 mg of 1,1'-pentamethylenebis[2,5-dimethoxy-4-hydroxy-3,6-bis(methoxymethoxy)benzene]. was used, there was prepared 80 mg of 1,1'-pentamethylenebis[2,4,5-trimethoxy-3,6-bis(methoxymethoxy)benzene]. Colorless oily substance.

PMR, δ ppm (CDCl₃): 1.4–1.7 (6H, m), 2.5–2.7 (4H, m), 3.57 (6H, s), 3.60 (6H, s), 3.82 (6H, s), 3.83 (6H, s), 3.90 (6H, s), 5.07 (4H, s), 5.09 (4H, s).

EXAMPLE 106

By using procedures similar to those described in Example 81, except that 250 mg of 2,4,5-trimethoxy-3,6-bis(methoxymethoxy)-1-{5-[2,5-dimethoxy-3,6-bis(methoxymethoxy)phenyl]pentyl}benzene was treated for the removal of methoxymethyl group and was oxidized, there was prepared 50 mg of 2,3,5-trimethoxy-6-[5-(2,5-dimethoxy-1,4-benzoquinon-3-yl)pentyl]-1,4-benzoquinone. Yellow needles crystals.

Melting point: 69°–70° C.

PMR, δ ppm (CDCl₃): 1.3–1.7 (6H, m), 2.3–2.5 (4H, m), 3.81 (3H, s), 3.97 (3H, s), 3.99 (3H, s), 4.02 (3H, s), 4.05 (3H, s), 5.73 (1H, s).

EXAMPLE 107

By using procedures similar to those described in Example 81, except that 80 mg of 1,1'-pentamethylene-bis-[2,4,5-trimethoxy-3,6-bis(methoxymethoxy)benzene] was treated for the removal of methoxymethyl group and was oxidized, there was prepared 10 mg of 2,2'-pentamethylenebis-(3,5,6-trimethoxy-1,4-benzoquinone). Yellow needles.

Melting point: 108°–109° C.

PMR, δ ppm (CDCl₃) 1.3–1.6 (6H, m), 2.3–2.5 (4H, m), 3.97 (6H, s), 3.99 (6H, s), 4.02 (6H, s).

EXAMPLE 108

1.51 Grams of 2,2'-pentamethylenebis[1,4-dimethoxy-3,6-bis(methoxymethoxy)benzene] was dissolved in a mixed solvent of 40 ml of tetrahydrofuran with 4 ml of hexamethylphosphoric triamide, to this solution was added 0.55 ml of N,N,N',N'-tetramethylethylenediamine and the whole mixture was cooled to −78° C., on a dry ice-acetone bath. Then, 2.41 ml of n-butyllithium (1.6 M, n-hexane solution) was added dropwise to the reaction mixture and stirred for 30 minutes. Next, 0.25 ml of dimethyl sulfide was added to the reaction mixture and stirred overnight. The solvent was removed by evaporation under reduced pressure, then the residue obtained was extracted twice with 100 ml of ethyl acetate, then the ethyl acetate layer was washed twice with 100 ml of water, and twice with a saturated sodium chloride aqueous solution, then dried over anhydrous magnesium sulfate. The solvent was removed by evaporation under reduced pressure, and the residue obtained was purified by means of a preparative thin layer chromatography (thickness: 2 mm, adsorbent: Merck Art 5717 silica gel, developing solvent: 20% ethyl acetate-n-hexane). There were obtained 572 mg of 1-[2,5-dimethoxy-3,6-bis(methoxymethoxy)phenyl]5-[2,5-dimethoxy-3,6-bis(methoxymethoxy)-4-(methylthio)phenyl]pentane, as well as 522 mg of 2,2'-pentamethylenebis[1,4-dimethoxy-3,6-bis(methoxymethoxy)-5-(methylthio)benzene].

(1) The former compound: Colorless oily substance

PMR, δ ppm (CDCl₃) 1.4–1.7 (6H, m), 2.44 (3H, s), 2.58–2.78 (4H, m), 3.53 (3H, s), 3.58 (6H, s), 3.67 (3H, s), 3.80 (9H, s), 3.83 (3H, s), 5.02 (2H, s), 5.08 (2H, s), 5.13 (2H, s), 5.18 (2H, s), 6.65 (1H, s).

(2) The latter compound: Colorless oily substance

PMR, δ ppm (CDCl₃): 1.4–1.7 (6H, m), 2.45 (6H, s), 2.67 (4H, t, J=7.3Hz), 3.58 (6H, s), 3.68 (6H, s), 3.81 (6H, s), 3.84 (6H, s), 5.09 (4H, s), 5.14 (4H, s).

EXAMPLE 109

(1) 308 Milligrams (1.59 mM) of 1,4-dimethoxy-2,3,5,6-tetramethylbenzene was dissolved in a mixed solvent of 9 ml of anhydrous tetrahydrofuran with 0.6 ml of hexamethylphosphoric triamide. Next, 0.29 ml of N,N,N',N'-tetramethylethylenediamine (TMEDA) was added thereto, and the whole mixture was cooled to −30° C. under an atmosphere of argon. Then 1.2 ml (1.6 M, solution) of n-butyllithium was added dropwise to the reaction mixture and stirred for 20 minutes. Then a solution prepared by dissolving 689 mg (1.90 mM) of 1,4-dimethoxy-2-(4-iodobutyl)-3,5,6-trimethylbenzene in 5 ml of anhydrous tetrahydrofuran was added to the reaction mixture and temperature of the reaction mixture was backed to room temperature by taking 15 hours. After addition of a small amount of water to the reaction mixture, the tetrahydrofuran was removed by evaporation under a reduced pressure. The residue obtained was dissolved in 30 ml of diethyl ether, and the organic layer was washed three times with water, then washed once with 10 ml of a saturated sodium chloride aqueous solution The organic layer was dried over anhydrous magnesium sulfate, and concentrated under reduced pressure to obtain 750 mg of a crude product This crude product was used in the next reaction step without purified. (2) 750 Milligrams of the crude product obtained in the above-mentioned reaction (1), was dissolved in 35 ml of a mixed solvent of acetonitrile-acetone (2:5), next 15 ml of water was added thereto and the solution was cooled at −20° C. The solution prepared by dissolving 1 g of ammonium cerium nitrate in 5 ml of water was added thereto. Then the temperature of the reaction mixture was gradually elevated from -20° C. to room temperature by taking 2 hours with stirring conditions. Without removal of the solvent, 120 ml of ethyl acetate was added to the reaction mixture. The organic layer was washed three times with 30 ml of water, then washed once with 30 ml of a saturated sodium chloride aqueous solution, then dried over anhydrous magnesium sulfate. The dried ethyl acetate solution was concentrated under reduced pressure, the residue obtained was treated by means of a silica gel thin layer chromatography (adsorbent: "Silica gel 60", E. Merck A. G., thickness: 1 mm, developer: 5% ethyl acetate-benzene). There was obtained 43 mg of 2,2'-pentamethylenebis(3,5,6-trimethyl-1,4-benzoquinone).
Light yellow powdery substance.
Melting point: 137.5°–138° C.
PMR, δ ppm (CDCl$_3$): 1.32–1.48 (6H, m), 2.01 (12H, s), 2.02 (6H, s), 2.39–2.55 (4H, m).

EXAMPLE 110

259 Milligrams of 1,4-dimethoxy-2,5-bis(methoxymethoxy)benzene was dissolved in a mixed solvent of 12 ml of toluene with 3 ml of hexamethylphosphoric triamide, and further 0.303 ml of N,N,N',N'-tetramethylethylenediamine was added thereto, and the mixture was cooled to −78° C. on a dry ice-acetone mixture bath. 1.34 Milliliters of n-butyllithium (1.6 M, n-hexane solution) was added dropwise to the reaction mixture and stirred for 20 minutes. Then 0.14 ml of dimethyl disulfide was added dropwise thereto, and reacted for additional 2 hours with stirring. The reaction mixture was warmed until room temperature, then 30 ml of diethyl ether was added thereto, and the organic layer was washed three times with 20 ml of water, then washed three times with 20 ml of a saturated sodium chloride aqueous solution, and dried over anhydrous magnesium sulfate. The diethyl ether extract was concentrated under a reduce pressure, the residue obtained was purified by means of a thin layer chromatography (thickness: 2 mm, adsorbent: silica gel, developing solvent: 40%-ethyl acetate-n-hexane). There was obtained 152 mg of 1,4-dimethoxy-2,5-bis(methoxymethoxy)-3-methylthiobenzene. Colorless oily substance.
PMR, δ ppm (CDCl$_3$) 2.46 (3H, s), 3.54 (3H, s), 3.67 (3H, s), 3.82 (3H, s), 3.85 (3H, s), 5.12 (2H, s), 5.19 (2H, s), 6.78 (1H, s).

EXAMPLE 111

150 Milligrams of 1,4-dimethoxy-2,5-bis(methoxymethoxy)-3-(methylthio)benzene was dissolved in a mixed solvent of 4 ml of toluene with 1 ml of hexamethylphosphoric triamide, to this solution was added 0.104 ml of N,N,N',N'-tetramethylethylenediamine was added, then the whole mixture was cooled to −78° C. on a dry ice-acetone bath. 0.466 Milliliter of n-butyllithium (1.6 M, n-hexane solution) was added dropwise thereto and stirred for 30 minutes. Next, 8 ml of toluene solution containing 269 mg of 1-(5-iodopent-1-yl)-2,5-dimethoxy-3,6-bis(methoxymethoxy)benzene was added dropwise and the reaction mixture was stirred overnight. The reaction mixture was warmed to room temperature, then 30 ml of diethyl ether was added thereto, the organic layer was washed three times with 20 ml of water then washed twice with a saturated sodium chloride aqueous solution, and dried over anhydrous magnesium sulfate. The diethyl ether solution was concentrated under reduced pressure, the residue obtained was purified by means of a preparative thin layer chromatography (thickness: 2 mm, adsorbent: Merck Art 5717 silica gel, developing solvent: 40% ethyl acetate-n-hexane). There was obtained 120 mg of 1-[2,5-dimethoxy3,6-bis(methoxymethoxy)phenyl]-5-[2,5-dimethoxy-3,6-bis(methoxymethoxy)-4-(methylthio)phenyl]pentane as in the form of colorless oily substance.
PMR, δ ppm (CDCl$_3$): The physical properties of this compound were the same as indicated by the first objective compound [Compound (1)]obtained in Example 108, prepared by the different process.

EXAMPLE 112

573 Milligrams of 1-[2,5-dimethoxy-3,6-bis(methoxymethoxy)phenyl]-5-[2,5-dimethoxy-3,6-bis(methoxymethoxy)-4-(methylthio)phenyl]pentane was dissolved in a mixed solvent of 5 ml of tetrahydrofuran with 5 ml of isopropanol, then to this solution was added 2 ml of a solution (tetrahydrofuran:isopropanol=1:1) containing 20%-hydrogen chloride. This reaction mixture was stirred for 2 hours at 65° C. on an oil bath under an atmosphere of argon. The solvent was removed by evaporation under reduced pressure, to the residue obtained was added some amount of benzene and treated under an azeotropic distillation. The residue was dissolved in 10 ml of methanol, and a small amount of sodium hydrogen carbonate was added thereto then oxygen gas was bubbled into the mixture for 4 hours at 60° C. Sodium hydrogen carbonate was removed by filtration, and after several crystallization from the methanol, 204 mg of 1-(2,5-dimethoxy)1,4-benzoquinon-3-yl)-5-(2,5-dimethoxy)-6-methylthio-1,4-benzoquinon-3-yl)pentane was obtained. Dark reddish powdery crystals.
Melting point: 75°–77° C.
PMR, δ ppm (CDCl$_3$): 31–1.46 (6H, m), 2.40 (2H, t, J=7.3Hz), 2.43 (2H, t, J=7.3Hz), 2.50 (3H, s), 3.81 (3H, s), 4.00 (3H, s), 4.06 (3H, s), 4.08 (3H, s), 5.73 (1H, s).

EXAMPLE 113

1.0 Gram of 2,2'-pentamethylenbis[1,4-dimethoxy-3,6-bis(methoxymethoxy)-5-(methylthio)benzene] was dissolved in a mixed solvent of 10 ml of tetrahydrofuran with 10 ml of isopropanol, to this solution was added 2 ml of a solution (tetrahydrofuran:isopropanol=1:1) containing 20%-hydrogen chloride. This reaction mixture was stirred for 2 hours at 65° C. on an oil bath under an atmosphere of argon. The solvent was removed by evaporation under reduced pressure, to the residue obtained was added some amount of benzene and treated under an azeotropic distillation, then the residue obtained was dissolved in 30 ml of methanol, further added a small amount of sodium hydrogen carbonate, then the mixture was stirred for 30 minutes at 60° C. The sodium hydrogen carbonate was removed by filtration, and after several crystallization from the methal, 374 mg of 2,2'-pentamethylenebis(3,6-dimethoxy-5-methylthio-1,4-benzoquinone) was obtained. Dark reddish needles crystals.
Melting point: 64°–65° C.
PMR, δ ppm (CDCl$_3$): 1.3–1.5 (6H, m) 2.40 (4H t, J=7.3Hz), 2.50 (6H, s), 4.00 (6H, s), 4.08 (6H, s).

EXAMPLE 114

998 Milligrams of 2,2'-pentamethylenebis[1,4-dimethoxy-3,6-bis(methoxymethoxy)benzene] was dissolved in a mixed solvent of 30 ml of tetrahydrofuran with 3 ml of hexamethylphosphoric triamide, to this solution was added 1.03 ml of N,N,N',N'-tetramethylethylenediamine, was cooled to −78° C. on a dry ice-acetone mixture bath. 4.56 Milliliters of n-butyllithium (1.6 M, n-hexane solution) was added dropwise to the reaction mixture and stirred for 30 minutes. Next, 15 ml of tetrahydrofuran solution containing 1.22 g of N-bromosuccinimide was added dropwise and the reaction mixture was stirred overnight. The solvent was removed under reduced pressure, and the residue obtained was extracted twice with 50 ml of diethyl ether, and the diethyl ether layer was washed twice with 50 ml of water, and washed twice with 50 ml of a saturated sodium chloride aqueous solution, then dried over anhydrous magnesium sulfate. The diethyl ether solution was concentrated under reduced pressure, the residue obtained was purified by means of a preparative thin layer chromatography (thickness: 2 mm, adsorbent: Merck 5717 silica gel, developing solvent: 40% ethyl acetate-n-hexane). There were obtained 155 mg of 1-[2,5-dimethoxy-3,6-bis(methoxymethoxy)phenyl]-5-[2,5-dimethoxy-3,6-bis(methoxymethoxy)-4-bromophenyl]pentane, as well as 22 mg of 2,2'-pentamethylenebis[1,4-dimethoxy-3,6-bis(methoxymethoxy)-5-bromobenzene].

(1) The former compound: Colorless needles crystals
Melting point: 86.5°–87° C.
PMR, δ ppm (CDCl): 1.4–1.7 (6H, m), 2.55–2.75 (4H, m), 3.53 (3H, s), 3.58 (6H, s), 3.67 (3H, s), 3.80 (9H, s), 3.81 (3H, s), 5.02 (2H, s), 5.08 (2H, s), 5.13 (2H, s), 5.18 (2H, s), 6.65 (1H, s).

(2) The latter compound: Colorless needles crystals
Melting point: 96°–97° C.
PMR, δ ppm (CDCl$_3$) 1.4–1.7 (6H, m), 2.65 (4H, t, J=7.3Hz), 3.58 (6H, s), 3.68 (6H, s), 3.807 (6H, s), 3.812 (6H, s), 5.09 (4H, s), 5.14 (4H, s).

EXAMPLE 115

1.53 Grams of 2,2'-pentamethylenebis[1,4-dimethoxy-3,6-bis(methoxymethoxy)benzene] was dissolved in a mixed solvent of 40 ml of tetrahydrofuran with 4 ml of hexamethylphosphoric triamide, to this solution was added 0.79 ml of N,N,N',N'-tetramethylethylenediamine, then this mixture was cooled to −78° C. on a dry ice-acetone mixture bath. 3.49 Milliliters of n-butyllithium (1.6 M, n-hexane solution) was added dropwise to the reaction mixture and stirred for 30 minutes. Next, 15 ml of tetrahydrofuran solution containing 1.18 g of N-iodosuccinimide was added dropwise and the reaction mixture was stirred overnight. The solvent was removed under reduced pressure, and the residue obtained was extracted twice with 100 ml of diethyl ether, and the diethyl ether layer was washed twice with 100 ml of water, and washed twice with 100 ml of a saturated sodium chloride aqueous solution, then dried over anhydrous magnesium sulfate. The dried diethyl ether extract was concentrated under reduced pressure, the residue obtained was purified by means of a separative thin layer chromatography (thickness: 2 mm, adsorbent: Merk 5717 silica gel, developing solvent: ethyl acetate-dichloromethane (1:9). There were obtained 685 mg of 1-[2,5-dimethoxy-3,6-bis(methoxymethoxy)phenyl]-5-[2,5-dimethoxy-3,6-bis(methoxymethoxy)-4-iodophenyl]pentane, as well as 575 mg of 2,2'-pentamethylenebis[1,4-dimethoxy-3,6-bis(methoxymethoxy)-5-iodobenzene].

(1) The former compound: Colorless needles crystals
Melting point: 79°–80° C.
NMR, δ ppm (CDCl$_3$) 1.40–1.70 (6H, m), 2.65 (2H, t, J=7.2Hz), 2.68 (2H, t, J=7.2Hz), 3.53 (3H, s), 3.58 (6H, s), 3.69 (3H, s), 3.78 (6H, s), 3.789 (3H, s), 3.794 (3H, s), 5.02 (2H, s), 5.07 (2H, s), 5.12 (2H, s), 5.18 (2H, s), 6.65 (1H, s).

(2) The latter compound: Colorless needles crystals
Melting point: 110°–112° C.
NMR, δ ppm (CDCl$_3$): 1.40–1.70 (6H, m), 2.65 (4H, t, J=7.3Hz), 3.58 (6H, s), 3.70 (6H, s), 3.79 (12H, s), 5.08 (4H, s), 5.13 (4H, s).

EXAMPLE 116

(1) 555 Milligrams (0.95 mM) of 2,2'-pentamethylenebis{1,4-dimethoxy-3,6-bis[(methoxymethoxy)-benzene]} was dissolved in a mixed solvent of 22.2 ml of anhydrous tetrahydrofuran with 4 ml of hexamethylphosphoryl triamide, to this solution was added 0.16 ml of N,N,N',N'-tetramethylethylenediamine (TMEDA), then this solution was cooled to −78° C. under an atmosphere of argon. 0.66 Milliliter of n-butyllithium (1.6 M, solution) was added dropwise to the reaction mixture and stirred for 20 minutes. Next, 0.10 ml (1.05 mM) of ethyl chloroformate was added to the reaction mixture, and stirred at −78° C. for 2 hours. The temperature of the reaction mixture was returned back to room temperature by taking 10 hours. A small amount of water was added to the reaction mixture and tetrahydrofuran was removed under reduced pressure. The residue obtained was dissolved in 60 ml of diethyl ether, the organic layer was washed three times with 20 ml of water, then washed once with 20 ml of a saturated sodium chloride aqueous solution, next dried over anhydrous magnesium sulfate. The diethyl ether solution was concentrated to obtain 557 mg of a crude product. This crude product was used to the next reaction step without purified. (2) 557 Milligrams of the above-mentioned crude product was dissolved in 12 ml of a mixed solvent of ethanol-tetrahydrofuran (1:1), to this solution was added 1.2 ml of a mixture of ethanol-tetrahydrofuran (1:1) containing 20%-hydrogen chloride under an atmosphere of argon at room temperature. The temperature of the reaction mixture was elevated to 60° C. and stirred for 2 hours. The solvent was removed under reduced pressure, to the residue obtained was added 10 ml of benzene, and again treated under reduced pressure to remove hydrogen chloride. The residue obtained was dissolved in 15 ml of acetonitrile, to this solution was added 1.5 ml of an acetonitrile solution of complex Cu$_4$Cl$_4$O$_2$ (CH$_3$CN)$_3$ (which was prepared by adding 1 g of cuprous chloride to 25 ml of acetonitrile under bubbling oxygen gas) and the reaction mixture was stirred for 30 minutes under oxygen gas stream conditions. The solvent was removed under reduced pressure, the residue obtained was dissolved in 60 ml of ethyl acetate, and the organic layer was washed three times with 20 ml of water, then washed once with 20 ml of a saturated sodium chloride aqueous solution. The organic layer was dried over anhydrous magnesium sulfate, and concentrated under reduced pressure. The residue obtained was tread by a silica gel column chromatography, by using as eluting solvent, benzenehexane mixtures in which the mixing ratio of the benzene was changed from 5 to 8% stepwise. There was obtained 110 mg of 2,5-dimethoxy-3-ethoxycarbonyl-6-[5-(2,5-dimethoxy-1,4-benzoquinon-3-yl)pentyl]-1,4-benzoquinone. Reddish oily substance.

PMR, δ ppm (CDCl$_3$) 1.20–1.50 (6H, m), 1.38 (3H, t, J=7.2Hz), 2.31–2.47 (4H, m), 3.81 (3H, s), 4.05 (3H, s), 4.06 (6H, s), 4.38 (2H, q, J=7.2Hz), 5.73 (1H, s).

EXAMPLE 117

By procedures similar to those described in Example 116, except that 1.2 g of 1,4-dimethoxy-2,5-bis(methoxymethoxy)-6-butyl-3-{5-[2,5-dimethoxy-3,6-bis(methoxymethoxy)-4-(ethoxycarbonyl)phenyl]pentyl}benzene was treated for the removal of methoxymethyl group and was oxidized, there was obtained 230 mg of 2,5-dimethoxy-3-butyl-6-[5-(2,5-dimethoxy-6-ethoxycarbonyl-1,4-benzoquinon-3-yl)pentyl]-1,4-benzoquinone. Yellow oily substance.

PMR, δ ppm (CDCl$_3$) 0.92 (3H, t, J=6.7Hz), 1.49 (3H, t, J=7.3Hz), 1.3–1.6 (10H, m), 2.3–2.5 (4H, m), 2.70 (2H, t, J=6.8Hz), 3.79 (3H, s), 3.84 (3H, s), 3.99 (6H, s), 4.46 (2H, q, J=7.3Hz).

EXAMPLE 118

3.083 Grams (5.28 mM) of 2,2'-pentamethylenebis[1,4-dimethoxy-3,6-bis(methoxymethoxy)benzene] was dissolved in a mixed solvent of 65 ml of anhydrous tetrahydrofuran with 10.8 ml of hexamethylphosphoryl triamide, to this solution was added 3.7 ml of N,N,N',N'-tetramethylethylenediamine (TMEDA) and the whole mixture was cooled to −78° C. under an atmosphere of argon gas. 15.8 Milliliters of n-butyllithium (1.6M solution) was added dropwise to the reaction mixture, and stirred for 90 minutes. Next, 2.37 ml (24.9 mM) of ethyl chloroformate was added to the reaction mixture, and the whole mixture was stirred for 3 hours at −78° C. Temperature of the reaction mixture was returned back to room temperature by taking 10 hours, and a small amount of water was added thereto and tetrahydrofuran was removed by evaporation under a reduced pressure. To the residue obtained was added 200 ml of 0.1N-hydrochloric acid and extracted three times with 80 ml of a mixed solvent of diethyl ether-benzene (1:1). The organic layer was washed three times with 50 ml of water, next washed once with 50 ml of a saturated sodium hydrogen carbonate aqueous solution, then washed once with 50 ml of a saturated sodium chloride aqueous solution, and dried over anhydrous magnesium sulfate. The organic layer was concentrated under a reduced pressure, the residue obtained was treated by means of a silica gel chromatography (adsorbent: 170 g of a mixture of "Wakogel C-200" with Silica gel, manufactured by Mallinckrodt Inc., N.J., U. S. A. and eluted with benzene, there was obtained 2.0 g of 2,2'-pentamethylene-bis[1,4-dimethoxy-3,6-bis(methoxymethoxy)-5-(ethoxycarbonyl)benzene]. Light yellow oily substance.

PMR, δ ppm (CDCl$_3$) 1.18–1.76 (6H, m), 1.38 (6H, t, J=7.5Hz), 2.67 (4H, brt, J=8.4Hz), 3.52 (6H, s), 3.57 (6H, s), 3.80 (6H, s), 3.82 (6H, s), 4.38 (4H, q, J=7.5Hz), 5.03 (4H, s), 5.07 (4H, s).

EXAMPLE 119

1.781 Grams (2.44 mM) of 2,2'-pentamethylene-bis[1,4-dimethoxy-3,6-bis(methoxymethoxy)-5-ethoxycarbonylbenzene] was dissolved in 36 ml of a mixed solvent of ethanol-tetrahydrofuran (1:1), to this solution was added 5 ml of a mixed solvent of ethanol-tetrahydrofuran (1:1), containing 20%-hydrogen chloride, under an atmosphere of argon gas, the reaction mixture was stirred for 2.5 hours at 80° C. The solvent was removed under a reduced pressure, to the residue obtained was added 30 ml of benzene, this mixture again treated under reduced pressure to remove hydrogen chloride. There were obtained 1.762 g of a crude product, which was then dissolved in 70 ml of acetonitrile, to this solution was added 15 ml of acetonitrile solution of complex of Cu$_4$Cl$_4$O$_2$ (CH$_3$CN)$_3$ (which was prepared by adding 1 g of cuprous chloride in 25 ml of acetonitrile under bubbling oxygen gas), and the reaction mixture was stirred for 30 minutes under oxygen gas stream conditions. The solvent was removed under reduced pressure, the residue obtained was dissolved in 120 ml of ethyl acetate, the organic layer was washed three times with 40 ml of water, next washed once with 40 ml of a saturated sodium chloride aqueous solution, then dried over anhydrous magnesium sulfate, and concentrated under reduced pressure. The residue obtained was treated by means of a silica gel column chromatography (diameter: 3.2 cm, adsorbent: "Wakogel C-300" 98 g), and eluted with a mixed solvent of benzene-ethyl acetate (16:1) to obtain 604 mg of 6,6'-pentamethylenebis(2,5-dimethoxy-3-ethoxycarbonyl-1,4-benzoquinone). Reddish oily substance.

PMR, δ ppm (CDCl$_3$) 1.10–1.50 (6H, m), 1.38 (6H, t, J=7.2Hz), 2.41 (4H, brt, J=7.8Hz), 4.05 (6H, s), 4.07 (6H, s), 4.38 (4H, q, J=7.2Hz).

EXAMPLE 120

1.169 Grams (2.00 mM) of 2,2'-pentamethylenebis[1,4-dimethoxy-3,6-bis(methoxymethoxy)benzene] was dissolved in a mixed solvent of 30 ml of anhydrous tetrahydrofuran with 5 ml of hexamethylphosphoric triamide, to this solution was added 0.35 ml of N,N,N',N'-tetramethylethylenediamine (TMEDA) and the whole mixture was cooled to −78° C. under an atmosphere of argon gas. Then 1.5 ml of n-butyllithium (1.6M, solution) was added dropwise to the reaction mixture and stirred for 20 minutes. Next, 10 ml of solution prepared by dissolving 321 mg (2.40 mM) of N-chlorosuccinimide in 10 ml of anhydrous tetrahydrofuran was added to the reaction mixture, then the temperature of the reaction mixture was elevated from −78° C. to a room temperature by taking 7 hours gradually, then a small amount of water was added thereto and tetrahydrofuran was removed under a reduced pressure. The residue obtained was dissolved in 60 ml of diethyl ether, and the organic layer was washed three times with 20 ml of water, then washed once with a saturated sodium hydrogen carbonate aqueous solution, and further washed once with a saturated sodium chloride aqueous solution. The organic layer was dried over anhydrous magnesium sulfate, then concentrated under a reduced pressure. The residue obtained was treated by means of a silica gel thin layer chromatography (adsorbent: Silica gel 60 F$_{254}$, E. Merck A. G., thickness: 2 mm, developing solvent: 30% ethyl acetated-hexane). There were obtained 311 mg of 1-[2,5-dimethoxy-3,6-bis(methoxymethoxy)-4-chlorophenyl]-5-[2,5-dimethoxy-3,6-bis(methoxymethoxy)phenyl]pentane, and 145 mg of 2,2'-pentamethylenebis[1,4-dimethoxy-3,6-bis(methoxymethoxy)-5-chlorobenzene].

(1) The former compound: 1-[2,5-dimethoxy-3,6-bis(methoxymethoxy)-4-chlorophenyl]-5-[2,5-dimethoxy 3,6-bis(methoxymethoxy)phenyl]pentane Light yellow oily substance.

PMR, δ ppm (CDCl$_3$): 1.40–1.70 (6H, m), 2.55–2.78 (4H, m), 3.53 (3H, s), 3.57 (6H, s), 3.65 (3H, s), 3.79 (3H, s), 3.80 (6H, s), 3.82 (3H, s), 5.02 (2H, s), 5.08 (2H, s), 5.13 (2H, s), 5.18 (2H, s), 6.65 (1H, s).

(2) The latter compound: 2,2'-pentamethylenebis[1,-4dimethoxy-3,6-bis(methoxymethoxy)-5-chlorobenzene] Light yellow oily substance.

PMR, δ ppm (CDCl$_3$) 1.41–1.67 (6H, m), 2.58–2.70 (4H, m), 3.58 (6H, s), 3.66 (6H, s), 3.81 (6H, s), 3.83 (6H, s), 5.09 (4H, s), 5.14 (4H, s).

EXAMPLE 121

219 Milligrams (0.35 mM) of 1-[2,5-dimethoxy-3,6-bis(methoxymethoxy)-4-chlorophenyl]-5-[2,5-dimethoxy-3,6-bis(methoxymethoxy)phenyl]pentane was dissolved in 5 ml of a mixed solvent of ethanol-tetrahydrofuran (1:1), to this solution was added 0.5 ml of a mixed solvent of ethanol-tetrahydrofuran (1:1) containing 20% of hydrogen chloride under an atmosphere of argon gas at a room temperature, then the reaction mixture was stirred for 2 hours at 60° C. The solvent was removed under reduced pressure, to the residue was added 5 ml of benzene, and the mixture was again treated under reduced pressure to remove the hydrogen chloride. The residue obtained was dissolved in 20 ml of acetonitrile, further added 1.5 ml of acetonitrile solution of complex of Cu$_4$Cl$_4$O$_2$ (CH$_3$CN)$_3$ (which was prepared by adding 1 g of cuprous chloride in 25 ml of acetonitrile under bubbling oxygen gas), and the reaction mixture was stirred for 1 hour under oxygen gas stream conditions. The solvent was removed under reduced pressure, the residue obtained was dissolved in 30 ml of ethyl acetate, then the organic layer was washed three times with 10 ml of water, then washed once with 10 ml of a saturated sodium chloride aqueous solution. The organic layer was dried over anhydrous magnesium sulfate, then concentrated under a reduced pressure. The residue obtained was treated by means of a silica gel thin layer chromatography (adsorbent: Silica gel 60 F$_{254}$, E. Merck A. G.-thickness: 1 mm, developing solvent: 50% ethyl acetate-n-hexane) to obtain 107 mg of 2,5-dimethoxy-3-chloro-6-[5-(2,5-dimethoxy-1,4-benzoquinon-3-yl)pentyl]-1,4-benzoquinone. Orange powdery substance.

Melting point: 44.8°–46° C.

PMR, δ ppm (CDCl$_3$) 1.20–1.64 (6H, m), 2.28–2.50 (4H, m), 3.81 (3H, s), 4.05 (3H, s), 4.06 (3H, s), 4.21 (3H, s), 5.73 (1H, s).

EXAMPLE 122

145 Milligrams (0.22 mM) of 2,2'-pentamethylenebis[1,4-dimethoxy-3,6-bis(methoxymethoxy)-5-chlorobenzene]was dissolved in a 5 ml of mixed solvent of ethanoltetrahydrofuran (1:1), to this solution was added 0.5 ml of a mixture of ethanol-tetrahydrofuran (1:1) containing 20% of hydrogen chloride under an atmosphere of argon gas at room temperature, then the reaction mixture was stirred for 2 hours at 80° C. The solvent was removed under reduced pressure, then to the residued was added 5 ml of benzene, and this mixture again treated under reduced pressure to remove the hydrogen chloride. The residue obtained was dissolved in 20 ml of acetonitrile, further added 1.5 ml of acetonitrile solution of complex of Cu$_4$Cl$_4$O$_2$(CH$_3$CN)$_3$ (which was prepared by adding 1 g of cuprous chloride in 25 ml of acetonitrile under oxygent gas stream conditions), and the reaction mixture was stirred for 30 minutes under bubbling oxygen gas. The solvent was removed under a reduced pressure, the residue obtained was dissolved in 30 ml of ethyl acetate, the organic layer was washed three times with 10 ml of water, then washed once with 10 ml of a saturated sodium chloride aqueous solution. The organic layer was then dried over anhydrous magnesium sulfate and concentrated under a reduced pressure. The residue obtained was treated by means of a silica gel thin layer chromatography (adsorbent: "Silica gel 60 F$_{254}$", E. Merck A. G., thickness: 1 mm, developing solvent: 30% ethyl acetate-hexane). There was obtained 67 mg of 6,6'-pentamethylenebis(2,5-dimethoxy-3-chloro-1,4-benzoquinone). Orange needles crystals.

Melting point: 79.8°–80.0° C.

PMR, δ ppm (CDCl$_3$) 1.28–1.50 (6H, m), 2.32–2.48 (4H, m), 4.06 (6H, s), 4.21 (6H, s).

EXAMPLE 123

(1) 3.0 Grams of 1,4-dimethoxy-2,5-bis(methoxymethoxy)benzene was dissolved in 500 ml of anhydrous tetrahydrofuran, this solution was cooled to −78° C. on a dry ice-acetone bath under an atmosphere of argon gas. To this solution was added dropwise 10.7 ml of secbutyllithium (1.3M cyclohexane solution), and stirred for 30 minutes. Then 3.54 g of 1-bromo-4-nonyne was added dropwise thereto, further 2.1 g of sodium iodide and 60 ml of hexamethylphosphoric triamide were added to the reaction mixture and stirred for 12 hours at room temperature. Tetrahydrofuran was removed under reduced pressure, then to the residue obtained was added 300 ml of mixed solvent of benzene-diethyl ether (1:1). The organic layer was washed four times with 100 ml of water, and washed four times with 100 ml of a saturated sodium chloride aqueous solution, dried over anhydrous magnesium sulfate then the solvent was removed under reduced pressure. The residue obtained was treated by means of a silica gel column chromatography (diameter: 5.5 cm×length 15.5 cm, "Wakogel C-200", developing and eluting solvent: 20% ethyl acetate-n-hexane). There was obtained 1.4 g of 1,4-dimethoxy-2,5-bis(methoxymethoxy)-3-(4-nonynyl)benzene as in the form of colorless oily substance.

PMR, δ ppm (CDCl$_3$): 0.89 (3H, t, J=7.0Hz), 1.43 (4H, m), 1.74 (2H, m), 2.14 (2H, m), 2.22 (2H, m), 2.75 (2H, brt), 3.52 (3H, s), 3.58 (3H, s), 3.78 (6H, s), 5.01 (2H, s), 5.16 (2H, s), 6.64 (1H, s).

(2) 1.0 Gram of 1,4-dimethoxy-2,5-bis(methoxymethoxy)-3-(4-nonynyl)benzene prepared in the above-mentioned process (1) was treated for the removal of methoxymethyl group and was oxidized by employed procedures similar to those described in Example 30 (4), there was obtained 530 mg of 2,5-dimethoxy-3-(4-nonynyl)$_{1,4}$-benzoquinone. Yellow oily substance.

PMR, δ ppm (CDCl$_3$) 0.90 (3H, t, J=7.0Hz), 1.3–1.5 (4H, m), 1.61 (2H, m), 2.15 (4H, m), 2.52 (2H, t, J=7.6Hz), 3.80 (3H, s), 4.07 (3H, s), 5.73 (1H, s).

EXAMPLE 124

390 Milligrams of 1-(2-hydroxyethyl)-2,5-dimethoxy-3,6-bis(methoxymethoxy)-4-{5-[3,6-dimethoxy-2,5-bis(methoxymethoxy)phenyl]pentyl}benzene prepared in Example 58 was treated for the removal of methoxymethyl group and was oxidized by employed procedures similar to those described in Example 123, there was obtained 92 mg of 2,5-dimethoxy-3-(2-hydroxyethyl)-6-[5-(2,5-dimethoxy-1,4-benzoquino-3-yl)pentyl]-1,4-benzoquinone. Orange needles crystals.

Melting point: 86°–87° C.

PMR δ ppm (CDCl$_3$) 1.3–1.5 (6H, m), 2.40 (2H, t, J=7.3Hz), 2.43 (2H, t, J=7.3Hz), 2.72 (2H, t, J=6.5Hz), 3.73 (2H, t, J=6.5Hz), 3.80 (3H, s), 4.00 (3H, s), 4.04 (3H, s), 4.06 (3H, s), 5.73 (1H, s).

EXAMPLE 125

Milligrams of 2,2'-pentamethylenebis(3,6-dimethoxy-1,4-benzoquinone) dissolved in 7 ml of methanol, was treated with 2N-sodium hydroxide, and then warmed at about 90° C. for 30 minutes. After cooling, the solution was adjusted to pH 3 with 6N-hydrochloric acid, and extracted with the mixed solvent of 150 ml of ethyl acetate-ethyl ether (1:1). The organic layer was washed twice with water and twice with an aqueous solution saturated with sodium chloride, and concentrated under reduced pressure to give 203 mg of 2,2'-pentamethylenebis(3,6-dihydroxy-1,4-benzoquinone). Yellow powdery substance.

PMR, δ ppm ($D_6$-DMSO): 1.2–1.5 (6H, m), 2.27 (4H, t, J=7.0Hz), 5.78 (2H, s), 10.9–11.4 (4H, br).

EXAMPLE 126

200 Milligrams of 2,2'-pentamethylenebis(3,6-dihydroxy-1,4-benzoquinone), prepared in the abovementioned Example 125 was suspended in 7 ml of tetrahydrofuran and thereto were added 5.1 ml of acetyl chloride and 6.8 ml of triethylamine. After being stirred at room temperature overnight, the reaction mixture was poured into 50 ml of ice-water, and extracted with 100 ml of ethyl acetate. The organic layer was washed twice with water and twice with an aqueous solution saturated with sodium chloride, and dried over anhydrous magnesium sulfate, and concentrated under reduced pressure. The residue was purified by means of the preparative thin layer chromatography (adsorbent: Silica gel 60 $F_{254}$, E. Merck A. G., solvent: 5% ethyl acetate-dichloromethane) to give 151 mg of 2,2'-pentamethylenebis(3,6-diacetoxy-1,4-benzoquinone). Yellow powdery substance.

PMR, δ ppm ($CDCl_3$) 1.2–1.6 (6H, m), 2.34 (6H, s), 2.36 (6H, s), 2.42 (4H, t, J=6.7Hz), 6.55 (2H, s).

EXAMPLE 127

By use of the procedures similar to those described in Example 126, except that 7 mg of 2,2'-pentamethylenebis(3-hydroxy-6-methoxy-1,4-benzoquinone) was used in place of 2,2'-pentamethylenebis(3,6-dihydroxy-1,4-benzoquinone), there was obtained 4 mg of 2,2'-pentamethylenebis(3-acetoxy-6-methoxy-1,4-benzoquinone). Yellow oily substance.

PMR, δ ppm ($CDCl_3$) 1.2–1.5 (6H, m), 2.36 (6H, s), 2.41 (4H, t, J=7.4Hz), 3.84 (6H, s), 5.89 (2H, s).

Pharmacological Tests

The results of pharmacological tests of the present 1,4-benzoquinone derivatives and benzene derivatives are shown below. The test compounds used in the tests are as follows.

| Test Compound No. | |
|---|---|
| 1. | 5-Methoxy-3-(Z-10-pentadecenyl)-1,4-benzoquinone |
| 2. | 5-Methoxy-2-hydroxy-3-(Z-8-tridecenyl)-1,4-benzoquinone |
| 3. | 1-(5-Methoxy-2-hydroxy-1,4-benzoquinon-3-yl)-16-(5-methoxy-2-hydroxy-6-methyl-1,4-benzoquinon-3-yl)-Z-8-hexadecene |
| 4. | 1,16-bis(5-Methoxy-2-hydroxy-1,4-benzoquinon-3-yl)-8,9-epoxyhexadecane |
| 5. | 1,16-(2,5-Dimethoxy-1,4-benzoquinon-3-yl)-8,9-epoxyhexadecane |
| 6. | 1-(2-Hydroxy-5-methoxy-1,4-benzoquinon-3-yl)-16-(4-methyl-3,5-dihydroxyphenyl)-Z-8-hexadecene |
| 7. | 1-(2-Hydroxy-5-methoxy-1,4-benzoquinon-3-yl)-16-(3,5-dihydroxyphenyl)-Z-8-hexadecene |
| 8. | 2,5-Dimethoxy-3-tridecanyl-1,4-benzoquinone |
| 9. | 2,2'-Pentamethylenebis(3,6-dimethoxy-1,4-benzoquinone) |
| 10. | 2,2'-Hexamethylenebis(3,6-dimethoxy-1,4-benzoquinone) |
| 11. | 2,2'-Heptamethylenebis(3,6-dimethoxy-1,4-benzoquinone) |
| 12. | 2,2'-Octamethylenebis(3,6-dimethoxy-1,4-benzoquinone) |
| 13. | 2,2'-Nonamethylenebis(3,6-dimethoxy-1,4-benzoquinone) |
| 14. | 2,2'-Decamethylenebis(3,6-dimethoxy-1,4-benzoquinone) |
| 15. | 2,2'-Dodecamethylenebis(3,6-dimethoxy-1,4-benzoquinone) |
| 16. | 2,2'-(6-Dodecynylene)bis(3,6-dimethoxy-1,4-benzoquinone) |
| 17. | 2,2'-Pentamethylenebis(3,6-dimethoxy-5-methyl-1,4-benzoquinone) |
| 18. | 2,5-Dimethoxy-3-methyl-6-[5-(2,5-dimethoxy-1,4-benzoquinon-3-yl)pentyl]-1,4-benzoquinone |
| 19. | 5,5'-Pentamethylenebis[2-(2-hydroxyethyl)-3,6-dimethoxy-1,4-benzoquinone] |
| 20. | 2,2'-(8-Hexadecynylene)bis(3,6-dimethoxy-1,4-benzoquinone) |
| 21. | 2,2'-(10-Eicosynylene)bis(3,6-dimethoxy-1,4-benzoquinone) |
| 22. | 2,2'-Methylenebis(3,6-dimethoxy-1,4-benzoquinone) |
| 23. | 2,2'-Ethylenebis(3,6-dimethoxy-1,4-benzoquinone) |
| 24. | 2,2'-Tetramethylenebis(3,6-dimethoxy-1,4-benzoquinone) |
| 25. | 2-(3,6-Dimethoxy-1,4-benzoquinon-2-yl)ethyl 3-(3,6-dimethoxy-1,4-benzoquinon-2-yl)propyl ether |
| 26. | Bis[(3,6-Dimethoxy-1,4-benzoquinon-2-yl)methyl] ether |
| 27. | 2,2'-Trimethylenebis(3,6-dimethoxy-1,4-benzoquinone) |
| 28. | Bis[(3,6-dimethoxy-1,4-benzoquinon-2-yl)propyl] disulfide |
| 29. | Bis[(3,6-dimethoxy-1,4-benzoquinon-2-yl)pentyl]sulfide |
| 30. | 2,5-Dimethoxy-3-(6-undecynyl)-1,4-benzoquinone |
| 31. | 2,5-Dimethoxy-3-(8-tridecynyl)-1,4-benzoquinone |
| 32. | 2,5-Dimethoxy-3-(10-pentadecynyl)-1,4-benzoquinone |
| 33. | 2,5-Dimethoxy-3-(Z-6-undecenyl)-1,4-benzoquinone |
| 34. | 2,5-Dimethoxy-3-(Z-8-tridecenyl)-1,4-benzoquinone |
| 35. | 2,5-Dimethoxy-3-(4-nonynyl)-1,4-benzoquinone |
| 36. | 1,5-bis[1,4-Dimethoxy-2,5-bis(methoxymethoxy)-phen-3-yl]pentane |
| 37. | 1,5-bis[1,4-Diacetoxy-2,5-(dimethoxy)phen-3-yl]pentane |
| 38. | 3-Butyl-2,5-dimethoxy-6-[5-(2,5-dimethoxy-1,4-benzoquinon-3-yl)pentyl]-1,4-benzoquinone |
| 39. | 2,5 Dimethoxy-3-(4-nonynyl)-6-[5-(2,5-dimethoxy-1,4-benzoquinon-3-yl)pentyl]-1,4-benzoquinone |
| 40. | 2,5-Dimethoxy-3-(2-hydroxyethyl)-6-[5-(2,5-dimethoxy-1,4-benzoquinon-3-yl)pentyl]-1,4-benzoquinone |
| 41. | 2,5-Dimethoxy-3,6-bis[5-(2,5-dimethoxy-1,4-benzoquinon-3-yl)-entyl]-1,4-benzoquinone |
| 42. | 2,2'-Trimethylenedioxybis(3,6-dimethoxy-1,4-benzoquinone) |
| 43. | 1-(2,5-Dimethoxy-1,4-benzoquinon-3-yl)-5-(2,5-dimethoxy-3-methylthio-1,4-benzoquinon-6-yl)pentane |
| 44. | 1-(2,5-Dimethoxy-1,4-benzoquinon-3-yl)-5-(2,5-dimethoxy-3-ethoxycarbonyl-1,4-benzoquinon-6-yl)pentane |
| 45. | 2,2'-Pentamethylenebis(3,6-dimethoxy-5-methylthio-1,4-benzoquinone) |
| 46. | 2,2'-Pentamethylenebis(3,6-dimethoxy-5- |

| Test Compound No. | |
|---|---|
| | ethoxycarbonyl-1,4-benzoquinone) |
| 47. | 1-(2,5-Dimethoxy-3-butyl-1,4-benzoquinon-6-yl)-[2,5-dimethoxy-3-(2-hydroxyethyl)-1,4-benzoquinon-6-yl]pentane |
| 48. | 1-(2,3,5-Trimethoxy-1,4-benzoquinon-6-yl)-5-[2,5-dimethoxy-3-(2-hydroxyethyl)-1,4-benzoquinon-6-yl]pentane |
| 49. | 1-(2,5-Dimethoxy-3-methylthio-1,4-benzoquinon-6-yl)-5-[2,5-dimethoxy-3-(2-hydroxyethyl)-1,4-benzoquinon-6-yl]pentane |
| 50. | 1-(2,5-Dimethoxy-3-ethoxycarbonyl-1,4-benzoquinon-6-yl)-5-[2,5-dimethoxy-3-(2-hydroxyethyl)-1,4-benzoquinon-6-yl]pentane |
| 51. | 2,2'-Pentamethylenebis(3-hydroxy-6-methoxy-1,4-benzoquinone) |
| 52. | 2,2'-Pentamethylenebis(3,6-diamino-1,4-benzoquinone) |
| 53. | 2,3,5-Trimethoxy-6-[5-(2,5-dimethoxy-1,4-benzoquinon-3-yl)pentyl]-1,4-benzoquinone |
| 54. | 2,2'-Pentamethylenebis(3,5,6-trimethoxy-1,4-benzoquinone) |
| 55. | 2,2'-Pentamethylenebis(3,5,6-trimethyl-1,4-benzoquinone) |

Pharmacological Test-1

5-Lipoxygenase inhibitory activity of the present compounds was determined by a method according to procedures described in "J. Biol. Chem., Vol. 256, pages 4156–4159, (1981, Ibid. Vol. 258, pages 5754–5758 (1983).

(1) Preparation of Test Cells

A guinea pig (Hartley strain) (500–650 g body weight) was intraperitoneally administered with 2%-casein solution in 3/50 the volume of body weight. 14 Hours after the administration, the animal was sacrificed by bleeding and the peritoneal cavity was washed with Dulbecco's phosphate buffered saline (PBS) containing 3 U/ml of heparin and the exudate cells were harvested. The sample of cells was washed twice with Dulbecco's PBS (−), then the cells were suspended in Dulbecco's PBS (−), containing 1 mM of calcium chloride and 5.5 mM of glucose, so as to make a suspension having the concentration of $2.5 \times 10^7$ cells/ml.

(2) Enzymatic Reaction

To 0.2 ml of the above-mentioned cell suspension was added $10^{-5}$M of Indomethacine, and incubated at 30° C. for 2 minutes. Each of the appropriate concentrations of test compounds was added to the suspension respectively, further incubated for 2 minutes. Next, 10 μm of Ionophore A23187 (manufactured by Calbiochem-Behring, San Diego, Calif., U. S. A) was added to the suspension, further, 10 μm of $^{14}$C-arachidonic acid (manufactured by Amersham Japan, Ltd., Tokyo, Japan) was added and initiated the reaction. 3 Minutes after the initiation of the reaction, 0.1 ml of 0.2M-citric acid was added so as to terminate the reaction. 1.2 Milliliters of ethyl acetate was added to the reaction mixture and shaked for 5 minutes. The reaction mixture was centrifuged at 3,000 rpm for 5 minutes so as to separate the organic layer from the aqueous layer. 1 Milliliter of the organic layer (the upper layer) was dehydrated by passing through a mini-column packed with anhydrous sodium sulfate. The dehydrated organic layer was dried under nitrogen gas stream. The residue obtained was dissolved in ethyl acetate, and the total amount of the ethyl acetate solution was spotted onto thin layer chromochromatography (TCL) plate (Art. 11845 manufactured by E. Merck A. G.). The TCL was carried out with a mixed solvent of diethyl ether:petroleum:ether:acetic acid (50:50:1 volume/volume), then the radioactive metabolites on the plate were detected by using "Ultrafilm $^3$H" (a trademark for a X-ray film, manufactured by LKB Co.). Each fractions corresponding to the metabolites was scraped in to a scintillation vial, and 5 ml of "Scintilator ACS-II" (manufactured by Amersham Japan, Ltd.), was added then the radio-activity was determined by means of a liquid scintillation counter.

The inhibition of 5-lipoxygenase activity was shown as inhibition ratio (%) of the conversion of the arachidonic acid to a metabolite [5-hydroxyeicosatetraenoic acid (5-HETE)] of arachidonic acid. $IC_{50}$ of nordihydroguaiaretic acid (NDGA) in this reaction system is was 1 to 2 μm.

The results are shown in Table 1 as follows.

TABLE 1

| Test Compound No. | Concentration (M) | | | | | |
|---|---|---|---|---|---|---|
| | $10^{-7}$ | $3 \times 10^{-7}$ | $10^{-6}$ | $3 \times 10^{-6}$ | $10^{-5}$ | $3 \times 10^{-5}$ |
| 1 | — | — | 10 | 13 | 81 | 87 |
| 2 | 10 | 22 | 67 | — | — | — |
| 3 | 4 | 44 | 86 | 95 | 97 | 96 |
| 4 | 66 | 92 | 96 | 96 | — | — |
| 5 | 17 | 24 | 86 | 86 | — | — |
| 6 | 7 | 29 | 58 | — | — | — |
| 7 | 24 | 28 | 70 | 80 | — | — |
| 8 | — | — | 12 | 40 | 74 | — |
| 9 | 38 | 55 | 74 | — | — | — |
| 10 | 17 | 58 | 81 | — | — | — |
| 11 | 44 | 64 | 88 | — | — | — |
| 12 | 36 | 72 | 87 | — | — | — |
| 13 | 43 | 72 | 91 | — | — | — |
| 14 | 34 | 78 | 89 | — | — | — |
| 15 | 5 | 37 | 77 | — | — | — |
| 16 | 61 | 84 | 87 | — | — | — |
| 17 | 13 | 79 | 89 | — | — | — |
| 18 | 17 | 33 | 53 | — | — | — |
| 19 | 48 | 74 | 87 | — | — | — |
| 30 | — | 39 | 75 | 92 | 91 | — |
| 31 | — | 43 | 73 | 91 | 93 | — |
| 32 | — | 36 | 56 | 80 | 87 | — |
| 33 | — | 51 | 87 | 91 | 89 | — |
| 34 | — | 26 | 37 | 73 | 89 | — |

Pharmacological Test-2

Inhibitory activities on the release of SRS-A and histamine of the present compounds were determined.

A male guinea pig (Hartley strain) (body weight: about 300 g) was sensitized by a method according to P. Anderson: "Int. Archs. Allergey appln. Immunol., Vol. 64, pages 249–258 (1981). Thus, 30 mg/kg of cyclophosphamide was intraperitoneally administered to the guinea pig, and 2 days after 1 microgram of ovalbumin (manufactured by Sigma Chemical Co., St. Louis, Mo. U. S. A.) together with 10 mg of aluminium hydroxide gel were intraperitoneally administered so as to have the animal sesitized.

50 Days after the sesitization, the animal was killed by exsanguination, and the lung was isolated from the animal and was perfused with 20 ml of Tyrode's solution, then immersed in an ice-cooled Tyrode's solution. The parenchyma of the lung was cut by using McIlwain-type tissue chopper to make it into fragments of lung having 2 mm square and the fragments were washed with Tyrode's solution. 400 Milligrams of sectiles of lung were suspended in 3.6 ml of Tyrode's solution, and this suspension was preincubated at 37° C. for 5 minutes, then 4 microliters of dimethyl sulfoxide solution of the test compound, in the case of control 4 microliters of dimethyl sulfoxide alone was added to the suspension. 5 Minutes after, 0.4 ml of 100 micrograms/ml of ovalbumin solution added so as to release SRS-A for 10 minutes. The suspension was ice-cooled and filtered through gauze, the filtrate was centrifuged at 2,000 rpm for 10 minutes and the supernatant was collected. The supernatant was stored in freezed state at $-80°$ C. until bio-assay was conducted.

Amounts of SRS-A and histamine contained in the supernatant were determined by bio-assay using ileum of guinea pig.

A piece of the ileum (2-3 cm of length) positioned from 15-25 cm from the opening portion of ileocecum was isolated from a male guinea pig (Hartley strain) (body weight: 400-600 g) which was fasted for 24 hours. The piece of ileum was hanged vertically in a Magnus tube which was filled with 10 ml of Tyrode's solution containing $10^{-7}$M of atropine sulfate under air stream conditions. The isotonic contraction of the piece of the ileum was measured at 0.5 g of load by using an isotonic transducer "TD-112S" (manufactured by Nihon Koden Co., Ltd.). The measurements were carried out after the reaction to histamine of the piece of ileum was kept constant. Bioassay of histamine was measured by using the value of contraction shown in 30 seconds after the addition of the supernatant. Bioassay of on SRS-A was measured by using the value of contraction shown at 2 minutes after the addition of the supernatant in the presence of $10^{-6}$M of pyrilamine (manufactured by Sigma Chemical Co.), and compared with the standard curve of crude SRS-A released from the fragments of the lung. The results are shown in Tables 2A and 2B as follows.

TABLE 2

| Test Compound No. | Dose (μM) | Inhibition ratio (%) | |
|---|---|---|---|
| | | Histamine | SRS-A |
| 9 | 3 | −15.0 | 50.3 |
| | 30 | 4.1 | >94.8 |
| 10 | 3 | 20.6 | 73.4 |
| | 30 | 22.4 | >95.2 |
| 11 | 3 | −8.4 | 32.5 |
| | 30 | −3.6 | 85.7 |
| 12 | 3 | 2.4 | 26.9 |
| | 30 | −2.2 | 71.7 |
| 13 | 3 | −2.7 | 22.4 |
| | 30 | −14.9 | 43.9 |
| 14 | 3 | −12.6 | 4.5 |
| | 30 | −23.5 | 29.2 |
| 15 | 3 | −10.4 | 3.4 |
| | 30 | −16.0 | 3.8 |
| 16 | 3 | — | 23.4 |
| | 30 | — | 43.9 |
| 17 | 3 | — | 56.3 |
| | 30 | — | 83.9 |
| 18 | 3 | 14.4 | 62.9 |
| | 30 | 8.3 | 91.9 |
| 19 | 3 | — | 40.6 |
| | 30 | — | 76.6 |
| 20 | 3 | — | 14.5 |
| | 30 | — | 24.1 |
| 21 | 3 | — | −21.7 |
| | 30 | — | 16.6 |

TABLE 2B

| Test Compound No. | Inhibitory activities on SRS-A (%) | | | | NDGA (*) |
|---|---|---|---|---|---|
| | 1 μM | 3 μM | 10 μM | 30 μM | 30 μM |
| 22 | 37.6 | — | 85.4 | — | 47.2 |
| 23 | — | — | — | 28.6 | 32.0 |
| 24 | 36.1 | — | 67.7 | — | 30.9 |
| 25 | 52.4 | — | 94.4 | — | 30.9 |
| 26 | — | 10.9 | — | 39.8 | 47.7 |
| 27 | 14.9 | — | 83.3 | — | 47.2 |
| 28 | 30.5 | — | 85.2 | — | 44.4 |
| 29 | 19.6 | — | 60.5 | — | 44.4 |
| 35 | — | 64.9 | — | 96.0 | 32.0 |
| 30 | — | 23.8 | — | 73.4 | — |
| 31 | — | 17.0 | — | 37.7 | 26.9 |
| 32 | — | 12.4 | — | 26.0 | — |
| 33 | — | 19.6 | — | 33.4 | — |
| 34 | — | 3.2 | — | 0.8 | 24.9 |
| 9 | — | 50.3 | — | 94.2 | — |
| 11 | — | 32.5 | — | 85.7 | 27.3 |
| 13 | — | 22.4 | — | 43.9 | — |
| 16 | — | 23.4 | — | 43.9 | — |
| 20 | — | 14.5 | — | 24.1 | 32.0 |
| 21 | — | −21.7 | — | 16.6 | — |
| 36 | — | 12.1 | — | 24.5 | 27.3 |
| 37 | — | 69.2 | — | 90.0 | 63.0 |
| 38 | 25.1 | — | 38.2 | — | 54.6 |
| 39 | 0 | — | 11.0 | — | 47.2 |
| 40 | 38.2 | — | 91.7 | — | 30.9 |
| 41 | 4.1 | — | 25.0 | — | 47.2 |
| 43 | 23.2 | — | 79.4 | — | — |
| 44 | −10.5 | — | 18.6 | — | 47.6 |
| 19 | — | 40.6 | — | 76.6 | 47.7 |
| 45 | 28.1 | — | 50.7 | — | 47.6 |
| 46 | 18.2 | — | 16.2 | — | 44.4 |
| 47 | 15.8 | — | 47.6 | — | 54.6 |
| 48 | 37.6 | — | 89.4 | — | 47.6 |
| 49 | −0.4 | — | 65.2 | — | — |
| 50 | 14.8 | — | 41.7 | — | 54.6 |
| 51 | 11.8 | — | 60.8 | — | 30.9 |
| 52 | 10.0 | — | 16.2 | — | 44.4 |
| 53 | 50.8 | — | 94.9 | — | 14.7 |
| 54 | 32.0 | — | 88.7 | — | 14.7 |
| 55 | 13.2 | — | 38.7 | — | 14.7 |
| 42 | 28.4 | — | 80.0 | — | 14.7 |

Note: (*) The inhibitory activities on NDGA at 30 M was conducted each of the test compound.

Pharmacological Test- 3

SRS-A and histamine releasing inhibition test on anaphylaxis in abdominal cavity of rats.

Male or female rats (Sprague-Dawley strain, delivered from Charles River, Japan Ltd., Tokyo) of 6-7 week age were used as the test animals. The test animals were devided into a group consisting of 6 animals in one group depending on their body weight. The animals were fasted overnight. The test was conducted by a method according to P. T. Orange et al.: "J. Immunol., Vol. 105", pages 1087-1095 (1970).

1 Milliliter each of twofold diluted anti-ovalbumin serm of rat was intraperitoneally injected to each of the test animal so as to have the rat sensitized. 2 Hours after the sensitization, 5 ml of Tyrode's solution containing 2 mg of ovalbumin and 250 micrograms of heparin sodium was intraperitoneally administered to the test animal to cause anaphylaxis. 5 Minutes after, the test animal was stunned by the blow on the head and was exsanguinated and killed by cervical incision. Additional 5 minutes later, the abdominal fluid was collected from the opening of the abdomen. The fluid collected was centrifuged at 4° C., first at 800 rpm, then at 2,500 rpm and the supernatant was collected, and stored at $-80°$ C. until the bioassay was conducted.

Test compound was suspended in 5%-gum arabic aqueous solution and orally administered in the volume of 5 ml/kg 3 hours before the anaphylaxis was caused.

As to the control test, 5%-gum arabic aqueous solution alone was administered.

The amount of SRS-A and histamine contained in the collected abdominal fluid was measured by a method similar to that employed in Pharmacological test-2.

Bio-assay of the collected abdominal fluid was conducted by using ileum of guinea pig which was treated with atropine. Thus, a piece of the ileum (2-3 cm of length) positioned from 15-25 cm from the opening portion of ileocecum was isolated from a guinea pig which was fasted overnight. The piece of ileum was hanged vertically in an organ bath which was filled with 10 ml of Tyrode's solution containing $10^{-7}$M of atropine sulfate under air stream conditions. The isotonic contraction of the piece of the ileum was measured at 0.5 g of load by using an isotonic transducer "TD-112S" (manufactured by Nihon Koden Co., Ltd.). The measurements were recorded on an ink-writing recorder.

After stabilization of the contraction reaction due to histmine, the amount of histamine was measured quantitatively by observing the contraction of the piece of the ileum shown within 30 seconds after addition of 0.05-0.4 ml of the abdominal fluid.

The amount of SRS-A was measured by using the value of contraction shown after the addition of 0.2-0.5 ml of the collected fluid in the presence of $10^{-7}$M of pyrilamine (antihistaminic agent), said value of the contraction was calculated as contraction activity caused by 5 ng of histamine.

The antiovalbumin serum used in this test was prepared by intramuscularly injected 1 mg of ovalbumin to SD-strain rat of 8 week age, then $2 \times 10^{10}$ cells of killed *Bordetella pertussis* was intraperitoneally injected and collected 14 days after the injection. This serum shows 256-fold titer in 48 hours-PCA reaction, and reduces to 4-fold of titer by treatment of heating at 56° C. for 2 hours.

The results of inhibitory rate (%) of histamine and SRS-A are shown in Table 3 as follows.

TABLE 3

| Test Compound No. | Inhibitory rate (%) | |
|---|---|---|
| | Histamine | SRS-A |
| 9 | −3.6 | 4.9 |
| 13 | 10.9 | 25.8 |
| 16 | 8.0 | 15.5 |

| Preparation of tablets - 1 | |
|---|---|
| Compound of Example 1: 5-Methoxy-3-(Z-10-pentadecenyl)-1,4-benzoquinone | 20 mg |
| Starch | 130 mg |
| Magnesium stearate | 10 mg |
| Lactose | 40 mg |
| | 200 mg |

By using a conventional method, each tablet containing the above-mentioned formulation was prepared.

| Preparation of tablets - 2 | |
|---|---|
| Compound of Example 2: 5-Methoxy-2-hydroxy-3-(Z-8-tridecenyl)-1,4-benzoquinone | 10 mg |
| Starch | 127 mg |
| Magnesium stearate | 18 mg |
| Lactose | 45 mg |
| | 200 mg |

By using a conventional method, each table containing the above-mentioned formulation was prepared.

| Preparation of tablets - 3 | |
|---|---|
| Compound of Example 4: 1-(5-Methoxy-2-hydroxy-1,4-benzoquinon-3-yl)-16-(5-methoxy-2-hydroxy-6-methyl-1,4-benzoquinon-3-yl)-Z-8-hexadecene | 10 mg |
| Starch | 127 mg |
| Magnesium stearate | 18 mg |
| Lactose | 45 mg |
| | 200 mg |

By using a conventional method, each tablet containing the above-mentioned formulation was prepared.

| Preparation of tablets - 4 | |
|---|---|
| Compound of Example 7: 1,16-bis(5-Methoxy-2-hydroxy-1,4-benzoquinon-3-yl)-8,9-epoxy-hexadecane | 10 mg |
| Starch | 127 mg |
| Magnesium stearate | 18 mg |
| Lactose | 45 mg |
| | 200 mg |

By using a conventional method, each tablet containing the above-mentioned formulation was prepared.

| Preparation of tablets - 5 | |
|---|---|
| Compound of Example 60: 2,2'-Pentamethylenebis(3,6-dimethoxy-1,4-benzoquinone) | 20 mg |
| Starch | 130 mg |
| Magnesium stearate | 10 mg |
| Lactose | 40 mg |
| | 200 mg |

By using a conventional method, each table containing the above-mentioned formulation was prepared.

| Preparation of tablets - 6 | |
|---|---|
| Compound of Example 62: 2,2'-Heptamethylenebis(3,6-dimethoxy-1,4-benzoquinone) | 10 mg |
| Starch | 127 mg |
| Magnesium stearate | 18 mg |
| Lactose | 45 mg |
| | 200 mg |

By using a conventional method, each tablet containing the above-mentioned formulation was prepared.

| Preparation of tablets - 7 | |
|---|---|
| Compound of Example 67: 2,2'-(6-Dodecynylene)bis(3,6-dimethoxy)-1,4-benzoquinone | 10 mg |
| Starch | 127 mg |
| Magnesium stearate | 18 mg |

| Preparation of tablets - 7 | |
| --- | --- |
| Lactose | 45 mg |
| | 200 mg |

By using a conventional method, each tablet containing the above-mentioned formulation was prepared.

| Preparation of tablets - 8 | |
| --- | --- |
| Compound of Example 79: 2,2'-Methylenebis(3,6-dimethoxy-1,4-benzoquinone) | 20 mg |
| Starch | 130 mg |
| Magnesium stearate | 10 mg |
| Lactose | 40 mg |
| | 200 mg |

By using a conventional method, each tablet containing the above-formulation was prepared.

| Preparation of tablets - 9 | |
| --- | --- |
| Compound of Example 80: 2,2'-Ethylenebis(3,6-dimethoxy-1,4-benzoquinone) | 10 mg |
| Starch | 127 mg |
| Magnesium stearate | 18 mg |
| Lactose | 45 mg |
| | 200 mg |

By using a conventional method, each tablet containing the above-mentioned formulation was prepared.

| Preparation of tablets - 10 | |
| --- | --- |
| Compound of Example 81: 2,2'-Tetramethylenebis(3,6-dimethoxy-1,4-benzoquinone) | 10 mg |
| Starch | 127 mg |
| Magnesium stearate | 18 mg |
| Lactose | 45 mg |
| | 200 mg |

By using a conventional method, each tablet containing the above-mentioned formulation was prepared.

| Preparation of aerosol - 1 | |
| --- | --- |
| Compound of Example 70: 2,2'-Pentamethylenebis(3,6-dimethoxy-5-methyl-1,4-benzoquinone) | 1.0 g |
| Sorbitan monosesquilate | 3.0 g |
| Freon 11 | 1.5 g |
| Freon 12 | 3.5 g |
| | 9.0 g |

By using a conventional method, each cylinder containing the above-mentioned formulation was prepared.

| Preparation of aerosol - 2 | |
| --- | --- |
| Compound of Example 71: 2,5-Dimethoxy-3-methyl-6-[5-(2,5-dimethoxy-1,4-benzoquinon-3-yl)-pentyl]-1,4-benzoquinone | 1.0 g |
| Oleic acid | 3.0 g |
| Freon 11 | 1.25 g |
| Freon 12 | 2.5 g |

| Preparation of aerosol - 2 | |
| --- | --- |
| Freon 114 | 1.25 g |
| | 9.0 g |

By using a conventional method, each cylinder containing the above-mentioned formulation was prepared.

| Preparation of aerosol - 3 | |
| --- | --- |
| Compound of Example 82: 2-(3,6-Dimethoxy-1,4-benzoquinon-2-yl)ethyl 3-(3,6-dimethoxy-1,4-benzoquinon-2-yl)propyl ether | 1.0 g |
| Sorbitan monoseaquilate | 3.0 g |
| Freon 11 | 1.5 g |
| Freon 12 | 3.5 g |
| | 9.0 g |

By using a conventional method, each cylinder containing the above-mentioned formulation was prepared.

| Preparation of aerosol - 4 | |
| --- | --- |
| Compound of Example 83: bis[(3,6-Dimethoxy-1,4-benzoquinon-2-yl)methyl]ether | 1.0 g |
| Oleic acid | 3.0 g |
| Freon 11 | 1.25 g |
| Freon 12 | 2.5 g |
| Freon 114 | 1.25 g |
| | 9.0 g |

By using a conventional method, each cylinder containing the above-mentioned formulation was prepared.

What is claimed is:

1. 1,4-benzoquinone compounds or pharmaceutically acceptable salts thereof of the formula

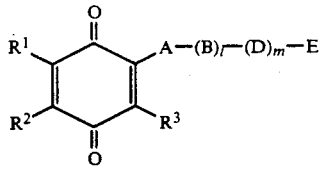

wherein $R^1$ is a lower alkyl group, a lower alkoxy group, an amino group, a hydroxyl group or a lower alkanoyloxy group; $R^2$ is a hydrogen atom, a halogen atom, a lower alkyl group, a lower alkoxy group, a lower alkoxycarbonyl group, or a hydroxy-lower alkyl group; $R^3$ is a hydroxyl group, a lower alkyl group, a lower alkoxy group, an amino group or a lower alkanoyloxy group, A and D are each an alkylene group having 1 to 10 carbon atoms; B is a group of the formula —CH=CH—,

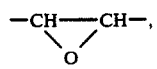

—C≡C— or —CH(OH)—CH(OH)—; l and m are each zero or 1; and E is a group of the formula,

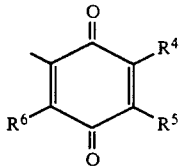

wherein $R^4$ is a lower alkyl group, a lower alkoxy group, an amino group, a hydroxyl group or a lower alkanoyloxy group; $R^5$ is a hydrogen atoms, a halogen atom, a lower alkyl group, a lower alkoxy group, a lower alkoxy-carbonyl group, or a hydroxy-lower alkyl group; and $R^6$ is a lower alkyl group, a hydroxyl group, a lower alkoxy group, an amino group or a lower alkanoyloxy group; furthermore, when m is 1, then l is zero or 1; and when m is zero then l is zero, provided that, (i)
(a) when l is zero and m is zero or 1, then the sum of the number of the carbon atoms in the alkylene groups of A and D is 3 to 12;

(b) when $R^1$, $R^2$, $R^3$, $R^4$, $R^5$ and $R^6$ are each a methyl group at the same time, l is zero and m is zero or 1; then the sum of the number of the carbon atoms, in the alkylene groups of A and D should not be 3;

(ii) when B is a group of the formula —C≡C—, then
(a) $R^1$ and $R^4$ should not be lower alkoxy groups,
(b) $R^2$, $R^3$, $R^5$ and $R^6$ should not be hydrogen atoms, and
(c) A and D should not be heptamethylene groups, respectively;

(iii) when B is a group of the formula —CH=CH—, then
(a) $R^1$ and $R^4$ should not both be a hydroxyl group at the same time and in the case of either of $R^1$ or $R^4$ being a lower alkoxy group, then the other one should not be a lower alkoxy group, a hydroxyl group or a lower alkanoyloxy group,
(b) in the case of either of $R^2$ or $R^5$ being a hydrogen atom or a lower alkyl group, then the other one should not be hydrogen atom,
(c) $R^3$ and $R^6$ should not both be a hydroxyl group at the same time, a hydrogen atom at the same time, or a lower alkanoyloxy group at the same time and in the case of either of $R^3$ or $R^6$ being a hydroxyl group, then the other one should not be a lower alkanoyloxy group, and,
(d) A and D should not be heptamethylene groups, respectively.

2. 1,4-benzoquinone compounds of claim 1, or pharmaceutically acceptable salts thereof wherein $R^1$ is a $C_{1-6}$-alkyl group, a $C_{1-6}$-alkoxy group, an amino group, a hydroxyl group or a $C_{1-6}$-alkanoyloxy group; $R^2$ is a hydrogen atom, a halogen atom, a $C_{1-6}$-alkyl group, a $C_{1-6}$-alkoxy group, a $C_{2-7}$-alkoxycarbonyl group, or a hydroxy-$C_{1-6}$-alkyl group; $R^3$ is a hydroxyl group, a $C_{1-6}$-alkyl group, a $C_{1-6}$-alkoxy group, an amino group or a $C_{1-6}$-alkanoyloxy group; $R^4$ is a $C_{1-6}$-alkyl group, a $C_{1-6}$-alkoxy group, an amino group, a hydroxyl group or a $C_{1-6}$-alkanoyloxy group; $R^5$ is a hydrogen atom, a halogen atom, a $C_{1-6}$-alkyl group, a $C_{1-6}$-alkoxy group, a $C_{2-7}$-alkoxycarbonyl group, or a hydroxy-$C_{1-6}$-alkyl group; and $R^6$ is a $C_{1-6}$-alkyl group, a hydroxyl group, a $C_{1-6}$-alkoxy group, an amino group or a $C_{1-6}$-alkanoyloxy group.

3. 1,4-benzoquinone compounds of claim 2, or pharmaceutically acceptable salts thereof wherein l is zero.

4. 1,4-benzoquinone compounds of claim 3, or pharmaceutically acceptable salts thereof wherein $R^4$ is a $C_{1-6}$-alkoxy group; $R^5$ is a hydrogen atom, a $C_{1-6}$-alkoxy group, or a hydroxy-$C_{1-6}$-alkyl group.

5. 1,4-benzoquinone compounds of claim 4, or pharmaceutically acceptable salts thereof wherein $R^1$ is a $C_{1-6}$-alkoxy group; $R^2$ is a hydrogen atom, a $C_{1-6}$-alkoxy group, or a hydroxy-$C_{1-6}$-alkyl group; and $R^3$ is a hydroxyl group or a $C_{1-6}$-alkoxy group.

6. 1,4-benzoquinone compounds of claim 2, or pharmaceutically acceptable salts thereof wherein l is 1.

7. 1,4-benzoquinone compounds of claim 6 or pharmaceutically acceptable salts thereof wherein $R^1$ and $R^4$ are each a $C_{1-6}$-alkoxy group, $R^2$ and $R^5$ are each a hydrogen atom, a $C_{1-6}$-alkoxy group or a hydroxy-$C_{1-6}$-alkoxy group; and $R^3$ and $R^6$ are each a hydroxyl group or a $C_{1-6}$-alkoxy group.

8. 2,5-bis(2,5-Dimethoxy-1,4-benzoquinon-3-yl)-pentane.

9. 1,9-bis(2,5-Dimethoxy-1-4-benzoquinon-3-yl)-nonane.

10. A 5-Lipoxygenase inhibitor containing a compound of claim 2 as the active ingredient and a pharmaceutically acceptable carrier.

11. An antiasthmatic agent containing a compound of claim 1 as the active ingredient and a pharmaceutically acceptable carrier.

* * * * *

UNITED STATES PATENT AND TRADEMARK OFFICE
CERTIFICATE OF CORRECTION

PATENT NO. : 5,220,042
DATED : July 15, 1993
INVENTOR(S) : Hideyuki Iwaki et al.

It is certified that error appears in the above-indentified patent and that said Letters Patent is hereby corrected as shown below:

Claim 7, column 100, line 38, "alkoxy" should read --alkyl--.

Signed and Sealed this

Tenth Day of May, 1994

Attest:

BRUCE LEHMAN

Attesting Officer     Commissioner of Patents and Trademarks